US008476278B2

(12) United States Patent
Reddy et al.

(10) Patent No.: US 8,476,278 B2
(45) Date of Patent: Jul. 2, 2013

(54) THIAZOLE DERIVATIVES AS PROTEIN KINASE INHIBITORS

(75) Inventors: Panduranga Adulla P. Reddy, Walpole, MA (US); Tzu T. Wong, Belmont, MA (US); Lianyun Zhao, Burlington, MA (US); Shuyi Tang, Belmont, MA (US); Marc A. Labroli, Moorestown, NJ (US); Timothy J. Guzi, Sudbury, MA (US); M. Arshad Siddiqui, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 288 days.

(21) Appl. No.: 12/738,487

(22) PCT Filed: Oct. 27, 2008

(86) PCT No.: PCT/US2008/081316

§ 371 (c)(1), (2), (4) Date: Aug. 31, 2010

(87) PCT Pub. No.: WO2009/058728

PCT Pub. Date: May 7, 2009

(65) Prior Publication Data

US 2010/0331313 A1 Dec. 30, 2010

Related U.S. Application Data

(60) Provisional application No. 60/983,327, filed on Oct. 29, 2007.

(51) Int. Cl.

| | |
|---|---|
| ***A61K 31/496*** | (2006.01) |
| ***C07D 417/14*** | (2006.01) |
| *A61K 31/427* | (2006.01) |
| *A61K 31/551* | (2006.01) |
| *A61K 31/5377* | (2006.01) |
| *C07D 413/14* | (2006.01) |
| *C07D 417/12* | (2006.01) |
| *C07D 471/10* | (2006.01) |

(52) U.S. Cl.

USPC .................... 514/253.1; 514/218; 514/233.5; 514/278; 540/575; 544/60; 544/61; 544/62; 544/121; 544/131; 544/133; 544/364; 546/16

(58) Field of Classification Search

None

See application file for complete search history.

(56) References Cited

U.S. PATENT DOCUMENTS

| | | | | |
|---|---|---|---|---|
| 8,163,746 | B2 * | 4/2012 | Sugasawa et al. | 514/235.8 |
| 8,227,605 | B2 * | 7/2012 | Shipps et al. | 544/366 |

FOREIGN PATENT DOCUMENTS

| | | | |
|---|---|---|---|
| WO | 2008/054701 | * | 5/2008 |
| WO | 2008/054702 | * | 5/2008 |
| WO | 2008/054749 | * | 5/2008 |
| WO | 2009/058730 | * | 5/2009 |
| WO | 2009/058739 | * | 5/2009 |

OTHER PUBLICATIONS

Vippagunta et al Advanced Drug Delivery Reviews, vol. 48, pp. 3-26 (2001).*

Guillory in "Polymorphism in Pharmaceutical Solids", edited by Harry G. Brittain, vol. 95, pp. 202-208 (1999).*

* cited by examiner

*Primary Examiner* — Emily Bernhardt

(74) *Attorney, Agent, or Firm* — Peter Haeberli; David A. Muthard

(57) ABSTRACT

The present invention relates to novel Thiazole Derivatives, compositions comprising the Thiazole Derivatives, and methods for using the Thiazole Derivatives for treating or preventing a proliferative disorder, an anti-proliferative disorder, inflammation, arthritis, a central nervous system disorder, a cardiovascular disease, alopecia, a neuronal disease, an ischemic injury, a viral infection, a fungal infection, or a disorder related to the activity of a protein kinase.

(I)

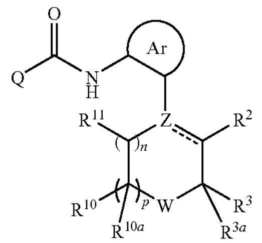

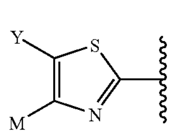

or

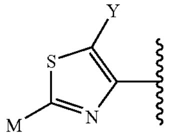

2 Claims, No Drawings

THIAZOLE DERIVATIVES AS PROTEIN KINASE INHIBITORS

FIELD OF THE INVENTION

The present invention relates to novel Thiazole Derivatives, compositions comprising the Thiazole Derivatives, and methods for using the Thiazole Derivatives for treating or preventing a proliferative disorder, an anti-proliferative disorder, inflammation, arthritis, a central nervous system disorder, a cardiovascular disease, alopecia, a neuronal disease, an ischemic injury, a viral infection, a fungal infection, or a disorder related to the activity of a protein kinase.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways—making stimulatory genes hyperactive or inhibitory genes inactive. Protein kinase inhibitors, regulators or modulators alter the function of kinases such as cyclin-dependent kinases (CDKs), mitogen activated protein kinase (MAPK/ERK), glycogen synthase kinase 3 (GSK3beta), Checkpoint (Chk) CHK-1, CHK-2 etc.) kinases, AKT kinases, JNK, and the like. Examples of protein kinase inhibitors are described in WO02/22610 A1 and by Y. Mettey et al., in *J. Med. Chem.,* 46:222-236 (2003).

The cyciin-dependent kinases are serine/threonine protein kinases, which are the driving force behind the cell cycle and cell proliferation. Misregulation of CDK function occurs with high frequency in many important solid tumors. Individual CDK's, such as, CDK1, CDK2, CDK3, CDK4, CDK5, CDK6 and CDK7, CDK8 and the like, perform distinct roles in cell cycle progression and can be classified as either G1S, or G2M phase enzymes. CDK2 and CDK4 are of particular interest because theft activities are frequently misregulated in a wide variety of human cancers. CDK2 activity is required for progression through Si to the S phase of the cell cycle, and CDK2 is one of the key components of the G1 checkpoint, Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over- or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of cancer treatments.

A number of adenosine 5'-triphosphate (ATP) competitive small organic molecules as well as peptides have been reported in the literature as CDK inhibitors for the potential treatment of cancers. U.S. Pat. No. 6,413,974 offers a good description of the various CDKs and their relationship to various types of cancer. Flavopiridol (shown below) is a nonselective CDK inhibitor that is currently undergoing human clinical trials, A. M. Sanderowicz et al., *J. Clin. Oncol.* 16:2986-2999 (1998),

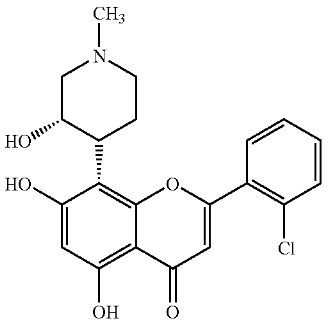

Other known inhibitors of CDKs include, for example, olomoucine (J. Vesely et al., *Eur. J. Biochem.,* 224:771-786 (1994)) and roscovitine (I. Meijer et al., *Eur. J. Biochem.,* 243:527-536 (1997)). U.S. Pat. No. 6,107,305 describes certain pyrazolo[3,4-b]pyridine compounds as CDK inhibitors. An illustrative compound from the '305 patent is:

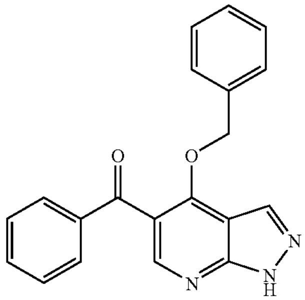 [SMILES: O=C(c1ccccc1)c1cnc2[nH]ncc2c1OCc1ccccc1]

K. S. Kim et al., *J. Med. Chem.* 45:3905-3927 (2002) and WO 02/10162 disclose certain aminothiazole compounds as CDK inhibitors.

Another series of protein kinases are those that play an important role as a checkpoint in cell cycle progression. Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate G.sub.2 arrest induced by DNA damage inflicted by either anticancer agents or endogenous DNA damage, as well as result in preferential killing of the resulting checkpoint defective cells. See, e.g., Peng et al., *Science,* 277:1501-1505 (1997); Sanchez et al., *Science,* 277:1497-1501 (1997), Nurse, *Cell,* 91:865-867 (1997); Weinert. *Science,* 277:1450-1451 (1997): Walworth et al., *Nature,* 363:368-371 (1993); and Al-Khodairy et al., *Molec. Biol. Cell.,* 5:147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature,* 395:507-510 (1998); Matsuoka, *Science,* 282:1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3 and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1 (FLK-1), fetal liver kinase-4 (FLK-4) and the fms-like tyrosine kinase-1 (flt-1). For detailed discussion of the receptor-type tyrosine kinases, see Plowman et al., *DN&P* 7(6):334-339, 1994.

At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene,* 8:2025-2031 (1993). The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further subdivided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, *Oncogene,* 8:2025-2031 (1993).

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Res.,* 56:3540-3545 (1996)), as has been shown with mutants of VEGF-R2 which fail to mediate signal transduction. Millauer et al, *Cancer Res.,* 56:1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji at al., *Cancer Research,* 57: 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal,* 17:5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science,* 277:55-60 (1997).

The kinase, JNK, belongs to the mitogen-activated protein kinase (MAPK) superfamily. JNK plays a crucial role in inflammatory responses, stress responses, cell proliferation, apoptosis, and tumorigenesis. JNK kinase activity can be activated by various stimuli, including the proinflammatory cytokines (TNF-alpha and interleukin-1), lymphocyte costimulatory receptors (CD28 and CD40), DNA-damaging chemicals, radiation, and Fas signaling. Results from the JNK knockout mice indicate that JNK is involved in apoptosis induction and T helper cell differentiation.

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sala-Ser. D Osa-Tom. 616, (Aug. 30, 2005), http://kirjasto.utu.fi/julkaisupalvelut/annaalit/2004/D616.html. Pim-1 acts as a cell survival factor and may prevent apoptosis in malignant cells. K. Petersen Shay et al., *Molecular Cancer Research* 3:170-181 (2005).

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B, Aurora-C have been found to be overexpressed (see Bischoff et al., *EMBO J.,* 17:3052-3065 (1998); Schumacher et al., *J. Cell Biol.* 143:1635-1646 (1998); Kimura et al., *J. Biol. Chem.,* 272:13766-13771 (1997)).

c-Met is a proto-oncogene that encodes for a tyrosine kinase receptor for hepatocyte growth factor/scatter factor (HGF/SF). The c-Met protein is expressed mostly in epithelial cells, and due to its function it is also known as hepatocyte growth factor receptor, or HGFR. When HGF/SF activates c-Met, the latter in turn may activate a number of kinase pathways, including the pathway from Ras to Raf to Mek to the mitogen-activated protein kinase ERK1 to the transcription factor ETS1. Met signaling has been implicated in the etiology and malignant progression of human cancers (see Birchmeier et al., *Nature Reviews Molecular Cell Biology,* 4:915-925 (2003); Zhang et al., *Journal of Cellular Biochemistry,* 88:408-417 (2003); and Paumelle et al., *Oncogene,* 21:2309-2319 (2002)).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNFa), interleukin 6 (IL-6) and interferon gamma (IFNg), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α (see Deak et al., *EMBO.* 17:4426-4441 (1998); Shi et al., *Biol. Chem.* 383:1519-1536 (2002); Staklatvala., *Curr. Opin. Pharmacol.* 4:372-377 (2004); and Shiroto et al., *J. Mol. Cell Cardiol.* 38:93-97 (2005)).

There is a need for effective inhibitors of protein kinases in order to treat or prevent disease states associated with abnormal cell proliferation. Moreover, it is desirable for kinase inhibitors to possess both high affinities for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF (VEGF-R2), Pim-1, CDKs or CDK/cyclin complexes and both receptor and non-receptor tyrosine kinases.

SUMMARY OF THE INVENTION

In one aspect, the present invention provides compounds of Formula (I):

(I)

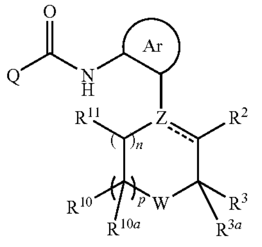

and pharmaceutically acceptable salts, solvates, esters, prodrugs and stereoisomers thereof, wherein the dashed line indicates an optional and additional bond and wherein:

Q is:

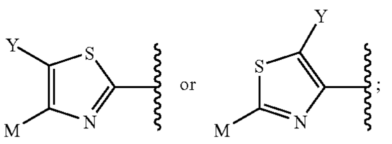

M is $R^1$, —C(O)$R^1$, —(S)$R^1$, —S(O)$R^1$, —$S(O)_2R^1$, —$S(O)_2NHR^1$, —C(O)O$R^1$, —C(O)NH$R^1$, —NHC(O)NH—$R^1$, —NHC(S)NH$R^1$, —NHC(O)O$R^1$, —NH$S(O)_2R^1$, —N($R^1$)(—C(O)$R^1$) or —$N(R^1)_2$; each occurrence of $R^1$ is independently H, alkyl, alkenyl, alkynyl, -(alkylene)$_m$-aryl, -(alkylene)$_m$-cycloalkyl, -(alkylene)$_m$-heteroaryl, -(alkylene)$_m$- heterocycloalkyl or -(alkylene)$_m$-heterocycloalkenyl, wherein any aryl, cycloalkyl, heteroaryl, heterocycloalkyl or heterocycloalkenyl group can be optionally substituted on one or more ring carbon atoms with any of the following substituents, which are each independently selected from halo, alkyl, alkenyl, alkynyl, haloalkyl, hydroxyalkyl, —O$R^6$, -(alkylene)$_m$-$N(R^6)_2$, —C(O)O$R^6$, —NHC(O)$R^6$, —C(O)$N(R^6)_2$, —$S(O)_2R^7$, —CN, —$NO_2$, -(alkylene)$_m$-aryl, -(alkylene)$_m$-cycloalkyl, -(alkylene)$_m$-heteroaryl, -(alkylene)$_m$-heterocycloalkyl and -(alkylene)$_m$-heterocycloalkenyl; wherein any heterocycloalkyl or heterocycloalkenyl group can be optionally substituted on one or more ring nitrogen atoms with any of the following substituents, which are each independently selected from alkyl, alkenyl, alkynyl, haloalkyl, hydroxyalkyl, -(alkylene)$_m$-$N(R^6)_2$, —C(O)O$R^6$, —C(O)$N(R^6)_2$, —$S(O)_2R^7$, -(alkylene)$_m$-aryl, -(alkylene)$_m$-cycloalkyl, -(alkylene)$_m$-heteroaryl, -(alkylene)$_m$-heterocycloalkyl and -(alkylene)$_m$-heterocycloalkenyl; and wherein any aryl or heteroaryl substituent group can be optionally substituted with up to 5 substituents, which may be the same or different, and are selected from halo, —OH, alkyl, —C(O)O$R^6$, —$N(R^6)_2$, —NHC(O)$R^6$, —C(O)$N(R^6)_2$, —$S(O)_2R^7$, —CN, —OH, —$NO_2$, and —O-alkyl; and wherein any aryl, cycloalkyl, heteroaryl, heterocycloalkyl or heterocycloalkenyl group can be optionally fused to an aryl, cycloalkyl, heteroaryl, heterocycloalkyl or heterocycloalkenyl group;

each occurrence of $R^2$ is independently H, alkyl, haloalkyl, hydroxyalkyl, -(alkylene)$_m$-C(O)$N(R^6)_2$, -(alkylene)$_m$-NHC(O)$R^6$ or -(alkylene)$_m$-$N(R^6)_2$, or $R^2$ and the ring carbon atom to which it is attached, combine to form a carbonyl group;

$R^3$ is H, alkyl, haloalkyl, hydroxyalkyl, -(alkylene)$_m$-C(O)$N(R^6)_2$, -(alkylene)$_m$-NHC(O)—$R^6$ or -(alkylene)$_m$-$N(R^6)_2$, or $R^3$ and $R^{3a}$, together with the common carbon atom to which each are attached, join to form a carbonyl group or a spirocyclic cycloalkyl or heterocycloalkyl group;

$R^{3a}$ is H, alkyl, haloalkyl, hydroxyalkyl, -(alkylene)$_m$-C(O)$N(R^6)_2$, -(alkylene)$_m$-NHC(O)—$R^6$ or -(alkylene)$_m$-$N(R^6)_2$;

each occurrence of $R^5$ is independently H, alkyl, -(alkylene)$_m$-aryl, -(alkylene)$_m$-heteroaryl, -(alkylene)$_m$-heterocycloalkyl, -(alkylene)$_m$-$N(R^6)_2$, -(alkylene)$_m$-OH, -(alkylene)$_m$- NHC(O)$R^6$, hydroxyalkyl, haloalkyl, —C(O)$R^6$, —C(O)O$R^6$; —C(O)-(alkylene)$_m$-$N(R^6)_2$, -(alkylene)$_m$-NHC(O)$R^6$, —NHC(O)O$R^6$ or —NH$S(O)_2R^7$;

each occurrence of $R^6$ is independently H, alkyl, haloalkyl, cycloalkyl, aryl, heterocycloalkyl or heteroaryl;

each occurrence of $R^7$ is independently H, alkyl, aryl, cycloalkyl or haloalkyl;

$R^8$ is H, alkyl, —OH, —O-alkyl or haloalkyl;

$R^{10}$ is H, alkyl, haloalkyl, hydroxyalkyl, -(alkylene)$_m$-C(O)N($R^6$)$_2$, -(alkylene)$_m$-NHC(O)$R^6$ or -(alkylene)$_m$-N($R^6$)$_2$, or $R^{10}$ and $R^{10a}$, together with the common carbon atom to which each are attached, join to form a carbonyl group or a spirocyclic cycloalkyl or heterocycloalkyl group;

$R^{10a}$ is H, alkyl, haloalkyl, hydroxyalkyl, -(alkylene)$_m$-C(O)N($R^6$)$_2$, -(alkylene)$_m$-NHC(O)—$R^6$ or -(alkylene)$_m$-N($R^6$)$_2$;

each occurrence of $R^{11}$ is independently H, alkyl, haloalkyl, hydroxyalkyl, -(alkylene)$_m$-C(O)N($R^6$)$_2$, -(alkylene)$_m$-NHC(O)—$R^6$ or -(alkylene)$_m$-N($R^6$)$_2$, or $R^{11}$ and the ring carbon atom to which it is attached, combine to form a carbonyl group;

each occurrence of $R^{12}$ is independently H, alkyl, -(alkylene)$_m$-aryl, -(alkylene)$_m$-heteroaryl, -(alkylene)$_m$-heterocycloalkyl, —S(O)$_2$$R^7$, haloalkyl, hydroxyalkyl, —C(O)$R^6$ or —C(O)O$R^6$;

Ar is arylene or heteroarylene, wherein the arylene or heteroarylene is joined via any 2 of its adjacent ring carbon atoms, and wherein the arylene or heteroarylene group can be optionally substituted with up to 4 substituents, which may be the same or different, and are independently selected from halo, alkyl, alkoxy, aryloxy, —$NH_2$, —NH-alkyl, —N(alkyl)$_2$, —S$R^6$, —S(O)$R^7$, —S(O)$_2$$R^7$, —C(O)$R^6$, —C(O)O$R^6$, —C(O)N($R^6$)$_2$, —NHC(O)$R^6$, haloalkyl, —CN and $NO_2$, such that when Ar is tetrahydronaphthylene, $R^2$ and $R^3$ are each other than hydrogen;

W is —N($R^{12}$)$_2$—, —S—, —O— or —C($R^5$)$_2$—, wherein when W is —C($R^5$)$_2$—, both $R^5$ groups and the common carbon atom to which they are attached can combine to form a spirocyclic cycloalkyl or heterocycloalkyl group, wherein such a spirocyclic group can be optionally substituted with up to 4 groups, which can be the same or different and are selected from halo, alkyl, alkenyl, alkynyl, haloalkyl, hydroxyalkyl, —O$R^6$, -(alkylene)$_m$-N($R^6$)$_2$, —C(O)O$R^6$, —NHC(O)$R^6$, —C(O)N($R^6$)$_2$, —S(O)$_2$$R^7$, —CN, —OH, —$NO_2$, -(alkylene)$_m$-aryl, -(alkylene)$_m$-cycloalkyl, -(alkylene)$_m$-heteroaryl, -(alkylene)$_m$-heterocycloalkyl and -(alkylene)$_m$-heterocycloalkenyl;

Y is H, halo, alkyl or —CN;

Z is —C($R^8$)— or —N— when the optional and additional bond is absent and Z is —C— when the optional and additional bond is present;

each occurrence of m is independently 0 or 1;

n is an integer ranging from 0 to 2; and p is 0 or 1.

In one aspect, the compounds of Formula (I) (the “Thiazole Derivatives”) can be useful as protein kinase inhibitors.

In another aspect, the Thiazole Derivatives can be useful for treating or preventing a proliferative disorder, an anti-proliferative disorder, inflammation, arthritis, a central nervous system disorder, a cardiovascular disease, alopecia, a neuronal disease, an ischemic injury, a viral infection, a fungal infection, or a disorder related to the activity of a protein kinase (each being a “Condition”).

In another aspect, the present invention provides pharmaceutical compositions comprising an effective amount of at least one Thiazole Derivative and a pharmaceutically acceptable carrier. The compositions can be useful for treating or preventing a Condition in a patient.

In still another aspect, the present invention provides methods for treating pr preventing a Condition in a patient, the method comprising administering to the patient an effective amount of at least one Thiazole Derivative.

In another aspect, the present invention provides methods for treating a cancer in a patient, the method comprising administering to the patient an effective amount of at least one Thiazole Derivative.

In another aspect, the present invention provides methods for treating a cancer in a patient, the method comprising administering to the patient an at least one Thiazole Derivative and at least one additional anticancer agent which is not an Thiazole Derivative, wherein the amounts administered are together effective to treat the cancer.

DETAILED DESCRIPTION OF THE INVENTION

In an embodiment, the present invention provides Thiazole Derivatives of Formula (I) and or pharmaceutically acceptable salts, solvates, esters and prodrugs thereof. The Thiazole Derivatives can be useful for treating or preventing a Condition in a patient,

Definitions and Abbreviations

As used above, and throughout this disclosure, the following terms, unless otherwise indicated, shall be understood to have the following meanings:

“Acyl” means an H—C(O)—, alkyl-C(O)— or cycloalkyl-C(O)—, group in which the various groups are as previously described. The bond to the parent moiety is through the carbonyl. In one embodiment, acyls contain a lower alkyl. Non-limiting examples of suitable acyl groups include formyl, acetyl and propanoyl.

“Alkoxy” means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

“Alkoxycarbonyl” means an alkyl-O—CO— group. Non-limiting examples of suitable alkoxycarbonyl groups include methoxycarbonyl and ethoxycarbonyl. The bond to the parent moiety is through the carbonyl.

“Alkyl” means an aliphatic hydrocarbon group which may be straight or branched and comprising about 1 to about 20 carbon atoms in the chain. In one embodiment, an alkyl group contains from about 1 to about 12 carbon atoms in the chain. In another embodiment, an alkyl group contains from about 1 to about 6 carbon atoms in the chain. Branched means that one or more lower alkyl groups such as methyl, ethyl or propyl, are attached to a linear alkyl chain. Lower alkyl refers to a group having about 1 to about 6 carbon atoms in the chain which may be straight or branched. An alkyl group may be unsubstituted or optionally substituted by one or more substituents which may be the same or different, each substituent being independently selected from the group consisting of halo, alkyl, aryl, cycloalkyl, cyano, hydroxy, alkoxy, —S-alkyl, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl, n-butyl, sec-butyl, isobutyl, t-butyl, n-pentyl, isopentyl, neopentyl, n-hexyl, n-heptyl and n-octyl. In one embodiment, an alkyl group is a “$C_1$-$C_6$ alkyl group,” having from 1 to 6 carbon atoms.

“Alkylaryl” means an alkyl-arylene- group in which the alkyl and arylene are as previously described. In one embodiment, alkylaryis comprise a lower alkyl group. A non-limiting example of a suitable alkylaryl group is tolyl. The bond to the parent moiety is through the arylene group.

"Alkylsulfonyl" means an alkyl-$S(O_2)$— group. In one embodiment, the alkyl moiety of an alkylsulfonyl group is lower alkyl (i.e., $C_1$-$C_6$ alkyl). The bond to the parent moiety is through the sulfonyl moiety.

"Alkylthio" means an alkyl-S— group in which the alkyl group is as previously described. Non-limiting examples of suitable alkylthio groups include methylthio and ethylthio. An alkylthio group is bound to the parent moiety via its sulfur atom.

"Alkenyl" means an aliphatic hydrocarbon group containing at least one carbon-carbon double bond and which may be straight or branched and comprising about 2 to about 15 carbon atoms in the chain. In one embodiment, an alkenyl group has from about 2 to about 12 carbon atoms in the chain; in another embodiment, an alkenyl group has from about 2 to about 6 carbon atoms in the chain. Branched means that one or more lower alkyl groups such as methyl, ethyl or propyl, are attached to a linear alkenyl chain. Lower alkenyl refers to about 2 to about 6 carbon atoms in the chain which may be straight or branched. An alkenyl group may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means an alkyl group, as defined above, wherein one of the alkyl group's hydrogen atoms has been replaced with a bond. Non-limiting examples of alkylene groups include $—CH_2—$, $—CH_2CH_2—$, $—CH_2CH_2CH_2—$, $—CH_2CH_2CH_2CH_2—$, $—CH(CH_3)CH_2CH_2—$, $—CH(CH_3)—$ and $—CH_2CH(CH_3)CH_2—$. In one embodiment, an alkylene group has from 1 to about 6 carbon atoms. In another embodiment, an alkylene group is branched. In another embodiment, an alkylene group is linear.

"Alkenylene" means a difunctional group obtained by removal of a hydrogen from an alkenyl group that is defined above. Non-limiting examples of alkenylene include —CH═CH—, $—C(CH_3)═CH—$, and $—CH═CHCH_2—$, "Alkynyl" means an aliphatic hydrocarbon group containing at least one carbon-carbon triple bond and which may be straight or branched and comprising about 2 to about 15 carbon atoms in the chain. In one embodiment, an alkynyl group has from about 2 to about 12 carbon atoms in the chain; and in another embodiment, an alkynyl group has from about 2 to about 4 carbon atoms in the chain. Branched means that one or more lower alkyl groups such as methyl, ethyl or propyl, are attached to a linear alkynyl chain. Lower alkynyl refers to about 2 to about 6 carbon atoms in the chain which may be straight or branched. Non-limiting examples of suitable alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of alkyl, aryl and cycloalkyl.

"Alkynylalkyl" means an alkynyl-alkyl- group in which the alkynyl and alkyl are as previously described. In one embodiment, alkynylalkyls contain a lower alkynyl and a lower alkyl group. The bond to the parent moiety is through the alkyl. Non-limiting examples of suitable alkynylalkyl groups include propargylmethyl.

"Aralkloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Aralkyl" or "arylalkyl" means an aryl-alkylene- group in which the aryl and alkylene are as previously described. In one embodiment, aralkyls comprise a lower alkylene group. Non-limiting examples of suitable aralkyl groups include benzyl, 2-phenethyl and naphthalenylmethyl. The bond to the parent moiety is through the alkylene group.

"Aralkylthio" means an aralkyl-S— group in which the aralkyl group is as previously described. Non-limiting example of a suitable aralkylthio group is benzylthio. The bond to the parent moiety is through the sulfur.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Arylene," means an aryl group, wherein a hydrogen atom connected to one of the aryl group's ring carbon atoms is replaced with a single bond.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-$S(O_2)$— group. The bond to the parent moiety is through the sulfonyl.

"Arylthio" means an aryl-S— group in which the aryl group is as previously described. Non-limiting examples of suitable arylthio groups include phenylthio and naphthylthio. The bond to the parent moiety is through the sulfur.

"Benzofused cycloalkyl" means a cycloalkyl moiety as defined above which is fused to a benzene ring. Non-limiting examples of a benzofused cycloalkyl are indanyl and tetrahydronaphthylenyl.

"Benzofused cycloalkenyl" means a cycloalkenyl moiety as defined above which is fused to a benzene ring. Non-limiting examples of a benzofused cycloalkyl include indanyl.

"Benzofused heterocyclyl" means a heterocyclyl moiety as defined above which is fused to a benzene ring. Non-limiting examples of a benzofused heterocyclyl include indolinyl and 2,3-dihydrobenzofuran.

"Benzofused heteroaryl" means a heteroaryl moiety as defined above which is fused to a benzene ring. Non-limiting examples of a benzofused heteroaryl are indolyl, indazolyl, benzofuranyl, quinolinyl, isoquinolinyl, benzthiazolyl, indolyl, benzimidazolyl and benzothiophenyl.

"Composition" means a product comprising the specified ingredients in the specified amounts, as well as any product which results, directly or indirectly, from combination of the specified ingredients in the specified amounts.

"Cycloalkyl" means a non-aromatic mono- or multicyclic ring system comprising about 3 to about 10 carbon atoms, preferably about 5 to about 10 carbon atoms. In one embodiment, cycloalkyl rings contain about 5 to about 7 ring atoms.

A cycloalkyl group can be optionally substituted with one or more "ring system substituents" which may be the same or different, and are as defined above. A cycloalkyl group can be optionally fused to an aryl, heteroaryl or heterocycloalkyl ring. A ring carbon atoms of a cycloalkyl group can optionally be double bonded to an oxygen atom to form a carbonyl group and result in a cycloalkanoyl group. Non-limiting examples of suitable monocyclic cycloalkyls include cyclopropyl, cyclopentyl, cyclohexyl, cycloheptyl, cyclopentanoyl, cyclohexanoyl, and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising from 3 to about 10 carbon atoms and having at least one endocyclic carbon-carbon double bond. In one embodiment, a cycloalkenyl group has from about 5 to about 10 ring carbon atoms. In another embodiment, a cycloalkenyl group has from about 5 to about 7 ring carbon atoms. A cycloalkenyl group can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Effective amount" or "therapeutically effective amount" means an amount of Thiazole Derivative and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

"Halo" means —F, —Cl, —Br or —I. In one embodiment, halo refers to —Cl or —Br. In another embodiment, halo refers to —F.

"Haloalkyl" means an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include $—CH_2F$, $—CHF_2$, $—CF_3$, $—CH_2Cl$ and $—CCl_3$.

"Heteroaryl" means an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, that is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl.

The term "heteroarylene," as used herein, refers to a heteroaryl group, wherein a hydrogen atom connected to one of the heteroaryl group's ring atoms is replaced with a single bond.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocyclyl group has from about 5 to about 10 ring atoms. In another embodiment, a heterocyclyl group has 5 or 6 ring atoms. There are no adjacent oxygen and/or sulfur atoms present in the ring system. Any —NH group in a heterocyclyl ring may exist protected such as, for example, as an —N(BOC), —N(Cbz), —N(Tos) group and the like; such protected heterocyclyl groups are considered part of this invention. The term "heterocyclyl" also encompasses a heterocyclyl group, as defined above, that is fused to an aryl (e.g., benzene) or heteroaryl ring. A heterocyclyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocyclyl group may be functionalized as a carbonyl group. An illustrative example of such a heterocyclyl group is pyrrolidonyl:

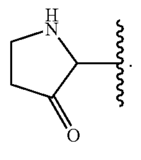

In one embodiment, a heterocyclyl group is unsubstituted. In another embodiment, a heterocyclyl group is a 5-membered heterocyclyl. In another embodiment, a heterocyclyl group is a 6-membered heterocyclyl.

"Heterocyclylalkyl" means a heterocyclyl moiety as defined above linked via an alkyl moiety (defined above) to a parent core. Non-limiting examples of suitable heterocyclylalkyl include piperidinylmethyl, piperazinylmethyl and the like.

"Heterocyclenyl" means a heterocyclyl group, as defined above, wherein the heterocyclyl group contains from 3 to 10 ring atoms, and at least one endocyclic carbon-carbon or carbon-nitrogen double bond. In one embodiment, a heterocyclenyl group has from 5 to 10 ring atoms. In another embodiment, a heterocyclenyl group is monocyclic and has 5 or 6 ring atoms. A heterocyclenyl group can optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

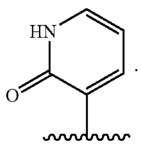 [SMILES: *c1ccc[nH]c1=O]
.

In one embodiment, a heterocyclenyl group is unsubstituted. In another embodiment, a heterocyclenyl group is a 5-membered heterocyclenyl.

"Heterocyclenylalkyl" means a heterocyclenyl moiety as defined above finked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

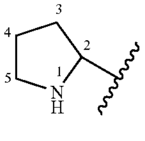

there can be no —OH attached directly to carbons marked 2 and 5.

It should also be noted that tautomeric forms such as, for example, the moieties:

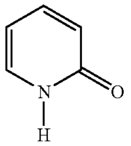
and
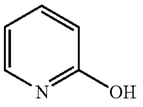

are considered equivalent in certain embodiments of this invention.

"Heteroaralkyl" means a heteroaryl-alkyl- group in which the heteroaryl and alkyl are as previously described. In one embodiment, heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include $—CH_2OH$, $—CH_2CH_2OH$, $—CH_2CH_2CH_2OH$ and $—CH_2CH(OH)CH_3$.

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Ring system substituent" means a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkyl-aryl, -aryl-alkyl, -alkylene-heteroaryl, -alkenylene-heteroaryl, alkynylene-heteroaryl, hydroxy, hydroxyalkyl, haloalkyl, —O-alkyl, —O-haloalkyl, -alkylene-O-alkyl, —O-aryl, aralkoxy, acyl, —C(O)-aryl, halo, nitro, cyano, carboxy, —C(O)O-alkyl, —C(O)O-aryl, —C(O)O-alkelene-aryl, —S(O)-alkyl, $—S(O)_2$-alkyl, —S(O)-aryl, $—S(O)_2$-aryl, —S(O)-heteroaryl, $—S(O)_2$-heteroaryl, —S-alkyl, —S-aryl, —S-heteroaryl, —S-alkylene-aryl, —S-alkylene-heteroaryl, cycloalkyl, heterocyclyl, —O—C(O)-alkyl, —O—C(O)-aryl, —O—C(O)-cycloalkyl, $—C(=N—CN)—NH_2$, $—C(=NH)—NH_2$, —C(=NH)—NH(alkyl), $Y_1Y_2N—$, $Y_1Y_2N$-alkyl-, $Y_1Y_2NC(O)—$ and $Y_1Y_2NSO_2—$, wherein $Y_1$ and $Y_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —$C(CH_3)_2$—, —O-alkylene-O—, and the like which form moieties such as, for example:

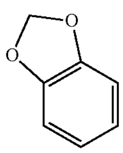 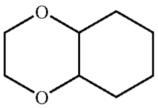 and 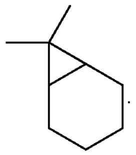.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any carbon atom or heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al., *Protective Groups in Organic Synthesis* (1991), Wiley, New York.

When any variable (e.g., aryl, heterocycle, $R^2$, etc.) occurs more than one time in any constituent or any chemical structure or formula herein, its definition on each occurrence is independent of its definition at every other occurrence.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to provide a Thiazole Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press. 1987.

For example, if a Thiazole Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a Thiazole Derivative contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a Thiazole Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, —$C(OY^2)Y^3$ wherein $Y^2$ is ($C_1$-$C_4$) alkyl and $Y^3$ is ($C_1$-$C_6$)alkyl, carboxy($C_1$-$C_6$)alkyl, amino ($C_1$-$C_4$)alkyl or mono-N- or di-N,N—($C_1$-$C_6$)alkylaminoalkyl, —$C(Y^4)Y^5$ wherein $Y^4$ is H or methyl and $Y^5$ is mono-N- or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder at al, *AAPS PharmSciTech.*, 5(1), article 12 (2004); and A. L. Bingham at al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Thiazole Derivatives can form salts which are also within the scope of this invention. Reference to a Thiazole Derivative herein is understood to include reference to salts thereof, unless otherwise indicated. The term “salt(s)”, as employed herein, denotes acidic salts formed with inorganic and/or organic acids, as well as basic salts formed with inorganic and/or organic bases. In addition, when a Thiazole Derivative contains both a basic moiety, such as, but not limited to a pyridine or imidazole, and an acidic moiety, such as, but not limited to a carboxylic acid, zwitterions (“inner salts”) may be formed and are included within the term “salt(s)” as used herein. Pharmaceutically acceptable (i.e., non-toxic, physiologically acceptable) salts are preferred, although other salts are also useful. Salts of the compounds of the Formula I may be formed, for example, by reacting a Thiazole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Thiazole Derivatives, and salts, solvates, esters and prodrugs thereof, may exist in their tautomeric form (for example, as an amide or imino ether). All such tautomeric forms are contemplated herein as part of the present invention.

The Thiazole Derivatives may contain asymmetric or chiral centers, and, therefore, exist in different stereoisomeric forms. It is intended that all stereoisomeric forms of the Thiazole Derivatives as well as mixtures thereof, including racemic mixtures, form part of the present invention. In addition, the present invention embraces all geometric and positional isomers. For example, if a Thiazole Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Thiazole Derivatives may be atropisomers (e.g., substituted biaryls) and are considered as part of this invention. Enantiomers can also be separated by use of chiral HPLC column.

it is also possible that the Thiazole Derivatives may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a Thiazole Derivative incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms “salt”, “solvate”, “ester”, “prodrug” and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Thiazole Derivatives (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled Thiazole Derivatives can generally be prepared by following procedures analogous to those disclosed in the Schemes and/or in the Examples hereinbelow, by substituting an appropriate isotopically labelled reagent for a non-isotopically labelled reagent.

Polymorphic forms of the Thiazole Derivatives, and of the salts, solvates, esters, prodrugs and stereoisomers of the Thiazole Derivatives, are intended to be included in the present invention.

The following abbreviations are used below and have the following meanings: Boc is tert-butoxycarbonyl, dba is dibenzylideneacetone, DMF is N,N-dimethylformamide, DMSO is dimethylsulfoxide, EtOAc is ethyl acetate, LCMS is liquid chromatography mass spectrometry, MeOH is methanol, NMR is nuclear magnetic resonance, PBS is phosphate buffered saline, SPA is scintillation proximity assay, Tf is triflate, TFA is trifluoroacetic acid and Xantphos is 9,9-Dimethyl-4,5-bis(diphenylphosphino)xanthene.

The Thiazole Derivatives of Formula (I)

The present invention provides Thiazole Derivatives of Formula (I):

(I)

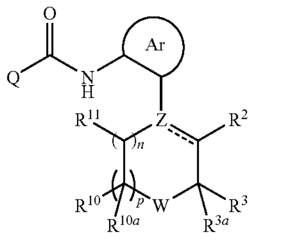

and pharmaceutically acceptable salts, solvates, esters, prodrugs and stereoisomers thereof, wherein the dashed line indicates an optional and additional bond and wherein $R^2$, $R^3$, $R^{3a}$, $R^{10}$, $R^{10a}$, $R^{11}$, Ar, Q, W, Z, n and p are as defined above for formula (I).

In one embodiment, Q is:

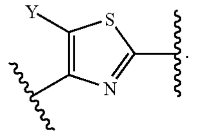

In another embodiment, Q is:

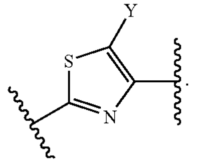

In one embodiment, M is $R^1$.
In another embodiment, M is —C(O)$R^1$.
In still another embodiment, M is —C(S)$R^1$.
In another embodiment, M is —S(O)$R^1$.
In yet another embodiment, M is —$S(O)_2R^1$.
In another embodiment, M is —$S(O)_2NHR^1$,
IN a further embodiment, M is —C(O)O$R^1$.
In one embodiment, M is —C(O)NH$R^1$.
In another embodiment, M is —NHC(O)NH$R^1$.
In another embodiment, M is —NHC(S)NH$R^1$.
In still another embodiment, M is —NHC(O)O$R^1$.
In another embodiment, M is —$NHS(O)_2R^1$.
In yet another embodiment, M is —N($R^1$)(—C(O)$R^1$).
In a further embodiment, M is —$N(R^1)_2$.
In one embodiment, M is $R^1$, —C(O)O$R^1$, —C(O)NH$R^1$, —NHC(O)$R^1$, —C(O)$R^1$ or —NHC(O)NH$R^1$,
In another embodiment, M is H, alkyl, aryl, heteroaryl, phenyl, -alkylene-aryl or heterocycloalkyl.
In another embodiment, M is $R^1$, —C(O)O$R^1$, —C(O)NH$R^1$, —NHC(O)$R^1$, —C(O)$R^1$ or —NHC(O)NH$R^1$, wherein $R^1$ is H, alkyl, aryl, heteroaryl, phenyl, -alkylene-aryl or heterocycloalkyl.
In one embodiment, $R^1$ is H.
In another embodiment, $R^1$ is -aryl, -arylalkyl, -benzofused cycloalkyl, -heteroaryl, -benzofused heteroaryl or -benzofused heterocyclenyl.
In one embodiment, $R^1$ is -alkyl.
In another embodiment, $R^1$ is -methyl.
In another embodiment, $R^1$ is -alkenyl.
In another embodiment, $R^1$ is -alkynyl.
In one embodiment, $R^1$ is -aryl.
In another embodiment, $R^1$ is -alkylene-aryl.
In another embodiment, $R^1$ is -phenyl.
In one embodiment, $R^1$ is -heteroaryl.
In another embodiment, $R^1$ is -alkylene-heteroaryl.
In another embodiment, $R^1$ is -pyrazinyl.
In another embodiment, $R^1$ is -pyrazolyl.
In one embodiment, $R^1$ is:

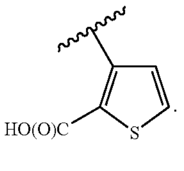

In still another embodiment, $R^1$ is:

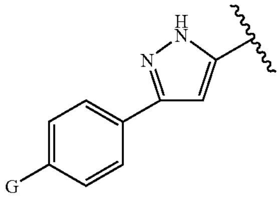

,

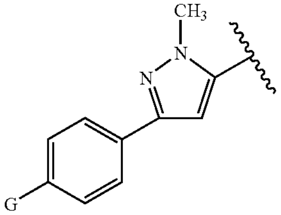

or

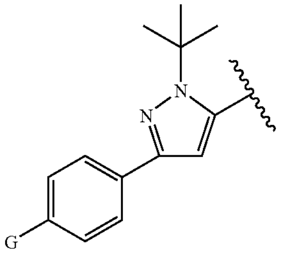

wherein G is H, -halo or alkoxy.

In one embodiment, $R^1$ is -heterocyclyl.

In one embodiment, $R^1$ is -heterocyclenyl.

In one embodiment, $R^1$ is -alkylene-heterocyclyl.

In one embodiment, $R^1$ is -alkylene-heterocyclenyl.

In another embodiment, $R^1$ is -pyrazolinyl.

In one embodiment, $R^1$ is -arylalkyl.

In another embodiment, $R^1$ is -benzyl.

In another embodiment, $R^1$ is -phenethyl.

In one embodiment, $R^1$ is -cycloalkyl.

In another embodiment, $R^1$ is -alkylene-cycloalkyl.

In one embodiment, $R^1$ is -benzofused cycloalkyl.

In another embodiment, $R^1$ is -indanyl.

In one embodiment, $R^1$ is -benzofused heteroaryl.

In another embodiment, $R^1$ is -benzofused heteracyclyl.

In a further embodiment, $R^1$ is -benzofused heterocyclenyl.

In another embodiment, $R^1$ is -indazolyl.

In another embodiment, $R^1$ is:

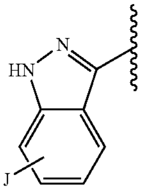

wherein J is H or -halo.

In a further embodiment, $R^1$ is:

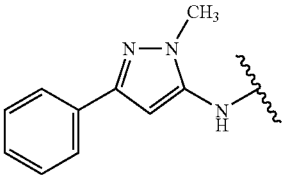

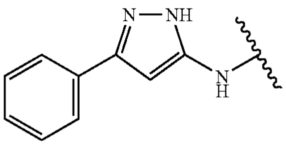

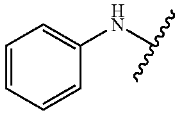

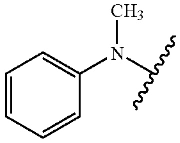

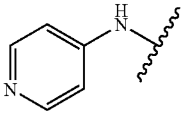

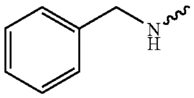

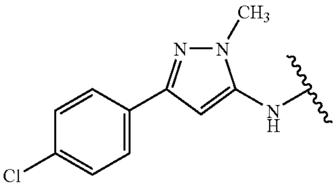

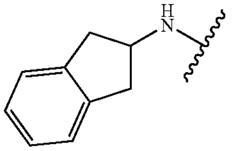

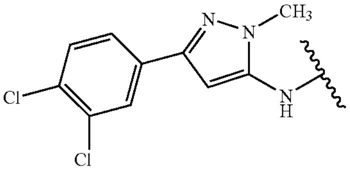

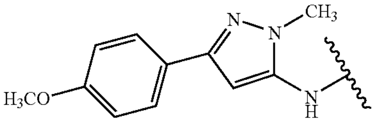

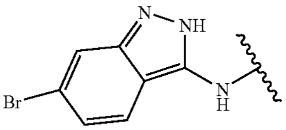

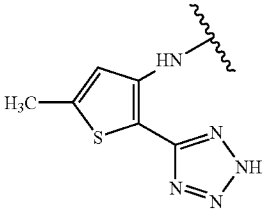

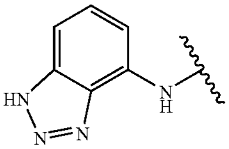

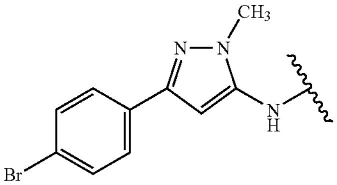

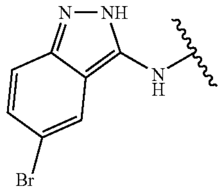

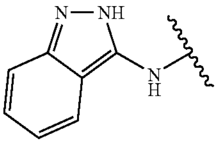

-continued
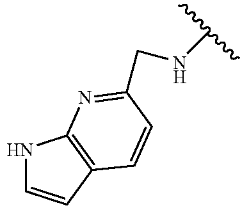 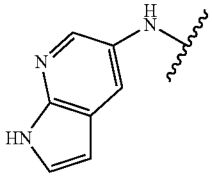
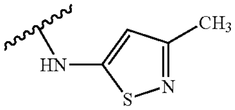 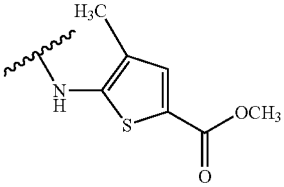
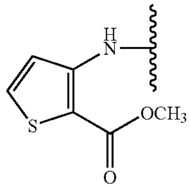 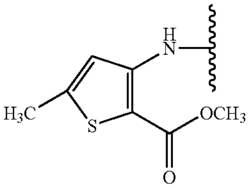
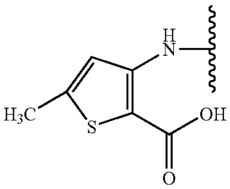 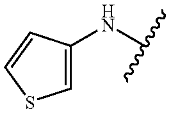
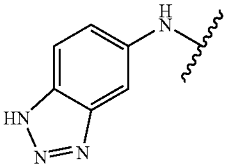
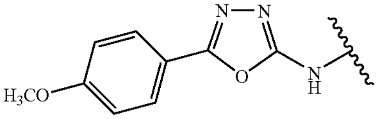 or
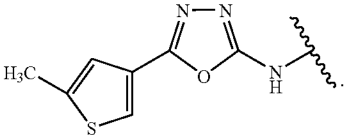.
In another embodiment; $R^1$ is:
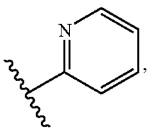, 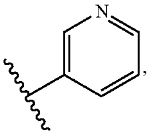, 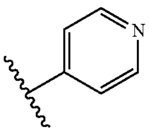,
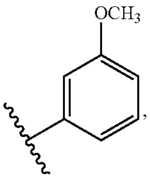, 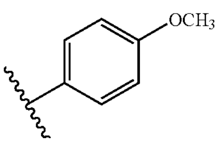, 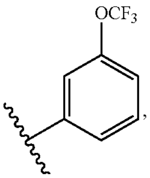,
-continued
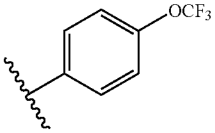, 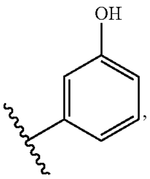,
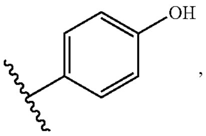, 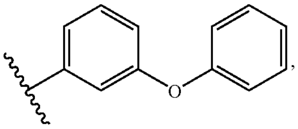,
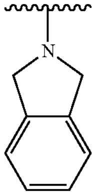, 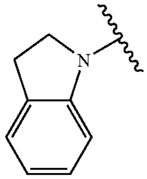, 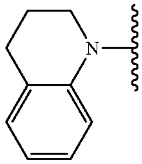,
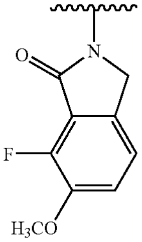, 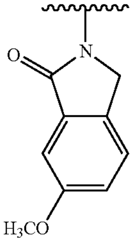, 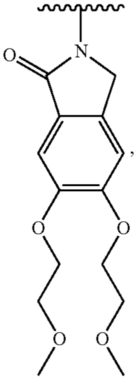,
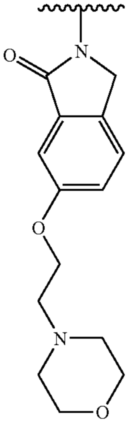, 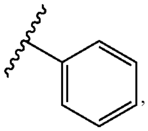, 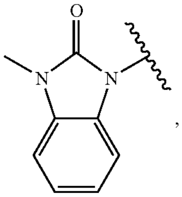,
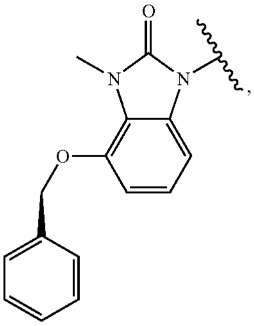, 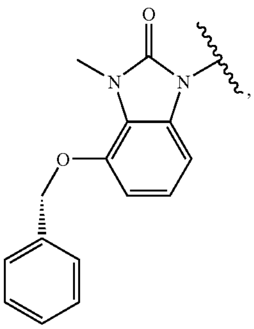, -continued

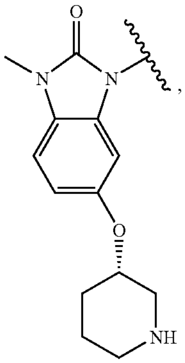,
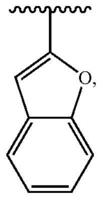
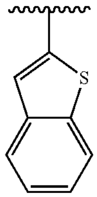
or
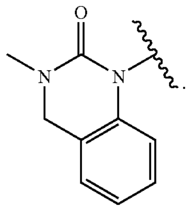.

In one embodiment, $R^2$ is H.

In another embodiment, $R^2$ is alkyl,

In one embodiment, $R^2$ is $—CH_3$.

In another embodiment, $R^2$ is -α-$CH_3$.

In another embodiment, $R^2$ is -β-$CH_3$.

In a further embodiment, $R^2$ is -alkylene-$NH_2$.

In one embodiment, $R^2$ is $—NH_2$.

In another embodiment, $R^2$ is -α-$NH_2$

In another embodiment, $R^2$ is -β-$NH_2$.

In a further embodiment, $R^2$ is -alkylene-$NH_2$.

In yet another embodiment, $R^2$ is $—CH_2NH_2$.

In one embodiment, $R^2$ and the carbon atom to which it is attached, form a carbonyl group.

In one embodiment, $R^3$ is —H.

In another embodiment, $R^{3a}$ is —H,

In another embodiment, $R^3$ and $R^{3a}$ are each —H.

In still another embodiment, $R^3$ is alkyl.

In another embodiment, $R^3$ is haloalkyl.

In yet another embodiment, $R^3$ is hydroxyalkyl.

In one embodiment, $R^3$ is -(alkylene)$_m$-C(O)N($R^8$)$_2$.

In another embodiment, $R^3$ is -(alkylene)$_m$-NHC(O)—$R^9$.

In another embodiment, $R^3$ is -(alkylene)$_m$-N($R^9$)$_2$.

In one embodiment, $R^3$ is $—CH_3$.

In another embodiment, $R^3$ is -α-$CH_3$.

In another embodiment, $R^3$ is -β-$CH_3$.

In one embodiment, $R^3$ is $—NH_2$.

In another embodiment, $R^3$ is -α—$NH_2$.

In another embodiment, $R^3$ is -β-$NH_2$.

In a further embodiment, $R^3$ is -alkylene-$NH_2$.

In yet another embodiment, $R^3$ is $—CH_2NH_2$.

In one embodiment, $R^3$ and $R^{3a}$ and the common carbon atom to which they are attached, join to form a carbonyl group.

In another embodiment, $R^3$ and $R^{3a}$ and the common carbon atom to which they are attached, join to form a cycloalkyl group.

In another embodiment, $R^3$ and $R^{3a}$ and the common carbon atom to which they are attached, join to form a heterocycloalkyl group.

In another embodiment, $R^3$ and $R^{3a}$ and the common carbon atom to which they are attached, join to form one of the following groups:

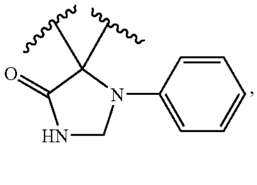,
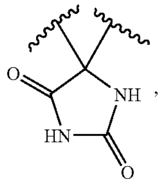,
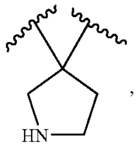,
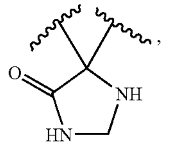,
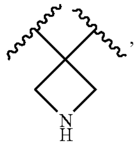,
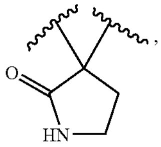,
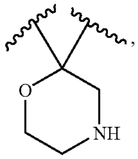,
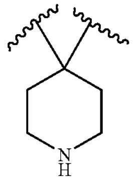
or
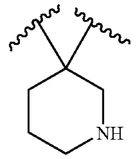

In one embodiment, $R^2$ and $R^{2a}$ are each H.

In another embodiment, $R^2$ is alkyl and $R^{2a}$ is H.

In another embodiment, $R^2$ is H and $R^2$ is alkyl.

In one embodiment, $R^{10}$ is H.

In another embodiment, $R^{10a}$ is H.

In another embodiment, $R^{10}$ and $R^{10a}$ are each H.

In still another embodiment, $R^{10}$ is alkyl.

In another embodiment, $R^{10}$ is haloalkyl.

In yet another embodiment, $R^{10}$ is hydroxyalkyl.

In one embodiment, $R^{10}$ is -(alkylene)$_m$-C(O)N($R^8$)$_2$.

In another embodiment, $R^{10}$ is -(alkylene)$_m$-NHC(O)—$R^9$.

In another embodiment, $R^{10}$ is -(alkylene)$_m$-N(R)$_2$.

In one embodiment, $R^{10}$ is $—CH_3$.

In another embodiment, $R^{10}$ is -α-$CH_3$.

In another embodiment, $R^{10}$ is -β-$CH_3$.

In one embodiment, $R^{10}$ is $—NH_2$.

In another embodiment, $R^{10}$ is -α-$NH_2$.

In another embodiment, $R^{10}$ is -β-$NH_2$.

In a further embodiment, $R^{10}$ is -alkylene-$NH_2$.

In yet another embodiment, $R^{10}$ is $—CH_2NH_2$.

In one embodiment, $R^{10}$ and $R^{10a}$ and the common carbon atom to which they are attached, join to form a carbonyl group.

In another embodiment, $R^{10}$ and $R^{10a}$ and the common carbon atom to which they are attached, join to form a cycloalkyl group.

In another embodiment, $R^{10}$ and $R^{10a}$ and the common carbon atom to which they are attached, join to form a heterocycloalkyl group.

In one embodiment, $R^{11}$ is H.

In another embodiment, $R^{11}$ is alkyl.

In one embodiment, $R^{11}$ is $—CH_3$.

In another embodiment, $R^{11}$ is -α-$CH_3$.

In another embodiment, $R^{11}$ is -β-$CH_3$.

In a further embodiment, $R^{11}$ is -alkylene-$NH_2$.

In one embodiment, $R^{11}$ is $—NH_2$.

In another embodiment, $R^{11}$ is -α-$NH_2$.

In another embodiment, $R^{11}$ is -β-$NH_2$.

In a further embodiment, $R^{11}$ is -alkylene-$NH_2$.

In yet another embodiment, $R^{11}$ is $—CH_2NH_2$.

In another embodiment, $R^{11}$ and the carbon atom to which it is attached, form a carbonyl group.

In one embodiment, $R^2$, $R^3$, $R^{3a}$, $R^{10}$, $R^{10a}$ and $R^{11}$ are each H.

In another embodiment, $R^2$, $R^3$, $R^{10}$, $R^{10a}$ and $R^{11}$ are each H.

In another embodiment, $R^2$, $R^{10}$, $R^{10a}$ and $R^{11}$ are each H.

In still another embodiment, $R^3$, $R^{3a}$, $R^{10}$, $R^{10a}$ and $R^{11}$ are each H.

In one embodiment, Ar is -arylene-.

In another embodiment, Ar is -heteroarylene-.

In another embodiment, Ar is:

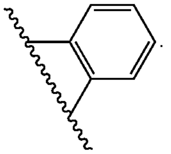

In yet another embodiment, Ar is:

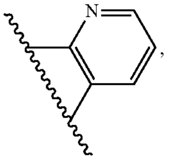

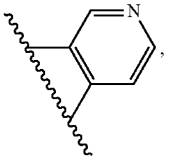

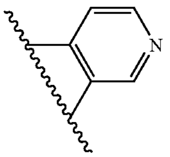

or

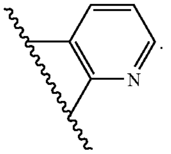

In one embodiment, W is —$C(NH_2)(C(O)NH_2)$—

In another embodiment, W is —$C(NH_2)$(alkyl)-.

In another embodiment, W is —$C(NH_2)(CH_3)$—.

In still another embodiment, W is —$C(NH_2)$(—C(O)NHOH)—.

In one embodiment, W is —CH(—$NC(O)CF_3$)—.

In another embodiment, W is —CH(—$NS(O)_2$alkyl)-.

In still another embodiment, W is —$C(NH_2)$(—C(O)NHOH)—.

In one embodiment, W is —CH(—$CH_2NH_2$)—.

In another embodiment, W is —C(—$C(O)NH_2$)(—NHalkyl)-.

In another embodiment, W is —CH(—$C(O)NH_2$)—.

In still another embodiment, W is —$CH_2$—.

In yet another embodiment, W is —NH—.

In yet another embodiment, W is —$C(R^5)_2$—.

In still another embodiment, W is —CH(OH)—.

In a further embodiment, W is —$CH(NH_2)$—.

In one embodiment, W is —$CH(CH_3)$—.

In another embodiment, W is —CH(—$C(O)CH_3$)—.

In another embodiment, W is —C(OH)(alkyl)-.

In another embodiment, W is —C(OH)(-alkylene-OH)—.

In another embodiment, W is —$N(R^{12})$—.

In another embodiment, W is —O—.

In still another embodiment, W is —S—.

In one embodiment, W is —$C(R^5)_2$— and both $R^5$ groups, together with the common carbon atom to which they are attached, join to form a cycloalkyl group.

In another embodiment, W is —$C(R^5)_2$— and both $R^5$ groups, together with the common carbon atom to which they are attached, join to form a heterocyclyl group.

In another embodiment, W is —$C(R^5)_2$— and both $R^5$ groups, together with the common carbon atom to which they are attached, join to form a group having the formula:

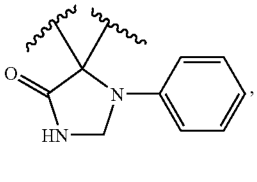

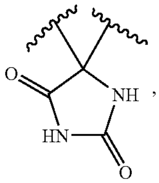

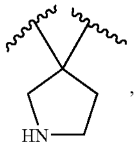

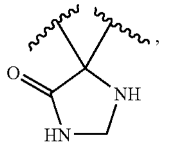

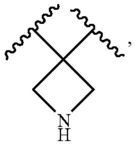

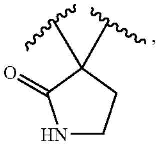

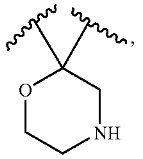

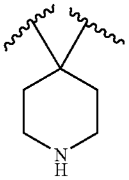

or

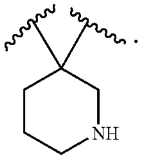

In one embodiment, W is —$C(R^5)_2$— and each $R^5$ group is independently selected from H, -(alkylene)$_m$-$NH_2$, —NH-alkyl, —$N(alkyl)_2$, —$C(O)NH_2$, —OH, —C(O)O-alkyl, 5 or 6 membered heteroaryl or hydroxyalkyl.

In another embodiment, W is —$C(R^5)_2$— and each $R^5$ group is independently selected from H, -(alkylene)$_m$-$NH_2$, —NH-alkyl, —$N(alkyl)_2$ or —$C(O)NH_2$.

In one embodiment, Y is H.

In another embodiment, Y is -halo, -alkyl or —CN.

In another embodiment, Y is methyl.

In one embodiment, Z is —$CR^7$—.

In another embodiment, Z is —CH—.

In still another embodiment, Z is —C(alkyl)-.

In yet another embodiment, Z is —C(OH)—.

In another embodiment, Z is —C(alkoxy)-.

In still another embodiment, Z is —C(—$CF_3$)—.

In a further embodiment. Z is —N—.

In one embodiment, n is 0.

In another embodiment, n is 1.

In another embodiment, n is 2.

In one embodiment, p is 0.

In another embodiment, p is 1.

In one embodiment, n and p are each 1.

In another embodiment, n is 0 and p is 1.

In another embodiment, n is 2 and p is 1.

In one embodiment, n is 0, W is —$CH_2$— and Z is —N—.

In another embodiment, n is 1, W is —$CH_2$— and Z is —N—.

In another embodiment, n is 1, W is —NH— and Z is —N—.

In another embodiment, n is 0, W is —$CH_2$—, Z is —N—, $R^3$ is H and $R^{3a}$ is H.

In still another embodiment, n is 1, W is —$C(NH_2)(C(O)NH_2)$—, Z is —N—, $R^3$ is H and $R^{3a}$ is H.

In yet another embodiment, n is 1, W is —$CH_2$—, Z is —N—, $R^3$ is H and $R^{3a}$ is —$NH_2$.

In another embodiment, n is 1, W is —$CH_2$—, Z is —N—, $R^3$ is H and $R^{3a}$ is -β-$NH_2$.

In a further embodiment, n is 0, W is —$CH_2$—, Z is —N—, $R^3$ is H and $R^{3a}$ is —$NH_2$.

In a further embodiment, n is 0, W is —$CH_2$—, Z is —N—, $R^3$ is H and $R^{3a}$ is -α-$NH_2$.

In another embodiment, n is 1. W is —$CH(NH_2)$—, Z is —N—, $R^3$ is H and $R^{3a}$ is H.

In another embodiment, n is 1, W is —CH(OH)—, Z is —N—, $R^3$ is H and $R^{3a}$ is H.

In still another embodiment, n is 1, W is —$CH(NH_2)$(alkyl)-, Z is —N—, $R^3$ is H and $R^{3a}$ is H.

In one embodiment, Y is H.

In another embodiment, Y is -halo, -alkyl or —CN.

In another embodiment, Y is methyl.

In one embodiment, $R^3$ is H and Z is —N—.

In one embodiment, $R^1$ is -aryl, -arylalkyl, benzofused cycloalkyl, heteroaryl, benzofused heteroaryl or benzofused heterocyclenyl.

In another embodiment, $R^1$ is -phenyl, -benzyl, -phenethyl, -indanyl, piperazinyl or pyrazolyl.

In one embodiment, $R^1$ is -aryl, -arylalkyl, benzofused cycloalkyl, heteroaryl, benzofused heteroaryl or benzofused heterocyclenyl; and $R^2$ is H or alkyl.

In another embodiment, $R^1$ is -aryl, -arylalkyl, benzofused cycloalkyl, heteroaryl, benzofused heteroaryl or benzofused heterocyclenyl;

$R^2$ is H or alkyl; $R^3$ and $R^{3a}$ are each H; and Z is —N—.

In another embodiment, $R^1$ is -aryl, -arylalkyl, benzofused cycloalkyl, heteroaryl, benzofused heteroaryl or benzofused heterocyclenyl; $R^2$ is H or alkyl: $R^3$ and $R^{3a}$ are each H; Z is —N—: and W is NH.

In still another embodiment, $R^1$ is -aryl, -arylalkyl, benzofused cycloalkyl, heteroaryl, benzofused heteroaryl or benzofused heterocyclenyl; $R^2$ is H or alkyl; $R^3$ and $R^{3a}$ are each H; Z is —N—; and W is —$CH(NH_2)$—, —$C(R_4)(NH_2)$— or —CH(OH)—.

In one embodiment, Ar is phenyl, $R^3$ is H and Z is —CH—.

In one embodiment, the group

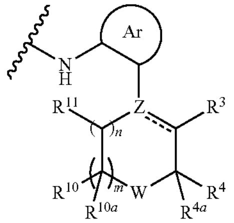

is:

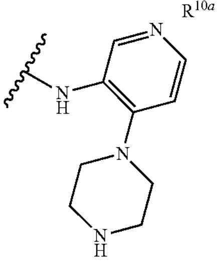

or

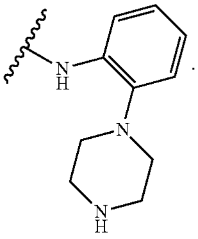

.

In specific embodiments, the group

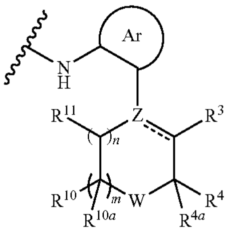

is:

-continued

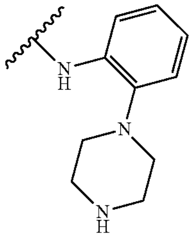

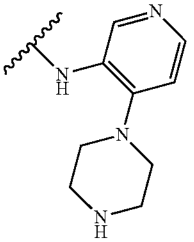

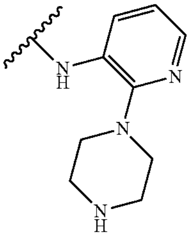

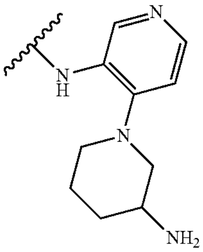

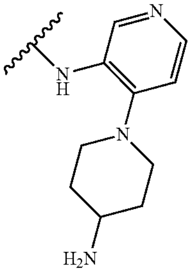

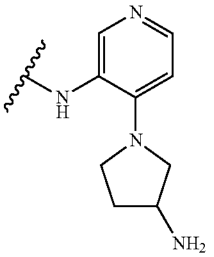

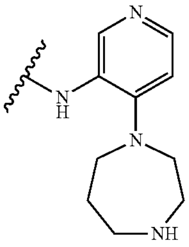

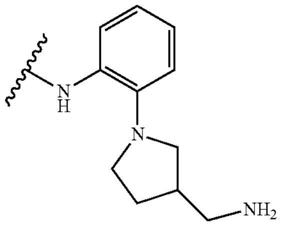

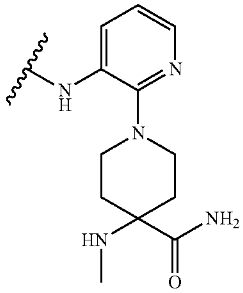

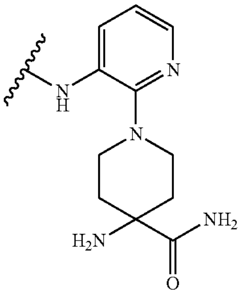

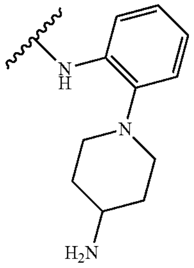

-continued
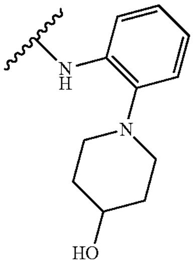
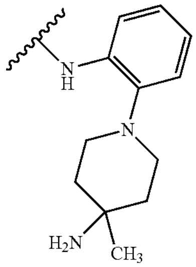
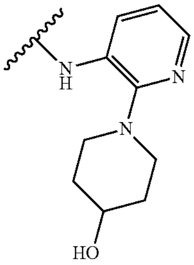
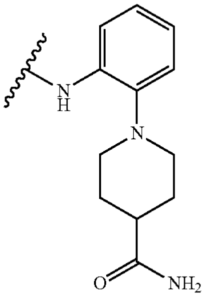
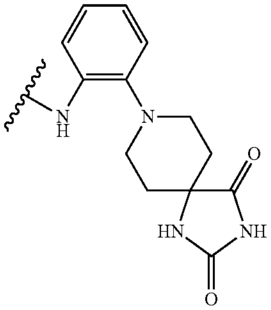
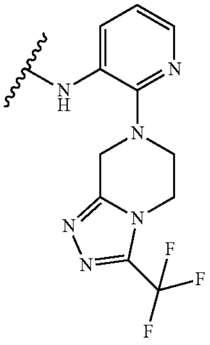
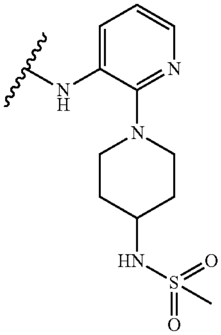
or
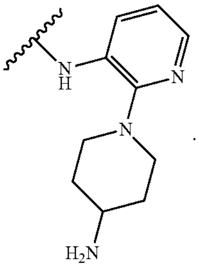
.
In one embodiment, $R^1$ is:
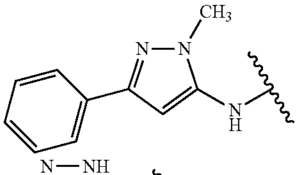
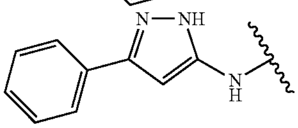
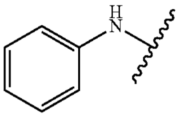
-continued
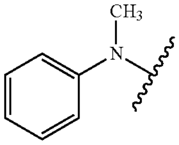
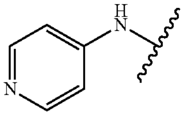
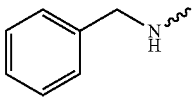
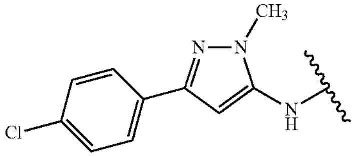
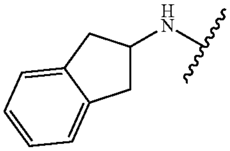
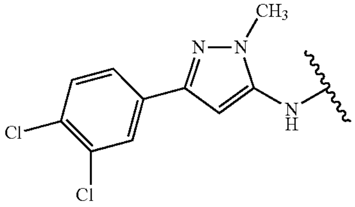
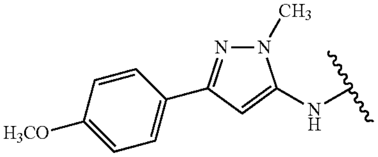
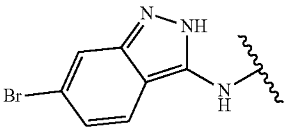
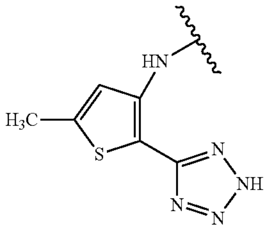
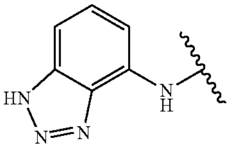
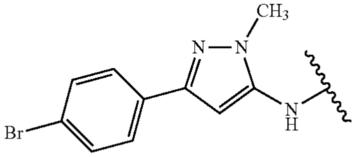
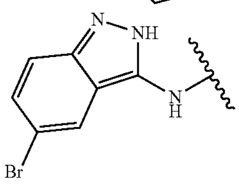
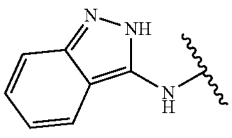
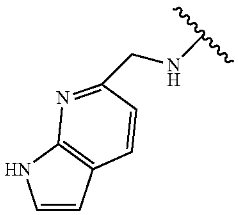
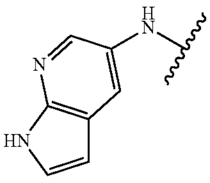

-continued
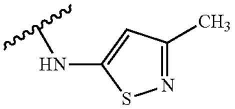
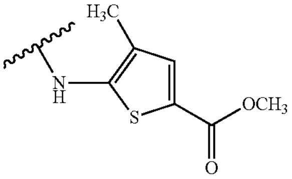
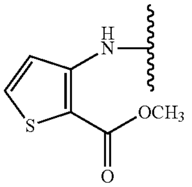
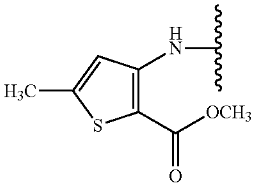
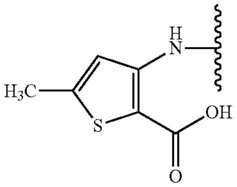
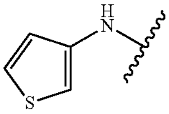
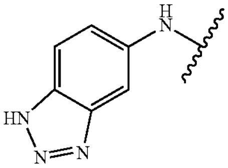
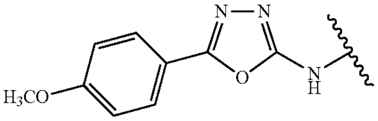
or
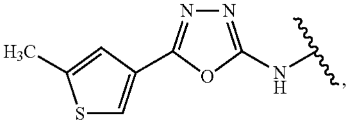
,
and the group
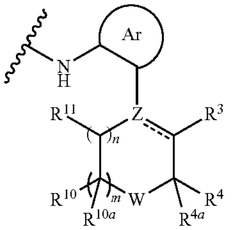
is:
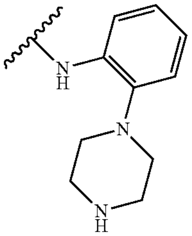
-continued
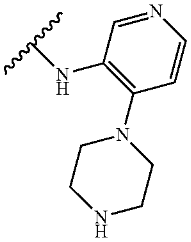
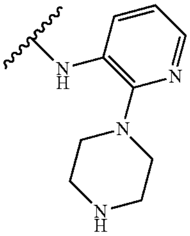
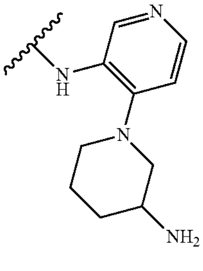
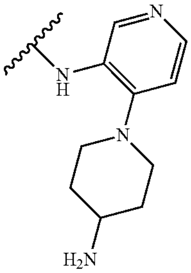
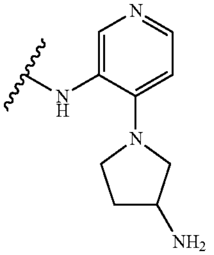
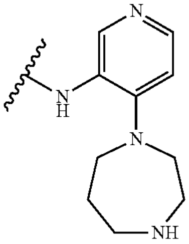
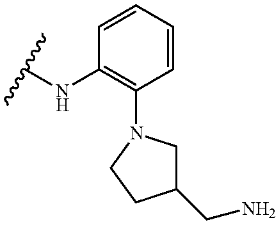
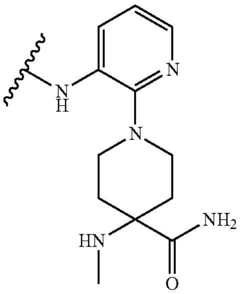
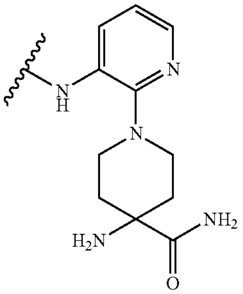
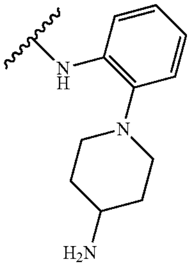
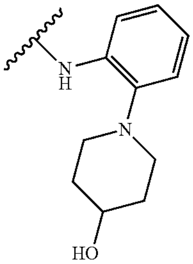
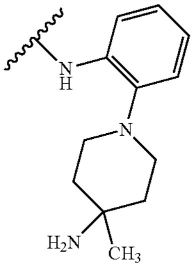

-continued
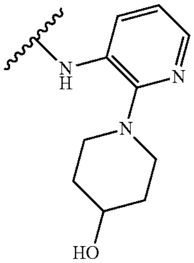 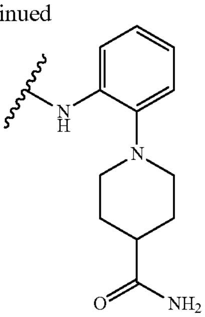
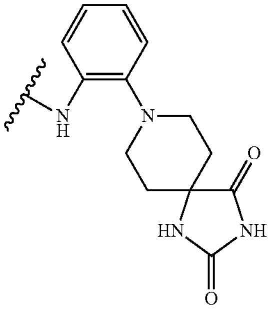 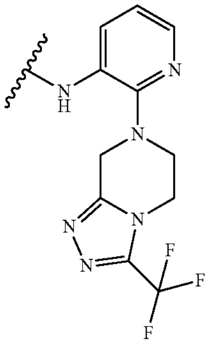
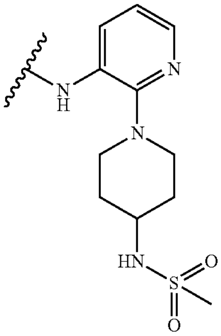 or 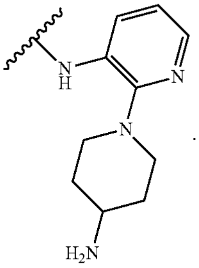.
In one embodiment, $R^1$ is:
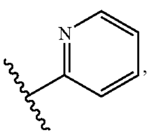, 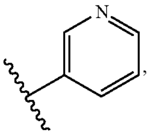, 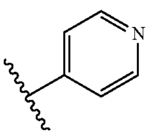,
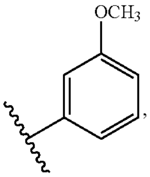, 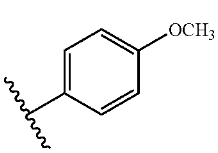, 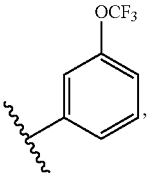,
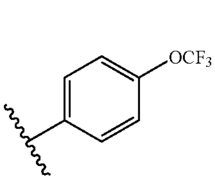, 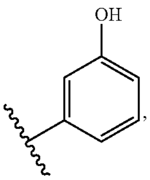,
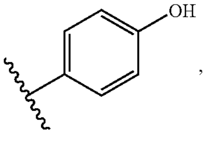, 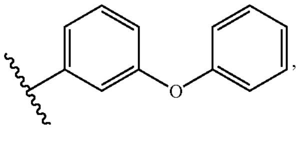,
-continued
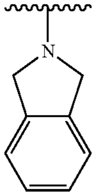, 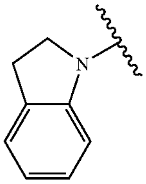, 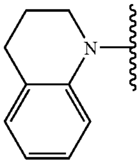,
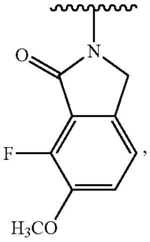, 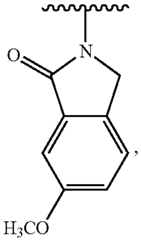, 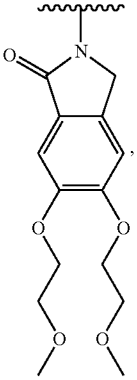,
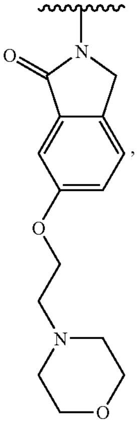, 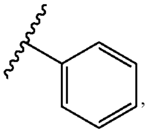, 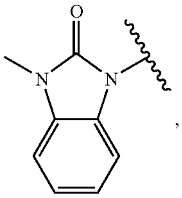,
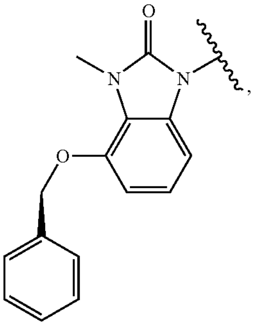, 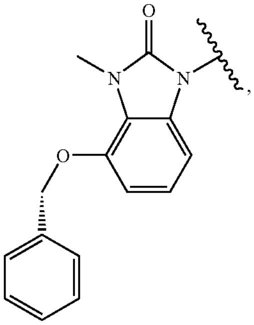,
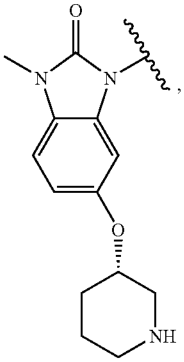, 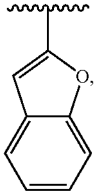, 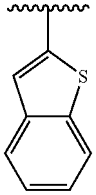 or -continued

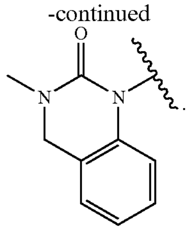.

and the group

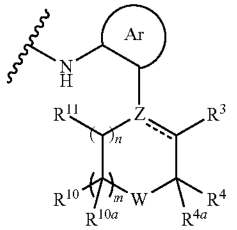 is:

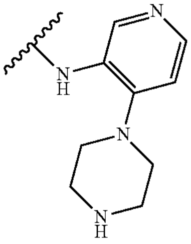 or 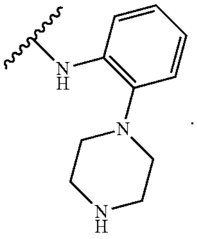.

In one embodiment, the present invention provides a compound of formula (I) or a pharmaceutically acceptable salt, solvate, ester, prodrug or stereoisomer thereof, wherein $R^2$, $R^3$, $R^{3a}$, $R^{10}$, $R^{10a}$, $R^{11}$, Ar, Q, W, Z, n and p are selected independently of each other.

In another embodiment, a compound of formula (I) is in purified form.

In one embodiment, the Thiazole Derivatives have the formula (IA):

(IA)

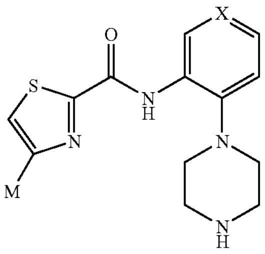

and pharmaceutically acceptable salts, solvates, esters, prodrugs and stereoisomers thereof, wherein M is $R^1$, —C(O)OR$^1$, —C(O)NHR$^1$, —NHC(O)R$^1$, —C(O)R$^1$ or —NHC(O)NHR$^1$; and X is —CH— or —N—.

In one embodiment, the Thiazole Derivatives have the formula (IA) wherein M is H, alkyl, aryl, heteroaryl, phenyl, -alkylene-aryl or heterocycloalkyl.

In another embodiment, the Thiazole Derivatives have the formula (IA) wherein M is $R^1$, —C(O)OR$^1$, —C(O)NHR$^1$, —NHC(O)R$^1$, —C(O)R$^1$ or —NHC(O)NHR$^1$, wherein $R^1$ is H, alkyl, aryl, heteroaryl, phenyl, -alkylene-aryl or heterocycloalkyl.

In another embodiment, the Thiazole Derivatives have the formula (IA) wherein M is $R^1$, —C(O)OR$^1$, —C(O)NHR$^1$, —NHC(O)R$^1$, —C(O)R$^1$ or —NHC(O)NHR$^1$, wherein $R^1$

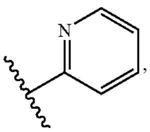, 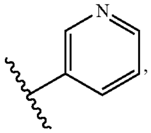, 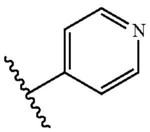,

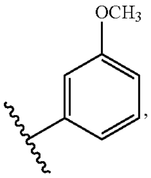, 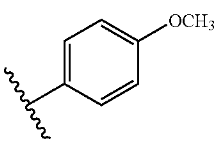, 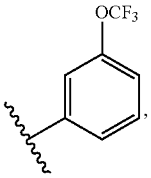,

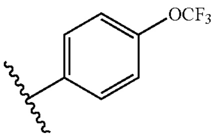, 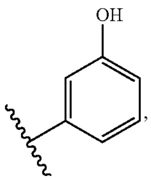,

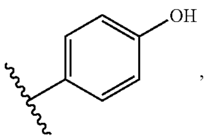, 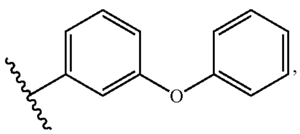,

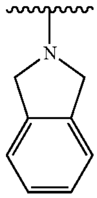, 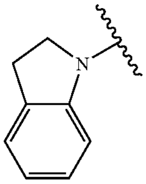, 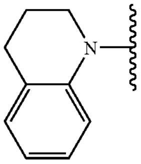,

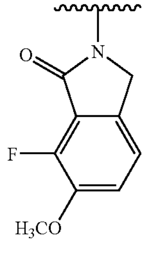, 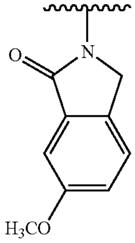, 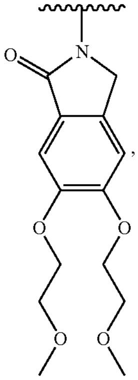,

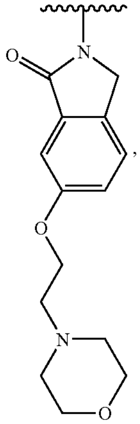, 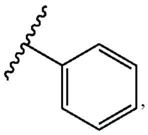, 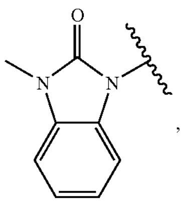,

-continued

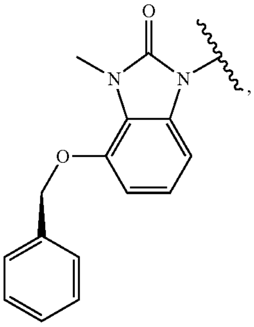

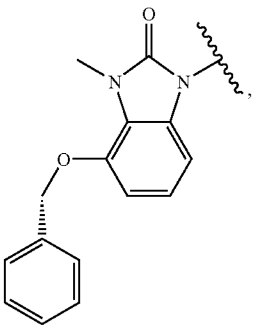

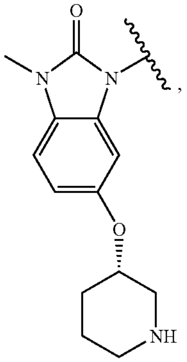

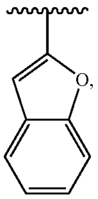

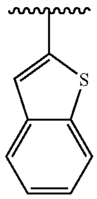

or

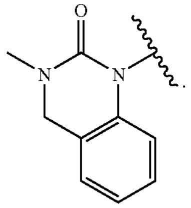

In another embodiment, the Thiazole Derivatives have the formula (IA) wherein X is —CH—.

In still another embodiment, the Thiazole Derivatives have the formula (IA) wherein X is —N—.

In one embodiment, the present invention provides a compound of formula (IA) or a pharmaceutically acceptable salt, solvate, ester, prod rug or stereoisomer thereof, wherein M and X are selected independently of each other.

In another embodiment, a compound of formula (IA) is in purified form.

In one embodiment, the Thiazole Derivatives have the formula (IB):

(IB)

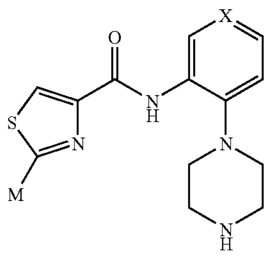

and pharmaceutically acceptable salts, solvates, esters, prodrugs and stereoisomers thereof, wherein M is $R^1$, —C(O)O$R^1$, —C(O)NH$R^1$, —NHC(O)$R^1$, —C(O)$R^1$ or —NHC(O)NH$R^1$; and X is —CH— or —N—.

In one embodiment, the Thiazole Derivatives have the formula (IB) wherein M is H, alkyl, aryl, heteroaryl, phenyl, -alkylene-aryl or heterocycloalkyl.

In another embodiment, the Thiazole Derivatives have the formula (IB) wherein M is $R^1$, —C(O)O$R^1$, —C(O)NH$R^1$, —NHC(O)$R^1$, —C(O)$R^1$ or —NHC(O)NH$R^1$, wherein $R^1$ is H, alkyl, aryl, heteroaryl, phenyl, -alkylene-aryl or heterocycloalkyl.

In another embodiment, the Thiazole Derivatives have the formula (IB) wherein M is $R^1$, —C(O)O$R^1$, —C(O)NH$R^1$, —NHC(O)$R^1$, —C(O)$R^1$ or —NHC(O)NH$R^1$, wherein $R^1$ is:

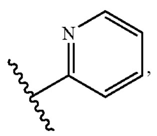

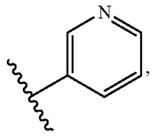

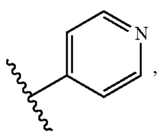

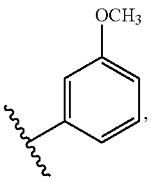

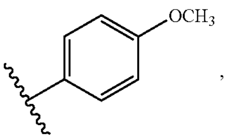

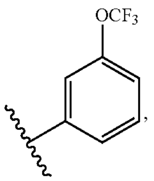

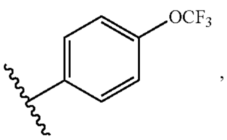

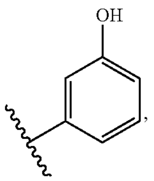

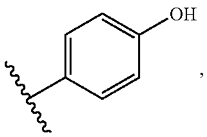

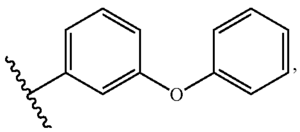

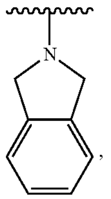

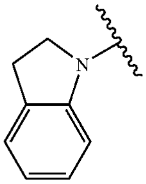

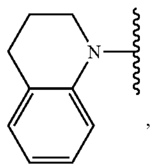

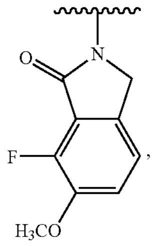

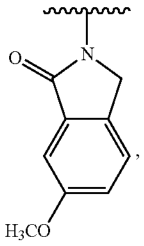

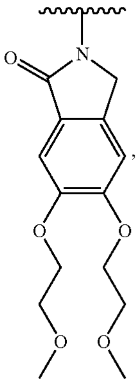

-continued

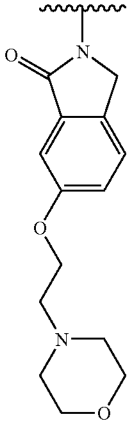,
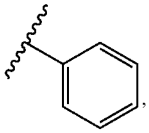,
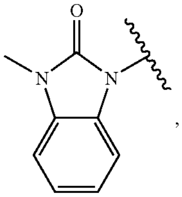,
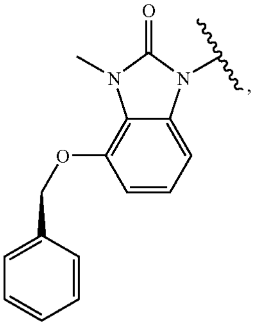,
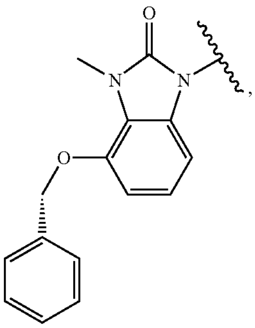,
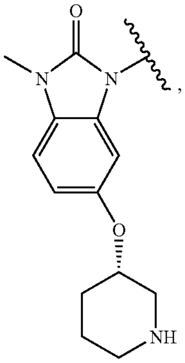,
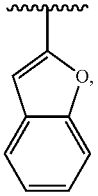
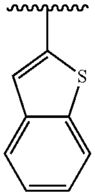 or
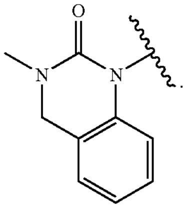.

In another embodiment, the Thiazole Derivatives have the formula (IB) wherein X is —CH—.

In still another embodiment, the Thiazole Derivatives have the formula (IB) wherein X is —N—.

In one embodiment, the present invention provides a compound of formula (IB) or a pharmaceutically acceptable salt, solvate, ester, prodrug or stereoisomer thereof, wherein M and X are selected independently of each other.

In another embodiment, a compound of formula (IB) is in purified form.

Non-limiting, illustrative examples of the Thiazole Derivatives of formula (I) include compounds 1-12, listed below.

| Compound No. | Structure |
|---|---|
| 1 | 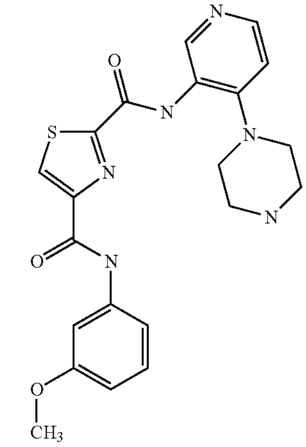 [SMILES: COc1cccc(NC(=O)c2csc(C(=O)Nc3cnccc3N3CCNCC3)n2)c1] |
| 2 | 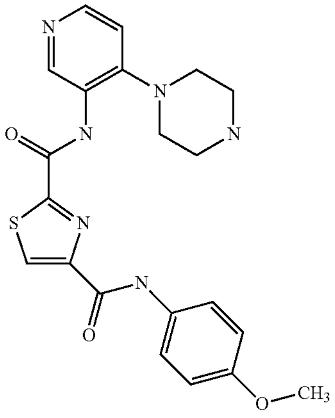 [SMILES: COc1ccc(NC(=O)c2csc(C(=O)Nc3cnccc3N3CCNCC3)n2)cc1] |
| 3 | 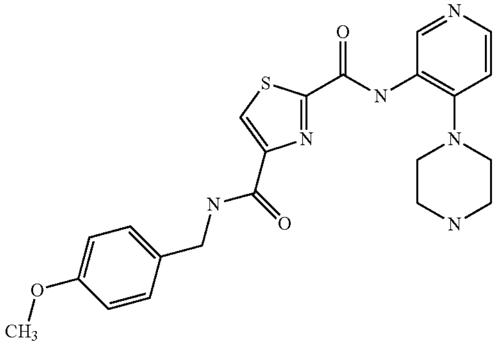 [SMILES: COc1ccc(CNC(=O)c2csc(C(=O)Nc3cnccc3N3CCNCC3)n2)cc1] |

-continued
| Compound No. | Structure |
|---|---|
| 4 | 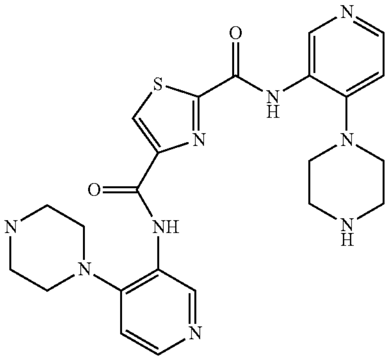 [SMILES: O=C(Nc1cnccc1N1CCNCC1)c1csc(C(=O)Nc2cnccc2N2CCNCC2)n1] |
| 5 | 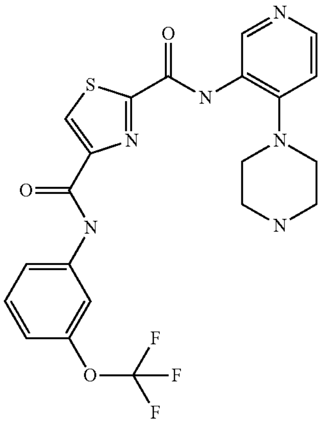 [SMILES: O=C(Nc1cccc(OC(F)(F)F)c1)c1csc(C(=O)Nc2cnccc2N2CCNCC2)n1] |
| 6 | 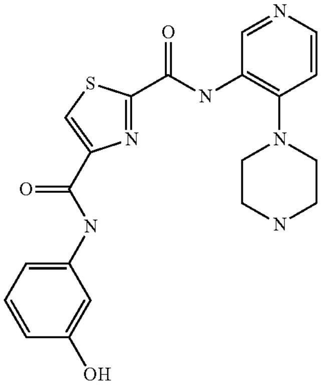 [SMILES: O=C(Nc1cccc(O)c1)c1csc(C(=O)Nc2cnccc2N2CCNCC2)n1] |
| 7 | 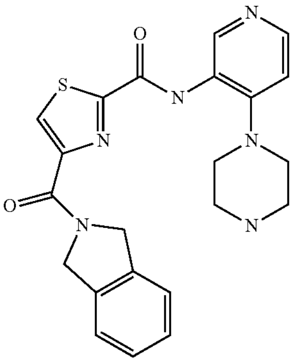 [SMILES: O=C(Nc1cnccc1N1CCNCC1)c1nc(C(=O)N2Cc3ccccc3C2)cs1] |
-continued
| Compound No. | Structure |
|---|---|
| 8 | 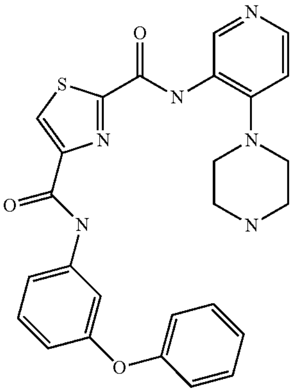 [SMILES: O=C(Nc1cccc(Oc2ccccc2)c1)c1csc(C(=O)Nc2cnccc2N2CCNCC2)n1] |
| 9 | 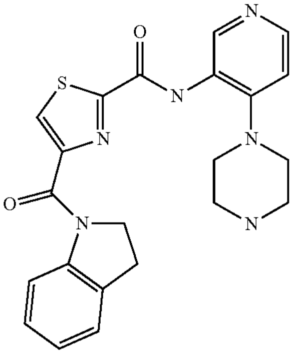 [SMILES: O=C(Nc1cnccc1N1CCNCC1)c1nc(C(=O)N2CCc3ccccc32)cs1] |
| 10 | 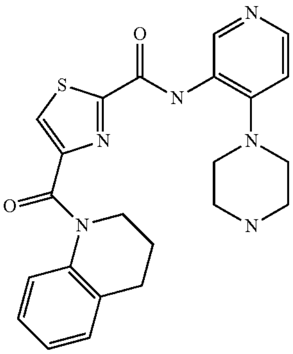 [SMILES: O=C(Nc1cnccc1N1CCNCC1)c1nc(C(=O)N2CCCc3ccccc32)cs1] |
| 11 | 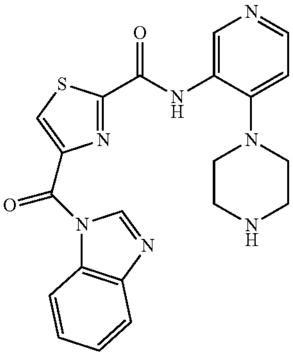 [SMILES: O=C(Nc1cnccc1N1CCNCC1)c1nc(C(=O)n2cnc3ccccc32)cs1] |

-continued

| Compound No. | Structure |
|---|---|
| 12 | 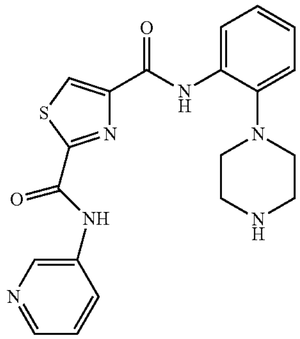 [SMILES: O=C(Nc1ccccc1N1CCNCC1)c1csc(C(=O)Nc2cccnc2)n1] |

and pharmaceutically acceptable salts, solvates, esters, prodrugs and stereoisomers thereof.

Additional, non-limiting illustrative examples of the Thiazole Derivatives of formula (I) include compounds 13-74, depicted in the Examples section herein, and pharmaceutically acceptable salts, solvates, esters, prodrugs and stereoisomers thereof.

Methods for Making the Thiazole Derivatives

Methods useful for making the Thiazole Derivatives of formula (I) are set forth below in Schemes 1-9. Alternative mechanistic pathways and analogous structures will be apparent to those skilled in the art of organic synthesis.

Scheme 1 illustrates a method for making the compounds of formula iv, which is a useful intermediate for making the compounds of formula (I), wherein Z is —N— and W is —N($R^{12}$)—.

Scheme 1

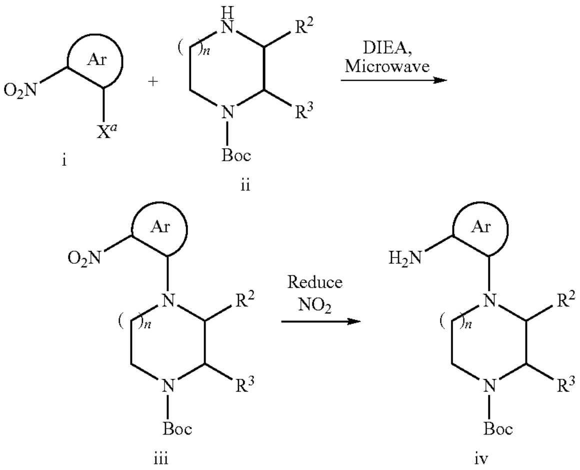

wherein $X^a$ is F or Cl, and $R^2$, $R^3$, Ar and n are as defined above for the compounds of formula (I).

A nitro-substituted aryl or heteroaryl derivative of formula i can be coupled with a piperizine compound of formula II in the presence of diisopropylethylamine (DIEA) using a microwave-assisted process to provide the coupled compound iii. The nitro group of a compound of formula iii can then be reduced using an appropriate method to provide the intermediate amine compounds of formula iv.

Scheme 2 illustrates a method for making the compounds of formula vii, which useful intermediate for making the compounds of formula (I), wherein Z is —N— and W is other than —N($R^2$)—.

Scheme 2

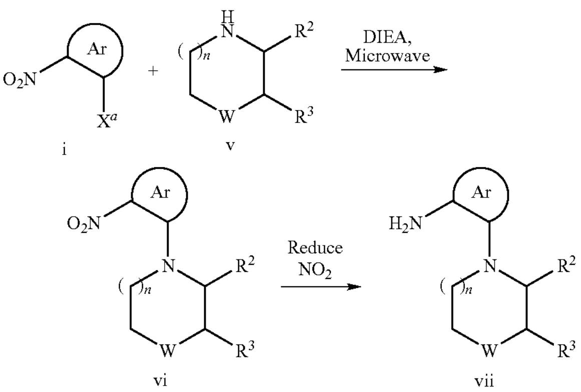

wherein $X^a$ is F or Cl, and $R^2$, $R^3$, W, Ar and n are as defined above for the compounds of formula (I).

A nitro-substituted aryl or heteroaryl derivative of formula i can be coupled with a cyclic amine of formula v to provide the coupled compound vi, using the DIEA coupling method described in Scheme 1. The nitro group of a compound of formula vi can then be reduced using an appropriate method to provide the intermediate amine compounds of formula vii.

Scheme 3 illustrates a method for making the compounds of formula x, which is a useful intermediate for making the compounds of formula (I), wherein Z is carbon and W is —N($R^{12}$)—.

Scheme 3

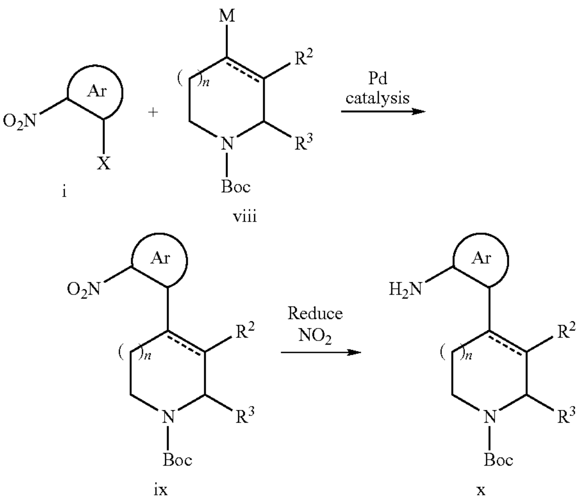

wherein X is Cl, Br or —OTf; M is $B(OH)_2$, ZnX or $SnBu_3$; and $R^2$, $R^3$, Ar and n are as defined above for the compounds of formula (I).

A nitro-substituted aryl or heteroaryl derivative of formula i can be coupled with a piperidine compound of formula viii using a Pd-catalyzed coupling method (e.g., a Suzuki coupling, a Negishi coupling or a Stifle coupling) to provide the coupled compound ix. The nitro group of a compound of formula ix can then be reduced using an appropriate reduction method to provide the intermediate amine compounds of formula x.

Scheme 4 illustrates a method for making the compounds of formula xiv, which is a useful intermediate for making the compounds of formula (I), wherein Z is carbon and W is other than —N($R^{12}$)—.

wherein X is —Cl, —Br or —OTf, M is $B(OH)_2$, ZnX or $SnBu_3$; and $R^2$, $R^3$, W, Ar and n are as defined above for the compounds of formula (I).

A nitro-substituted aryl or heteroaryl derivative of formula i can be coupled with a compound of formula xii to provide a compound of formula xiii, using the Pd coupling method described in Scheme 3. The nitro group of a compound of formula xiii can then be reduced using an appropriate method to provide the intermediate amine compounds of formula xiv.

Scheme 5 illustrates a method for making the compounds of formula (I), wherein W is —NH— and Z is N.

Scheme 5

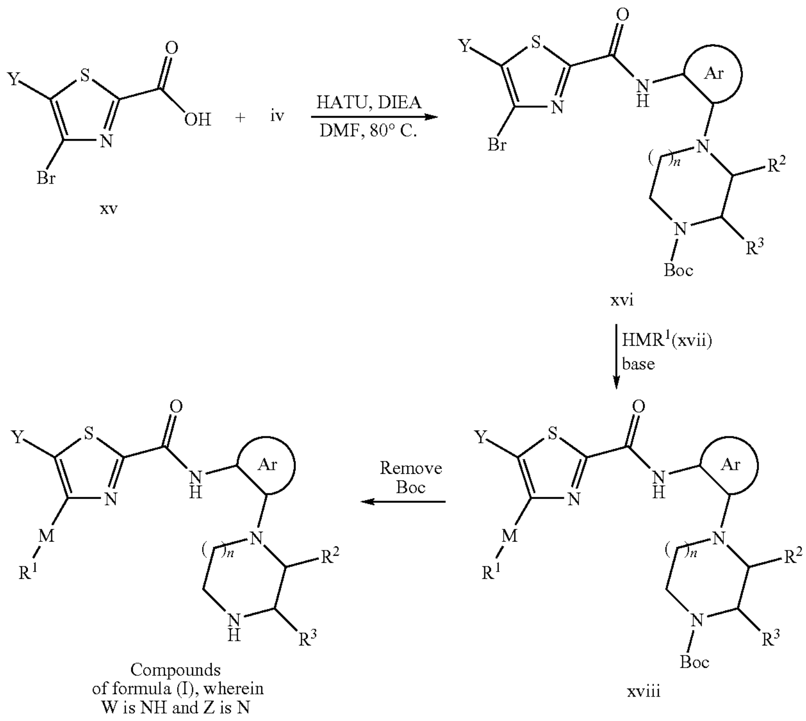

xv xvi xviii

Compounds of formula (I), wherein W is NH and Z is N

Scheme 4

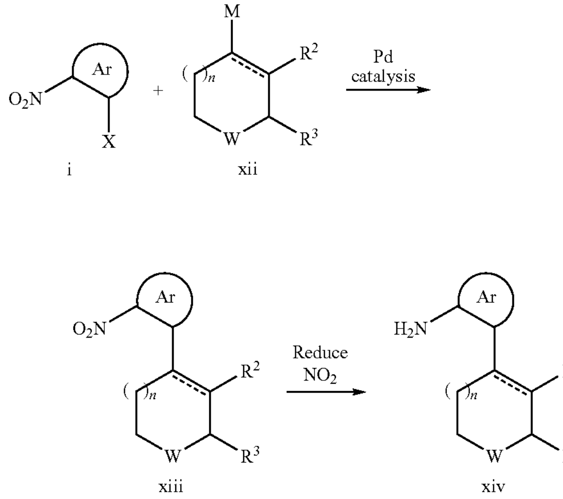

i xii xiii xiv wherein $R^1$, $R^2$, $R^3$, Ar, n and Y are as defined above for the compounds of formula (I).

A 2-bromo-thiazole-4-carboxylic acid compound of formula xv can be coupled with an amine compound of formula iv using 2-(1H-7-azabenzotriazol-1-yl)-1,1,3,3-tetramethyl uranium hexafluorophosphate (HATU) in the presence of N,N-diisopropylethylamine to provide the amido intermediates of formula xvi. A compound of formula xvi can then be coupled with a compound of formula xvii in the optional presence of a non-nucleophilic base to provide the compounds of formula xviii. Removal of the Boc protecting group from a compound of formula xviii using an acid, such as TFA or formic acid, provides the compounds of formula (I), wherein W is —NH— and Z is N.

Scheme 6 illustrates a method for making the compounds of formula (I), wherein W is —C($R^5$)$_2$—; and Z is N.

Scheme 6

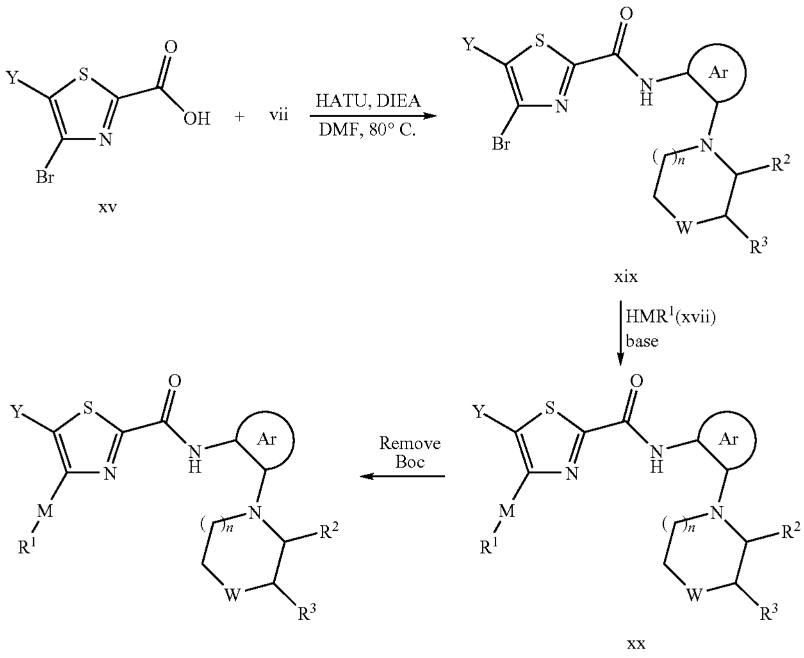

wherein $R^1$, $R^2$, $R^3$, Ar, M, W, Y and n are as defined above for the compounds of formula (I).

Using the method described in Scheme 5 and substituting intermediate amine compound vii for intermediate amine compound Iv, the compounds of formula (I) can be prepared, wherein W is —$C(R^5)_2$—: and Z is N.

Scheme 7 illustrates a method for making the compounds of formula (I), wherein W is —NH— and Z is carbon.

Scheme 7

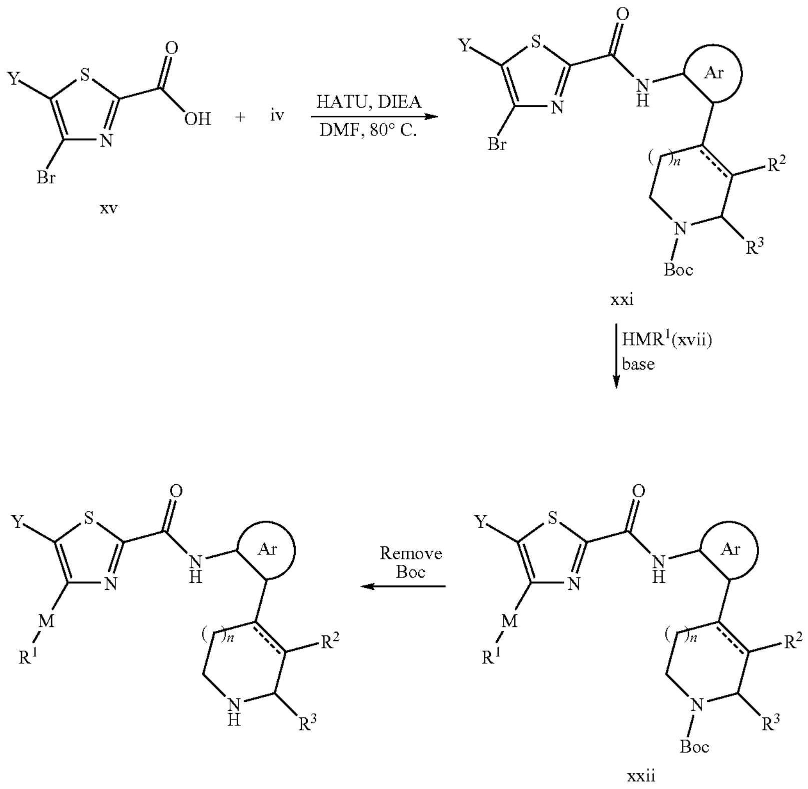

wherein $R^1$, $R^2$, $R^3$, Ar, M, Y and n are as defined above for the compounds of formula (I).

Using the method described in Scheme 5 and substituting intermediate amine compound x for intermediate amine compound iv, the compounds of formula (I) can be prepared, wherein W is —NH— and Z is carbon.

Scheme 8 illustrates a method for making the compounds of formula (I), wherein W is —$C(R^5)_2$—; and Z is carbon.

Scheme 8

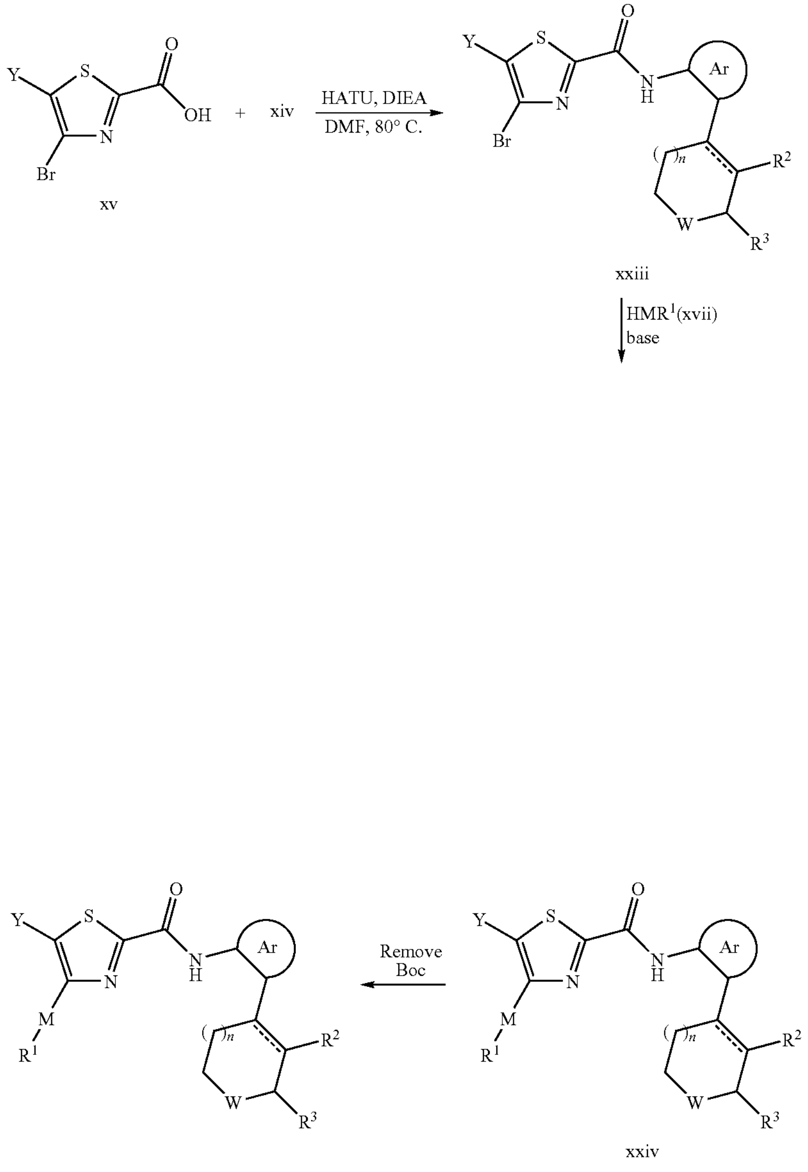

wherein $R^1$, $R^2$, $R^3$, Ar, M, Y and n are as defined above for the compounds of formula (I).

Using the method described in Scheme 5 and substituting intermediate amine compound xiv for intermediate amine compound vii, the compounds of formula (I) can be prepared, wherein W—$C(R^5)_2$—; and Z is carbon.

Scheme 9 illustrates methods useful for making 2-substituted-thiazole-5-carboxylic acid compounds which are useful intermediates for making the compounds of formula (I), wherein M is $R^1$.

Scheme 9

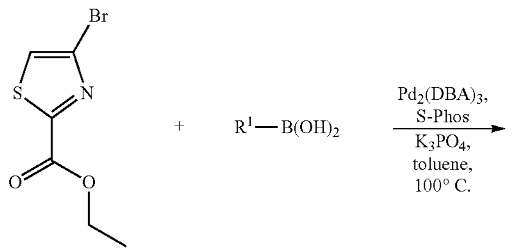

xxv xxvi

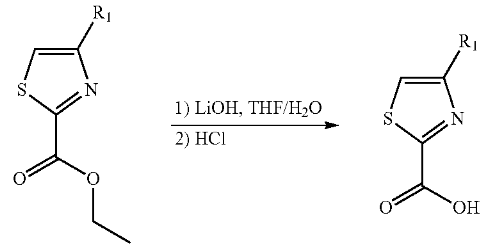

xxvii xxviii

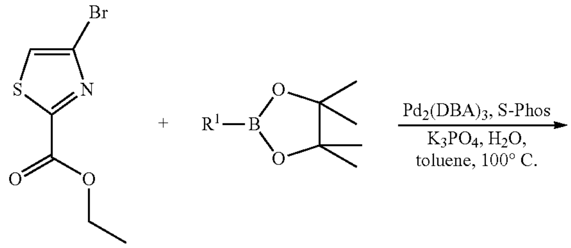

xxv xxix

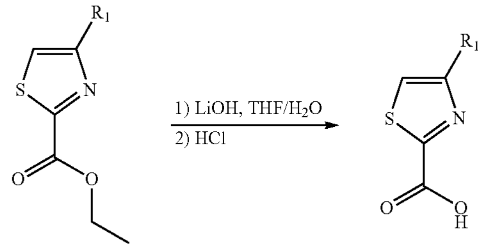

xxx xxxi

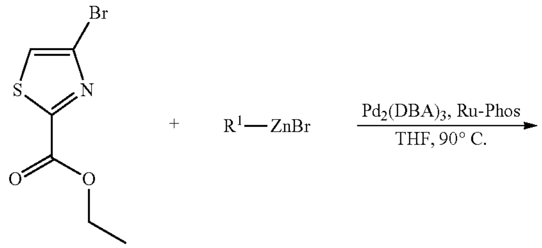

xxv xxxii

-continued

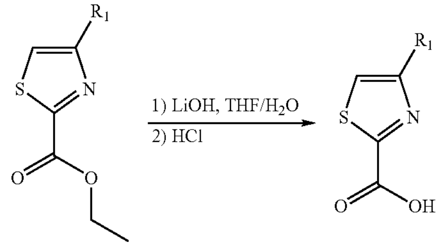

xxxiii xxxiv wherein $R^1$ is as defined above for the compounds of formula (I).

2-Bromothiazole-5-carboxylic acid ethyl ester (xxv) can be reacted with (i) a boronic acid compound of formula xxvi, (ii) a boronic pinacol ester compound of formula xxix, or (iii) a zinc bromide compound of formula xxxii using appropriate palladium coupling conditions to make a 2-substituted thiazole ester intermediate of formula xxvii. The resulting compounds of formula xxvii, xxx or xxxiii can then be hydrolyzed using LiOH, for example, to provide the 2-substituted thiazole-5-carboxylic acid compounds of formula xxviii, xxxi or xxxiv. The compounds of formula xxviii, xxxi or xxxiv can then be converted to the compounds of formula (I) wherein M is $R^1$ using the methods set forth in Examples 5-8 above.

EXAMPLES

General Methods

Solvents, reagents, and intermediates that are commercially available were used as received. Reagents and intermediates that are not commercially available were prepared in the manner as described below. $^1H$ NMR spectra were obtained on a Varian AS-400 (400 MHz) and are reported as ppm down field from $Me_4Si$ with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min—stop. MS data were obtained using Agilent Technologies LC/MSD SL or 1100 series LC/MSD mass spectrometer. Final compounds were purified using PrepLC using a Varian Pursuit XRs C18 10 μm 250×21.2 mm column and an eluent mixture of mobile phase A and B. The mobile phase A is composed of 0.1% TFA in $H_2O$ and the mobile phase B is composed of $CH_3CN$ (95%)/$H_2O$ (5%)/TFA (0.1%). The mixture of mobile phase A and B was eluted through the column at a flow rate of 20 mL/min at room temperature. The purity of all the final discrete compounds was checked by LCMS using a Higgins Haisil HL C18 5 μm 150×4.6 mm column and an eluent mixture of mobile phase A and B, wherein mobile phase A is composed of 0.1% TFA in $H_2O$ and the mobile phase B is composed of $CH_3CN$ (95%)/$H_2O$ (5%)/TFA (0.1%). The column was eluted at a flow rate of 3 mL/min at a temperature of 60° C. Intermediate compounds were characterized by LCMS using a Higgins Haisil HL C18 5 μm 50×4.6 mm column and an eluent mixture of mobile phase A and B, wherein mobile phase A is composed of 0.1% TFA in $H_2O$ and the mobile phase B is composed of $CH_3CN$ (95%)/$H_2O$ (5%)/TFA (0.1%). The column was eluted at a flow rate of 3 mL/min at a column temperature of 60° C.

Example 1

Preparation of Compound 1A

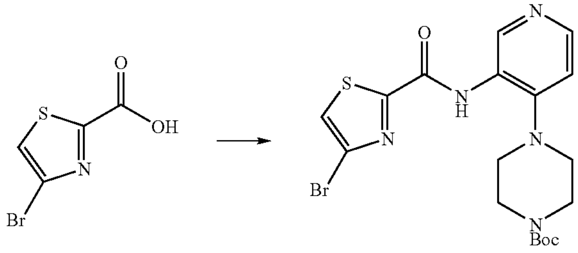

1A

Compound 1A was prepared as described in *J. Fluorine Chemistry,* 55:173-177 (1991).

Using the method described above, the following intermediate compounds were made:

| Compound No. | Structure | LCMS $MH^+$ m/z | HPLC MS $t_R$ |
|---|---|---|---|
| 1B | 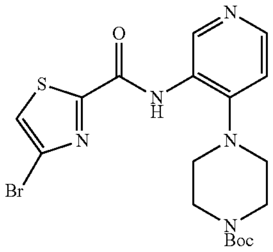 [SMILES: CC(C)(C)OC(=O)N1CCN(c2ccncc2NC(=O)c2nc(Br)cs2)CC1] | 470.06 | 1.34 |
| 1C | 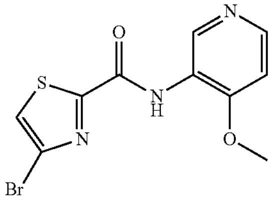 [SMILES: COc1ccncc1NC(=O)c1nc(Br)cs1] | 316.02 | 0.89 |

Example 2

Preparation of Compound 13

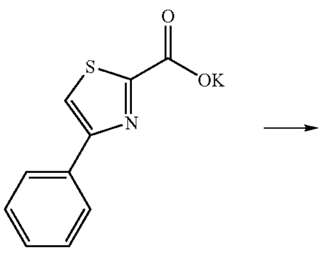

-continued

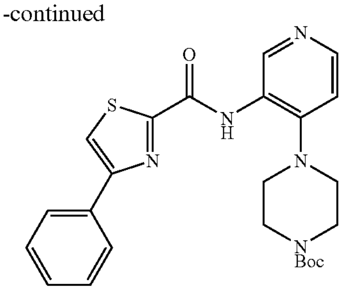

13

To a solution of the potassium salt of 4-phenyl-thiazole-2-carboxylic acid (50 mg, 0.19 mmol) in DMF (4 mL) was added 4-(3-amino-pyridin-4-yl)-piperazine-1-carboxylic acid tert-butyl ester (64 mg, 0.23 mmol), HATU (87 mg, 0.23 mmol) and diisopropylethylamine (0.57 mmol). The resulting reaction was allowed to stir at room temperature for about 15 hours, then concentrated in vacuo The residue obtained was purified using Prep-HPLC (Varian Persue XRS 10 micron, 21.2x250 column with water-acetonitrile, 0.1% trifluoroacetic acid, 0-95% as eluent and a run time of 40 minutes) to provide compound 13 ($MH^+$ m/z 466.20 MS Rt: 3.72 Calculated MW: 465.18)

Example 3

Preparation of Compound 14

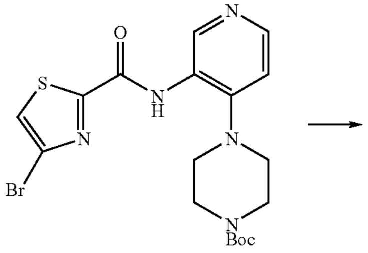

1A

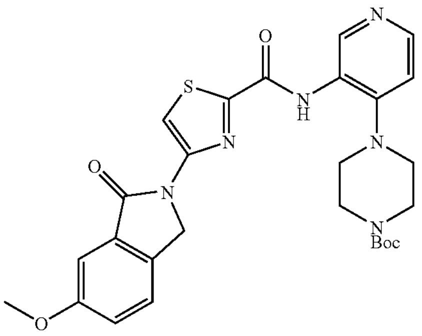

14

To a solution of compound 1A (80 mg, 0.17 mmol) in dioxane (3 mL) was added 6-methoxy-2,3-dihydro-isoindol-1-one (42 mg, 0.26 mmol), potassium phosphate (109 mg, 0.513 mmol), tris(dibenzylideneacetone)dipalladium(0) (15.7 mg, 0.02 mmol) and xantphos (19.8 mg, 0.03 mmol). The resulting reaction was heated to 85° C. and allowed to stir at this temperature for 16 hours. The resulting suspension was passed through a filter to remove insoluble solid and the filtrate was concentrated in vacuo. The residue obtained was purified using Prep-HPLC (Varian Persue XRS 10 micron, 21.2×250 column with water-acetonitrile, 0.1% trifluoroacetic acid, 0-95% as eluent and a run time of 40 minutes) to provide compound 3A with $MH^+$ m/z of 551.30 having retention time of 3.47 min Using this method and the appropriate reactants, the following compounds of the present invention were made:

| Compound No. | Structure | LCMS $MH^+$ m/z | HPLC MS $t_R$ |
|---|---|---|---|
| 15 | 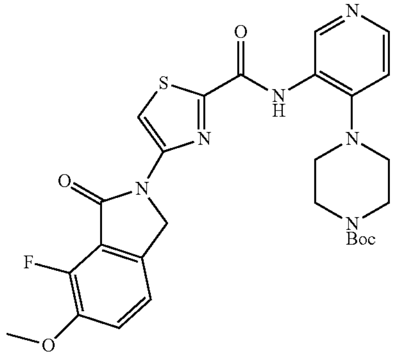 [SMILES: COc1ccc2c(c1F)C(=O)N(c1csc(C(=O)Nc3cnccc3N3CCN(C(=O)OC(C)(C)C)CC3)n1)C2] | 569.29 | 3.44 |
| 16 | 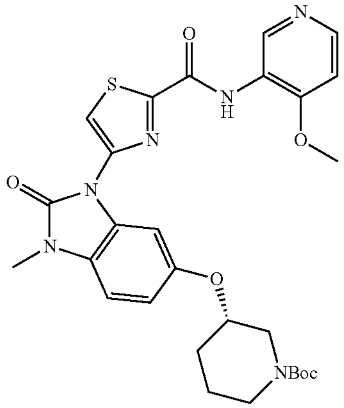 [SMILES: COc1ccncc1NC(=O)c1nc(-n2c(=O)n(C)c3ccc(O[C@H]4CCCN(C(=O)OC(C)(C)C)C4)cc32)cs1] | 581.32 | 3.62 |
| 17 | 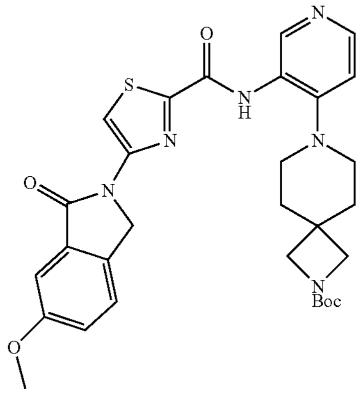 [SMILES: COc1ccc2c(c1)C(=O)N(c1csc(C(=O)Nc3cnccc3N3CCC4(CC3)CN(C(=O)OC(C)(C)C)C4)n1)C2] | 591.41 | 3.75 |

-continued
| Compound No. | Structure | LCMS MH+ m/z | HPLC MS $t_R$ |
|---|---|---|---|
| 18 | 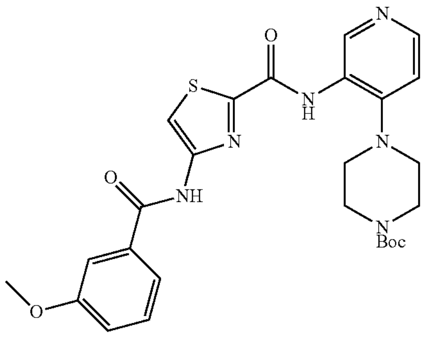 [SMILES: COc1cccc(C(=O)Nc2csc(C(=O)Nc3cnccc3N3CCN(C(=O)OC(C)(C)C)CC3)n2)c1] | 539.10 | 3.50 |
| 19 | 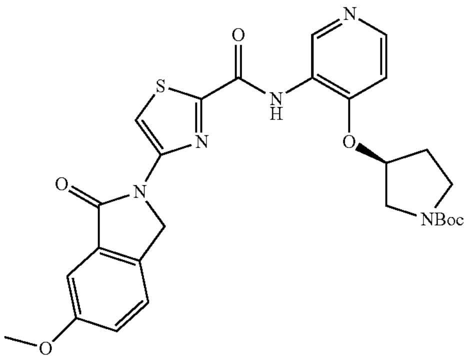 [SMILES: COc1ccc2c(c1)C(=O)N(c1csc(C(=O)Nc3cnccc3O[C@H]3CCN(C(=O)OC(C)(C)C)C3)n1)C2] | 552.10 | 3.65 |
| 20 | 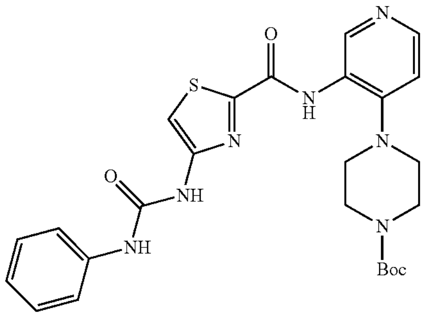 [SMILES: CC(C)(C)OC(=O)N1CCN(c2ccncc2NC(=O)c2nc(NC(=O)Nc3ccccc3)cs2)CC1] | 524.10 | 3.25 |
| 21 | 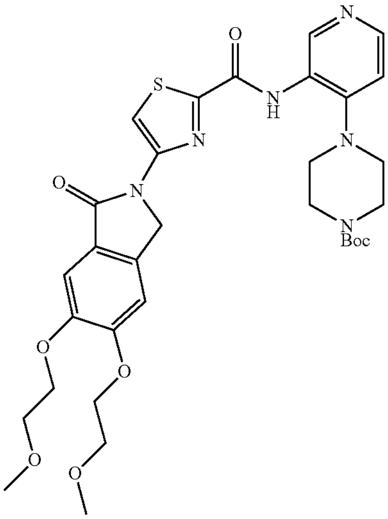 [SMILES: COCCOc1cc2c(cc1OCCOC)C(=O)N(c1csc(C(=O)Nc3cnccc3N3CCN(C(=O)OC(C)(C)C)CC3)n1)C2] | 669.10 | 3.10 |

-continued
| Compound No. | Structure | LCMS MH+ m/z | HPLC MS $t_R$ |
|---|---|---|---|
| 22 | 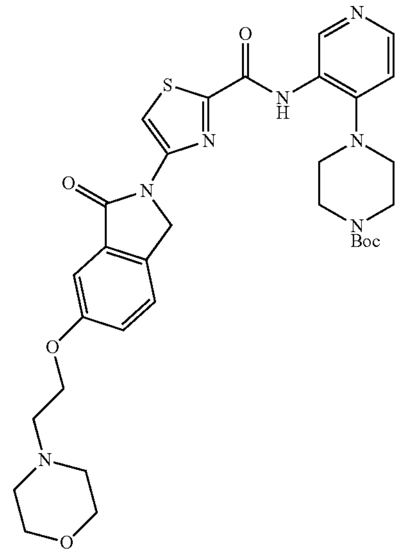 [SMILES: CC(C)(C)OC(=O)N1CCN(c2ccncc2NC(=O)c2nc(N3Cc4ccc(OCCN5CCOCC5)cc4C3=O)cs2)CC1] | 650.10 | 2.75 |
| 23 | 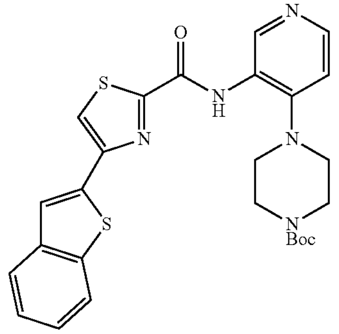 [SMILES: CC(C)(C)OC(=O)N1CCN(c2ccncc2NC(=O)c2nc(-c3cc4ccccc4s3)cs2)CC1] | 522.20 | 3.80 |
| 24 | 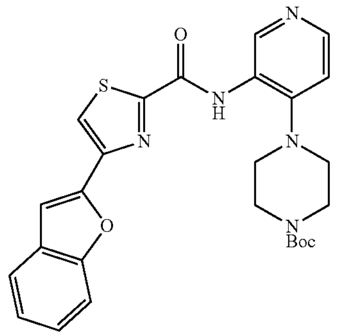 [SMILES: CC(C)(C)OC(=O)N1CCN(c2ccncc2NC(=O)c2nc(-c3cc4ccccc4o3)cs2)CC1] | 506.1 | 3.50 |

Example 4

Preparation of Compound 25

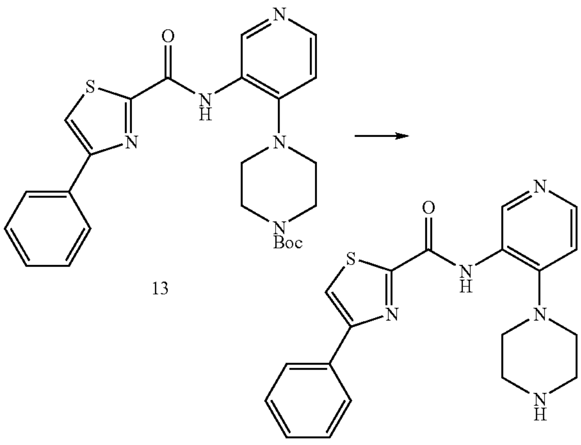

13

25

To solution of compound 13 (5 mg) in dichloromethane was added a solution of 4N HCl and dioxane (1 mL) and the resulting reaction was stirred at room temperature for 20 minutes. The reaction mixture was concentrated in vacuo and the residue obtained was redissolved in water-acetonitrile (1:1, 2 mL) lyophilized to provide compound 25 as off-white powder with MH m/z of 366.05 and a retention time of 1.55 minutes.

Using this method and the appropriate reactants, the following compounds of the present invention were made:

| Compound No. | Structure | LCMS $MH^+$ m/z | HPLC MS $t_R$ |
|---|---|---|---|
| 26 | 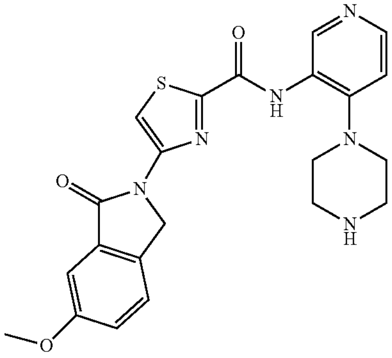 [SMILES: COc1ccc2c(c1)C(=O)N(c1csc(C(=O)Nc3cnccc3N3CCNCC3)n1)C2] | 451.22 | 1.81 |
| 27 | 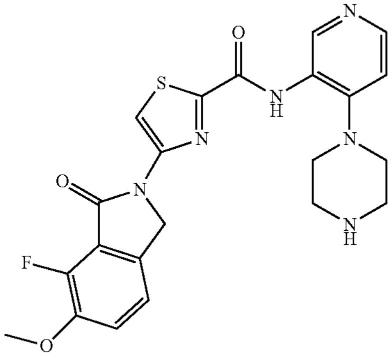 [SMILES: COc1ccc2c(c1F)C(=O)N(c1csc(C(=O)Nc3cnccc3N3CCNCC3)n1)C2] | 469.34 | 1.73 |

-continued
| Compound No. | Structure | LCMS $MH^+$ m/z | HPLC MS $t_R$ |
|---|---|---|---|
| 28 | 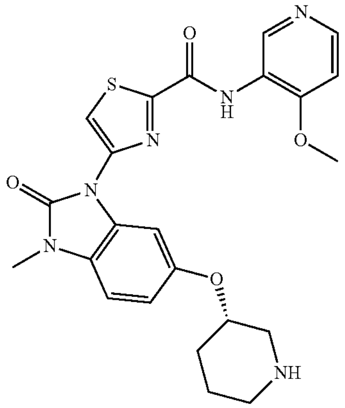 [SMILES: COc1ccncc1NC(=O)c1nc(-n2c(=O)n(C)c3ccc(O[C@H]4CCCNC4)cc32)cs1] | 481.23 | 2.00 |
| 29 | 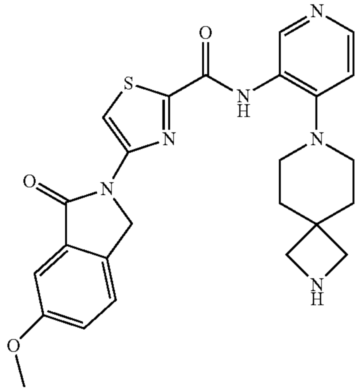 [SMILES: COc1ccc2c(c1)C(=O)N(c1csc(C(=O)Nc3cnccc3N3CCC4(CC3)CNC4)n1)C2] | 491.42 | 1.96 |
| 30 | 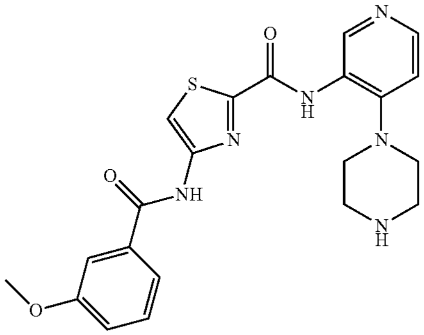 [SMILES: COc1cccc(C(=O)Nc2csc(C(=O)Nc3cnccc3N3CCNCC3)n2)c1] | 438.20 | 1.90 |
| 31 | 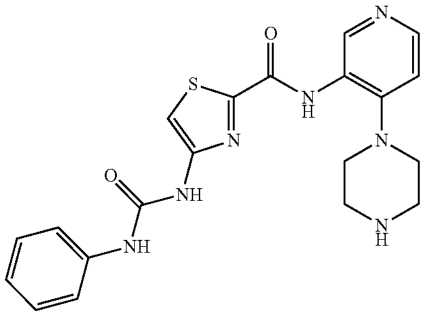 [SMILES: O=C(Nc1ccccc1)Nc1csc(C(=O)Nc2cnccc2N2CCNCC2)n1] | 424.20 | 1.75 |

-continued
| Compound No. | Structure | LCMS MH+ m/z | HPLC MS $t_R$ |
|---|---|---|---|
| 32 | 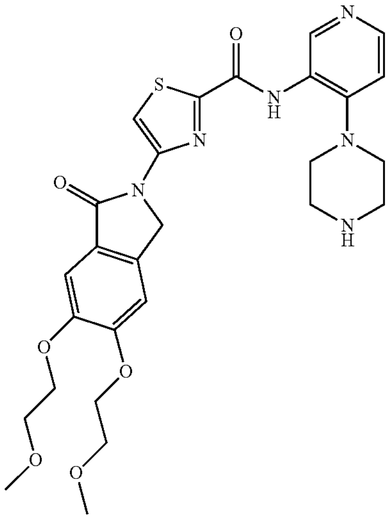 [SMILES: COCCOc1cc2c(cc1OCCOC)C(=O)N(c1csc(C(=O)Nc3cnccc3N3CCNCC3)n1)C2] | 469.10 | 1.50 |
| 33 | 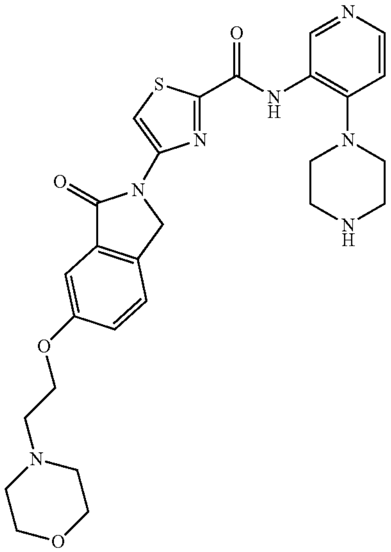 [SMILES: O=C(Nc1cnccc1N1CCNCC1)c1nc(N2Cc3ccc(OCCN4CCOCC4)cc3C2=O)cs1] | 550.10 | 1.25 |
| 34 | 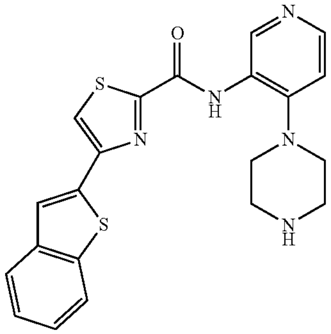 [SMILES: O=C(Nc1cnccc1N1CCNCC1)c1nc(-c2cc3ccccc3s2)cs1] | 422.20 | 2.30 |

-continued

| Compound No. | Structure | LCMS MH$^+$ m/z | HPLC MS $t_R$ |
|---|---|---|---|
| 35 | 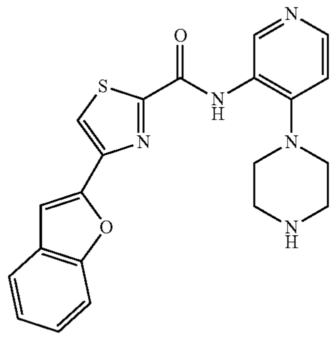 [SMILES: O=C(Nc1cnccc1N1CCNCC1)c1nc(-c2cc3ccccc3o2)cs1] | 406.10 | 2.10 |

Example 5

Preparation of Compound 5A

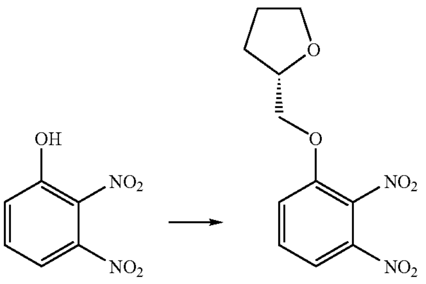

5A 2,3-Dinitro-phenol (384 mg, 2.0 mmol) was dissolved in THF (15 mL) and to the resulting solution was added solid-based triphenylphosphine (600 g, 6.0 mmol), S-(tetrahydro-furan-2-yl)-methanol (286 mg, 2.8 mmol) and DAD (0.79 ml, 4.0 mmol). The resulting reaction was stirred at room temperature for 12 hours, then filtered. The filtrate was diluted with EtOAc, washed sequentially with water and brine, then dried over $Na_2SO_4$, filtered and concentrated in vacuo. The residue obtained was purified using flash column chromatography on silica gel (20% Ethyl acetate/hexanes) to provide compound 5A.

Example 6

Preparation of Compound 6A

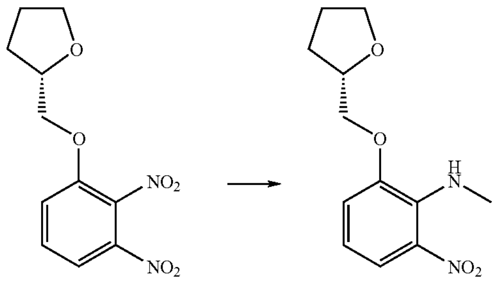

5A 6A

Compound 5A (488 mg, 1.82 mmol) was dissolved in a solution of methylamine in THF (2M, 10.0 mL). The resulting reaction was heated to 60° C. in sealed flask and allowed to stir at this temperature for 12 hours, then concentrated in vacuo. The resulting residue was dissolved in EtOAc and the resulting solution was washed sequentially with water and brine, then dried over $Na_2SO_4$, filtered and concentrated in vacuo to provide compound 6A which was used in the next step without further purification.

Example 7

Preparation of Compound 7A

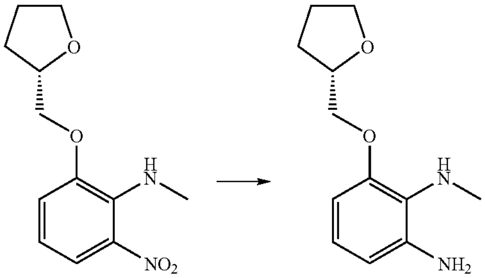

6A 7A

Compound 6A (428 mg, 1.70 mmol) was dissolved in MeOH (10 mL) and to the resulting solution was added 10% Pd/C was added. The resulting solution was hydrogenated on a Parr shaker at 40 atm for 1 hour, and then filtered. The filtrate was concentrated in vacuo to provide compound 7A, which was used in the next step without further purification. HPLC-MS $t_R$=1.14 min ($UV_{254\ nm}$); mass calculated for formula $C_{12}H_{18}N_2O_2$ 222.1, observed LCMS m/z 223.1 (M+H).

Example 8

Preparation of Compound 8A

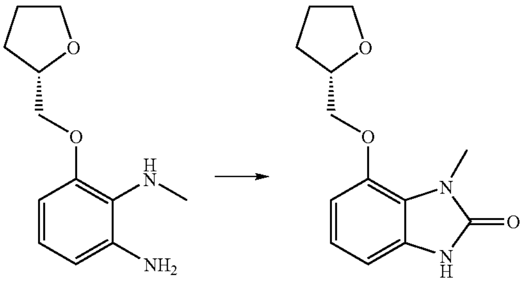

7A 8A

Compound 7A (352 mg, 1.58 mmol) was dissolved in DMF (10 mL) and to the resulting solution was added CDI (307 mg, 1.90 mmol). The resulting reaction was heated to 120° C. and allowed to stir at this temperature for 1 hour. The reaction mixture was cooled to room temperature, diluted with EtOAc, washed sequentially with water and brine, then dried over $Na_2SO_4$, filtered and concentrated in vacuo. The resulting residue was purified using flash column chromatography on silica gel (20% Ethyl acetate/hexanes) to provide compound 8A as a brown solid. HPLC-MS $t_R$=1.45 min ($UV_{254\ nm}$); mass calculated for formula $C_{13}H_{16}N_2O_3$ 248.1, observed LCMS m/z 249.1 (M+H).

Example 9

Preparation of Compound 36

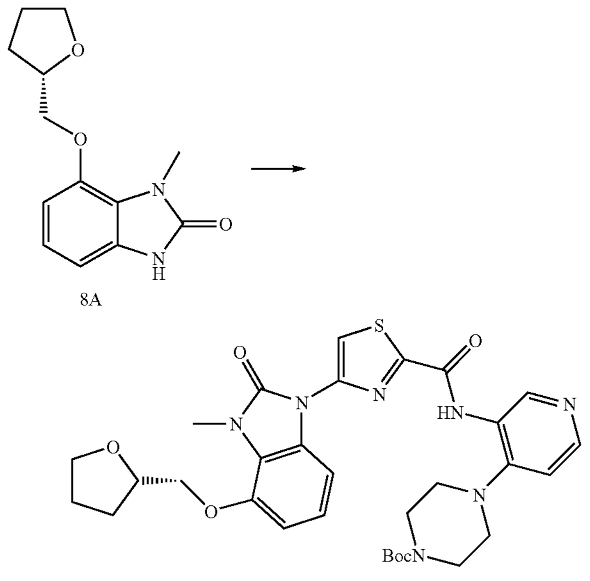

8A

36

To a 25 mL round bottom flask charged with compound 8A (353 mg, 1.42 mmol), benzimidazolone (798 mg, 1.70 mmol), CuI (14 mg, 0.07 mmol), trans-1,2-dimethylaminocyclohexane (20 mg, 0.14) and $K_2CO_3$ (294 mg, 2.13 mmol), was added dioxane (50 mL). The mixture was thoroughly degassed by alternately evacuating the flask under vacuum, then putting under argon atmosphere numerous times. The reaction was then heated to 80° C. and allowed to stir at this temperature for about 15 hours. After cooling to room temperature, the reaction mixture was concentrated in vacuo and the resulting residue was taken diluted with $H_2O$ (25 mL). The resulting solution was filtered and the solid product collected (compound 36) was used directly in the next step without further purification. HPLC-MS $t_R$=1.60 min ($UV_{254\ nm}$); mass calculated for formula $C_{31}H_{37}N_7O_6S$ 635.3, observed LCMS m/z 636.2 (M+H).

Example 10

Preparation of Compound 37

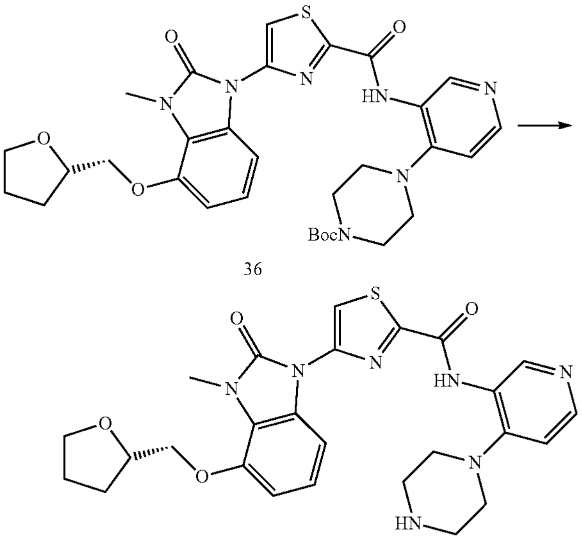

36

37

Compound 37 was prepared from compound 36 using the method described above in Example 4. HPLC-MS $t_R$=1.23 min ($UV_{254\ nm}$); mass calculated for formula $C_{26}H_{29}N_7O_4S$ 535.2, observed LCMS m/z 536.2 (M+H).

Using this method, and substituting the appropriate reactants, the following compounds of the present invention were made:

| Compound No. | Structure | MS m/z (M + H) | HPLC MS $t_R$ |
|---|---|---|---|
| 38 | 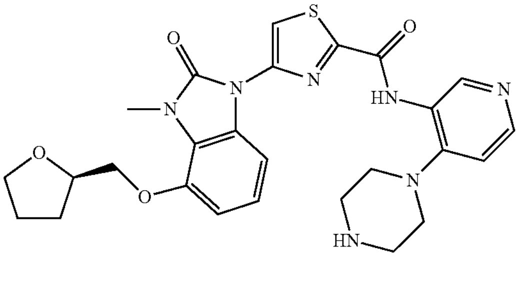 [SMILES: Cn1c(=O)n(-c2csc(C(=O)Nc3cnccc3N3CCNCC3)n2)c2cccc(OC[C@H]3CCCO3)c21] | 536.2 | 1.22 |

-continued

| Compound No. | Structure | MS m/z (M + H) | HPLC MS $t_R$ |
|---|---|---|---|
| 39 | 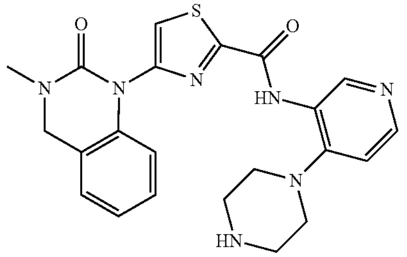 [SMILES: CN1Cc2ccccc2N(c2csc(C(=O)Nc3cnccc3N3CCNCC3)n2)C1=O] | 450.1 | 0.88 |
| 40 | 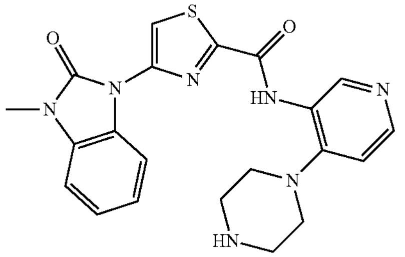 [SMILES: Cn1c(=O)n(-c2csc(C(=O)Nc3cnccc3N3CCNCC3)n2)c2ccccc21] | 436.1 | 0.87 |

Example 11

Preparation of Compound 11C

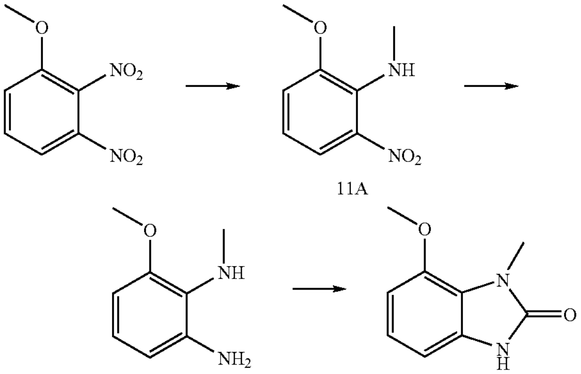

11A 11B 11C

Step A—Synthesis of Compound 11A:

3-Fluorodinitrobenzene (500 mg, 2.5 mmol) was dissolved in EtOH (15 mL) in a sealed tube and to the resulting solution was added methylamine (40% in water, 2 mL). The reaction was heated to 160° C. and stirred at this temperature for about 15 hours. After cooling to room temperature, the mixture was concentrated in vacuo and the resulting residue was purified using column (silica gel) to provide compound 11A (411 mg). HPLC-MS $t_R$=1.60 min ($UV_{254\ nm}$); mass calculated for formula $C_8H_{10}N_2O_3$ 182.1, observed LCMS m/z 183.1 (M+H).

Step B—Synthesis of Compound 11B

Compound 11A (411 mg, 2.26 mmol) was dissolved in THF (50 mL) and Pd/C (10%, 1 g) was added. The reaction was then hydrogenated at 40 psi for 2 hours, then filtered through celite and the filtrate was concentrated in vacuo to provide compound 11B, which was used without further purification. HPLC-MS $t_R$=0.66 min ($UV_{254\ nm}$); mass calculated for formula $C_8H_{12}N_2O$ 152.1, observed LCMS m/z 153.1 (M+H).

Step C—Synthesis of Compound 11C

Compound 11B (350 mg, crude) was dissolved in DMF (2 mL) and to the resulting solution was added carbodiimidazole (370 mg, 2.26 mmol). The reaction was heated to 110° C. and stirred at this temperature for 2 hours. After cooling to room temperature, the reaction mixture was concentrated in vacuo and the resulting residue was purified using flash column chromatography (silica gel, dichloromethane/MeOH=98:2 to dichloromethane/MeOH=96:4) to provide compound 11C (311 mg) as white solid. HPLC-MS $t_R$=1.12 min ($UV_{254\ nm}$); mass calculated for formula $C_9H_{10}N_2O_2$ 178.1, observed LCMS m/z 179.1 (M+H).

The following intermediate compounds were made using the above method and substituting the appropriate starting materials:

| Cpd. No. | Structure | MS m/z (M + H) |
|---|---|---|
| 11D | 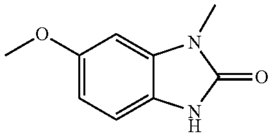 | 179.1 |
| 11E | 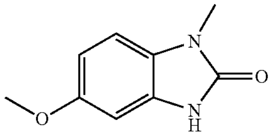 | 179.1 |

-continued

| Cpd. No. | Structure | MS m/z (M + H) |
|---|---|---|
| 11F | 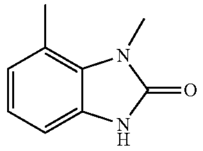 | 163.2 |
| 11G | 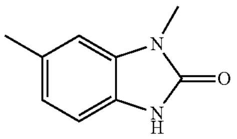 | 163.2 |
| 11H | 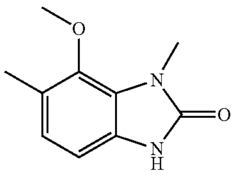 | 193.2 |
| 11I | 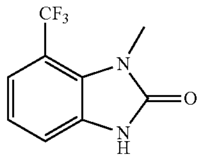 | 217.1 |
| 11J | 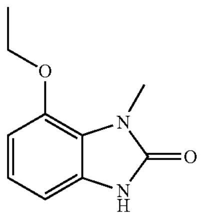 | 193.1 |
| 11K | 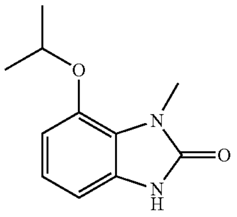 | 207.1 |
| 11L | 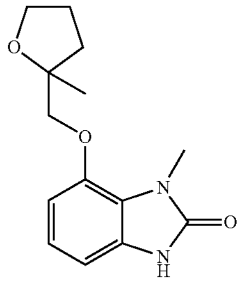 [SMILES: Cn1c(=O)[nH]c2cccc(OCC3(C)CCCO3)c21] | 263.1 |

-continued

| Cpd. No. | Structure | MS m/z (M + H) |
|---|---|---|
| 11M | 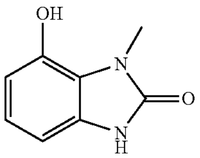 | 165.1 |

Example 12

Preparation of Compound 12D

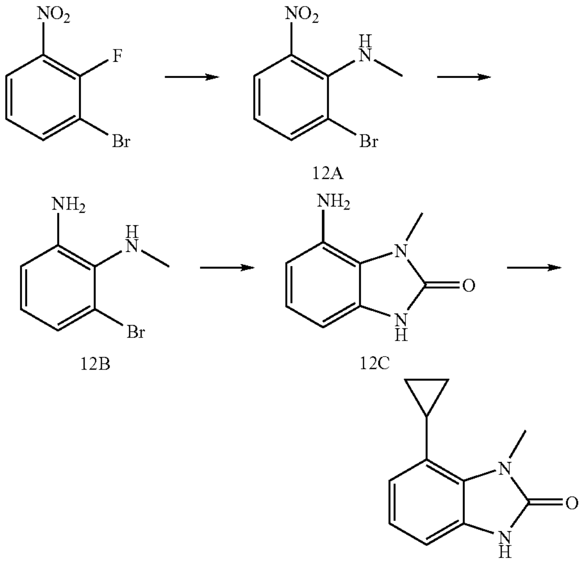

12A

12B

12C

12D

Step A—Synthesis of Compound 12A

1-Bromo-2-fluoro-3-nitro-benzene (440 mg, 2.0 mmol) was dissolved in as solution of methylamine in THF (2M, 10.0 mL). The mixture was heated to 60° C. in sealed flask and allowed to stir at this temperature for 12 hours. The reaction mixture was then concentrated in vacuo and the resulting residue was dissolved in EtOAc and washed sequentially with water and brine, then dried over $Na_2SO_4$, filtered and concentrated in vacuo to provide compound 12A, which was used without further purification. HPLC-MS $t_R$=1.80 min ($UV_{254\ nm}$); mass calculated for formula $C_6H_7N_3O_2$ 230.0, observed LCMS m/z 231.1 (M+H).

Step B—Synthesis of Compound 12B

Compound 12A (410 mg, 1.8 mmol) and iron powder (101 mg, 18 mmol) were dissolved in AcOH (10 mL). The mixture was stirred for 12 hours at 25° C., then filtered and the filtrate was concentrated in vacuo. The residue obtained was dissolved in EtOAc and washed with saturated aqueous $NaHCO_3$ solution followed by brine, then dried over $Na_2SO_4$, filtered and concentrated in vacuo to provide compound 12B which was used without further purification, HPLC-MS $t_R$=0.82 min ($UV_{254\ nm}$); mass calculated for formula $C_6H_7N_3O_2$ 200.0, observed LCMS m/z 201.1 (M+H).

Step C—Synthesis of Compound 12C

Compound 12C was prepared from compound 12B using the method described in Example 7, Step C. HPLC-MS $t_R$=1.52 min ($UV_{254\ nm}$); mass calculated for formula $C_7H_7N_3O$ 226.0, observed LCMS m/z 227.1 (M+H).

D—Synthesis of Compound 12D

Compound 12C (363 mg, 1.6 mmol), $K_3PO_4$ (1.02 g, 4.8 mmol) and Pd(dppf)$Cl_2$ (5% mmol) were dissolved in 1,4 dioxane (5 mL) and the resulting solution was put under argon atmosphere. To this solution was added cyclopropane boronic acid (250 mg, 2.9 mmol) and the reaction was heated to 90° C. and allowed to stir at this temperature for 12 hours. The reaction mixture was diluted with EtOAc, washed sequentially with deionized water and brine, then dried over $Na_2SO_4$, filtered and concentrated in vacuo. The resulting residue was purified using flash column chromatography (silica gel, ethyl acetate as eluent) to provide compound 12D as a white solid. HPLC-MS $t_R$=1.34 min ($UV_{254\ nm}$); mass calculated for formula $C_{11}H_{12}N_2O$ 188.1, observed LCMS m/z 189.1 (M+H).

Example 13

Preparation of Compound 13C

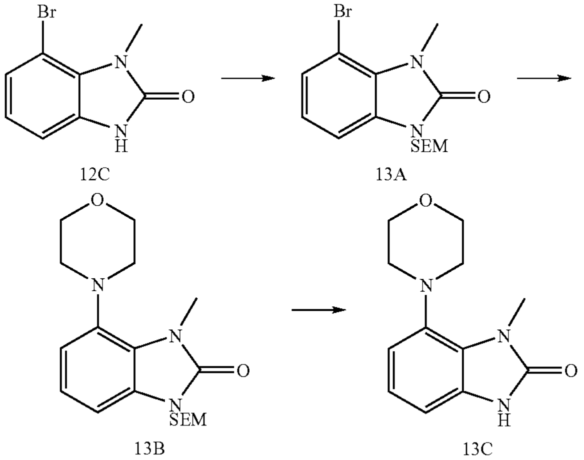

12C 13A 13B 13C

Step A—Synthesis of Compound 13A

Compound 12C (454 mg, 2.0 mmol) was dissolved in DMF (10 mL) and the resulting solution was cooled to 0° C. NaH (88 mg, 2.2 mmol) was added carefully and the resulting reaction was stirred at 0° C. for 10 minutes, then SEMCI (367 mg, 2.2 mmol) was added dropwise and the mixture was allowed to warm to room temperature on its own and stirred for about 15 hours. Saturated aqueous $NH_4Cl$ solution was then added to quench the reaction and the mixture was extracted with EtOAc (40 mLx3). The combined organic layers were dried over $Na_2SO_4$, filtered and concentrated in vacuo and the resulting residue was purified using flash column chromatography (silica gel, 30% EtOAc/Hexanes) to provide compound 13A (688 mg) as oil. HPLC-MS $t_R$=2.32 min ($UV_{254\ nm}$) mass calculated for formula $C_{14}H_{21}BrN_2O_2Si$ 356.1, observed LCMS m/z 329.1 (M+H dimethyl).

Step B—Synthesis of Compound 13B

Under an argon atmosphere, compound 13A (122 mg, 0.34 mmol) was mixed with $Pd_2(dba)_3$ (18 mg, 0.02 mmol), BINAP (25 mg, 0.04 mmol), sodium tert-butoxide (45 mg, 0.45 mmol), morpholine (35 mg, 0.4 mmol) and toluene (2 mL). The resulting reaction was heated to 100° C. and stirred at this temperature for 1 hour. After cooling to room temperature, the mixture was diluted with EtOAc (50 mL) and washed with $NH_4Cl$ (aq.), brine, then dried over $Na_2SO_4$, filtered and concentrated in vacuo. The resulting residue was purified using flash column chromatography (silica gel, 50% EtOAc/Hexane) to provide compound 13B (99 mg). HPLC-MS $t_R$=2.11 min ($UV_{254\ nm}$); mass calculated for formula $C_{18}H_{29}N_3O_3Si$ 363.2, observed LCMS m/z 364.1 (M+H).

Step C—Synthesis of Compound 13C

Compound 13B (99 mg, 0.27 mmol) was dissolved in 4N HCl in dioxane, 4 mL). The mixture was heated to 60° C. and stirred at this temperature for 2 hours. After concentration, MeOH (5 mL) and $Et_3N$ (1 mL) was added and the reaction was heated to 80° C. and allowed to stir at this temperature for 10 minutes in a microwave. After cooling to room temperature, the mixture was concentrated in vacuo and the residue obtained was purified using flash column chromatography (silica gel, dichloromethane/MeOH=95:5) to provide compound 13C as a yellow solid (52 mg). HPLC-MS $t_R$=1.28 min ($UV_{254\ nm}$); mass calculated for formula $C_{12}H_{15}N_3O_2$ 233.1, observed LCMS m/z 234.2 (M+H).

Example 14

Preparation of Compound 14B

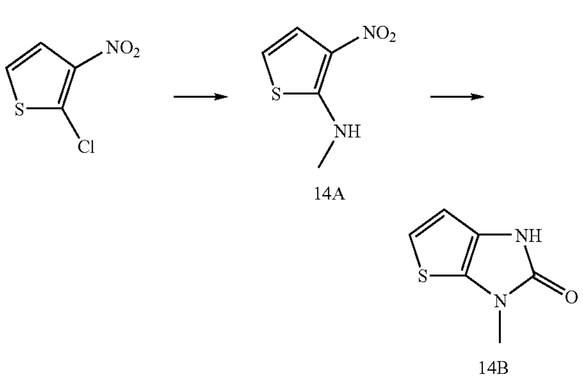

14A 14B

Step A Synthesis of Compound 14A

2-Chloro-3-nitro thiophene (1 g, 6.1 mmol) was dissolved in THF (20 mL) and treated with methylamine (2M in THF, 6 mL). The resulting reaction was stirred at room temperature for 2 hours, and then concentrated in vacuo to provide compound 14A, which was used in the next step without further purification. HPLC-MS $t_R$=1.23 min ($UV_{254\ nm}$); mass calculated for formula $C_5H_6N_2O_2S$ 233.1, observed LCMS m/z 159.1 (M+H).

Step B—Synthesis of Compound 14B

Compound 14A was taken up in DMF (5 mL) and to the resulting solution was added CD (988 mg, 6.1 mmol). The reaction was heated to 110° C. and allowed to stir at this temperature for 1 hour, then cooled to room temperature and concentrated in vacuo. The resulting residue was dissolved in methanol (20 mL) and 10% Pd/C was added under Argon. The reaction was stirred under hydrogen (20 psi) for 4 hours, then filtered and the filtrate was concentrated in vacuo. The resulting residue was purified using flash column chromatography (silica gel, dichloromethane:MeOH=95:5) to provide compound 14B as a solid (280 mg). HPLC-MS $t_R$=0.98 min ($UV_{254\ nm}$); mass calculated for formula $C_6H_6N_2OS$ 154.0, observed LCMS m/z 156.1 (M+H).

Example 15

Preparation of Compound 15F

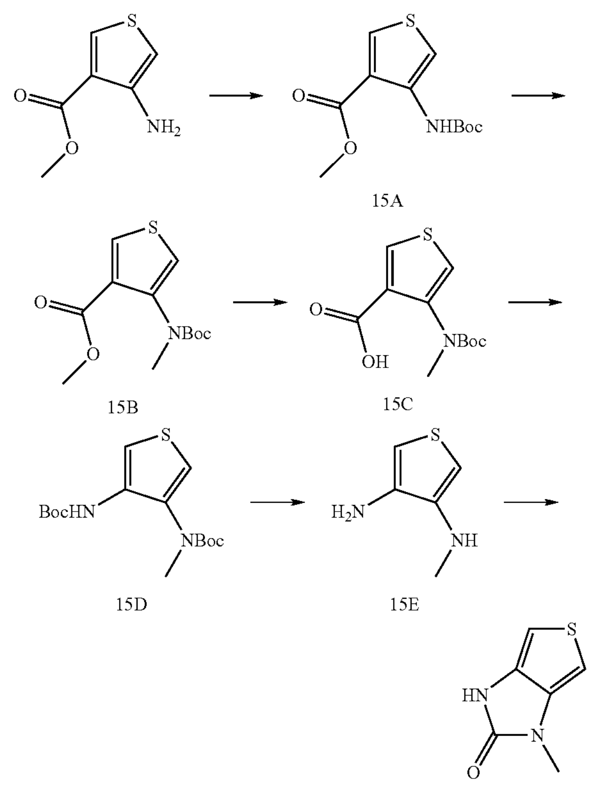

15A 15B 15C 15D 15E 15F

Step A-Synthesis of Compound 15A

Methyl 4-aminothiophene-3-carboxylate (6.57 g, 33.9 mmol) was taken up in 1,4-dioxane (25 mL) and the resulting solution was cooled to 0° C. To the cooled solution was added 5% aqueous $Na_2CO_3$, followed by a solution of di-tert-butyl dicarbonate (18.6 g, 85.2 mmol) in dioxane (25 mL). The cold bath was removed and the reaction mixture was allowed to warm to room temperature on its own and stir at this temperature for 16 hours. An additional portion of di-ten-butyl dicarbonate (3.86 g, 17.7 mmol) in 1,4-dioxane (10 mL) was then added and the reaction mixture was stirred at room temperature for an additional 24 hours, then diluted with water and EtOAc. The aqueous layer was extracted with EtOAc and the combined organic layers were washed with water and brine, dried over $Na_2SO_4$, filtered and concentrated in vacuo. The residue obtained was purified using flash column chromatography on silica gel (20% ethyl acetate/hexanes) to provide compound 15A as a colorless liquid.

Step B—Synthesis of Compound 15B

NaH (1.44 g, 36 mmol) was added to a 0° C. solution of compound 15A (7.72 g, 30 mmol) in DMF (15 mL). The reaction was allowed to stir for 10 minutes, then methyl iodide (2.32 mL, 36 mmol) was added. The reaction mixture was stirred for 16 hours at room temperature, then saturated aqueous $NH_4Cl$ solution was added to the reaction mixture and the mixture was extracted with dichloromethane (3×15 mL). The combined organic layers were washed with water, then brine, then dried over $Na_2SO_4$, filtered and concentrated in vacuo. The residue obtained was purified using flash column chromatography on silica gel (10% ethyl acetate-hexanes) to provide compound 15B. HPLC-MS $t_R$=1.84 min ($UV_{254\ nm}$); mass calculated for formula $C_{12}H_{17}NO_4S$ 271.1, observed LCMS m/z 294.1 (M+Na), Step C—Synthesis of Compound 15C Compound 15B (6.78 g, 25 mmol) was taken up in an aqueous LiOH solution (1.0 M, 30 mL) and the resulting reaction was allowed to stir for 12 hours at room temperature. The reaction mixture was then neutralized using HCl (1.0 N) to pH 5.0-7.0. The resulting aqueous solution was extracted with dichloromethane (3×50 mL) and the combined organic layer were washed sequentially with water and brine, then dried over $Na_2SO_4$, filtered and concentrated in vacuo. The resulting residue was purified using flash column chromatography on silica gel (50% ethyl acetate-hexanes) to provide compound 15C. HPLC-MS $t_R$=1.48 min ($UV_{254\ nm}$); mass calculated for formula $C_{11}H_{15}NO_4S$ 257.1, observed LCMS m/z 280.1 (M+Na).

Step D—Synthesis of Compound 15D

A mixture of compound 15C (6.02 g, 23.4 mmol), DPPA (7.08 g, 257 mmol) and $Et_3N$ (3.59 mL, 25.7 mmol) in t-BuOH (30 mL) was heated to reflux and allowed to stir at this temperature for 12 hours. The reaction mixture was cooled to room temperature and concentrated in vacuo and the residue obtained was purified using flash column chromatography on silica gel (20% ethyl acetate-hexanes) to provide compound 15D. HPLC-MS $t_R$=1.20 min ($UV_{254\ nm}$); mass calculated for formula $C_{15}H_{24}N_2O_4S$ 328.1, observed LCMS m/z 329.0 (M+H).

Step E—Synthesis of Compound 15E

Compound 15D (6.63 g, 20.2 mmol) was dissolved in HCl in dioxane (20 mL) and the resulting reaction was allowed to stir for 20 minutes. The reaction mixture was concentrated in vacuo and the resulting residue was purified using flash column chromatography on silica gel (50% ethyl acetate-hexanes) to provide compound 15E.

Step F—Synthesis of Compound 15F

Compound 15E (1.88 g, 14.7 mmol) was dissolved in DMF (10 mL) and CDI (2.86 mg, 17.6 mmol) was added. The reaction was heated to 120° C. and allowed to stir at this temperature for 1 hour. The reaction mixture was cooled to room temperature, diluted with EtOAc and washed with water, brine and dried over $Na_2SO_4$. After concentration in vacuo, the crude product was purified using flash column chromatography on silica gel (100% ethyl acetate) to provide compound 15F. HPLC-MS $t_R$=0.97 min ($UV_{254\ nm}$); mass calculated for formula $C_6H_6N_2OS$— 154.0, observed LCMS m/z 155.0 (M+H).

Example 16

Preparation of Compounds 41 and 42

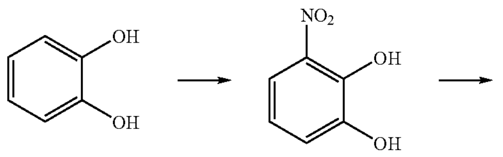

16A

-continued

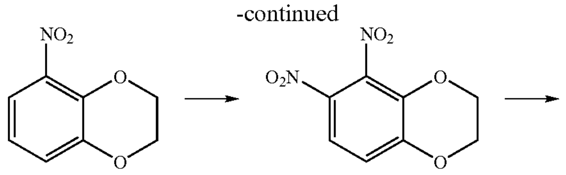

16B 16C

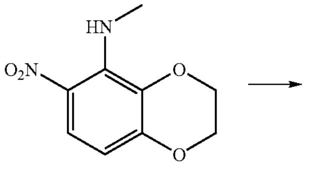

16D

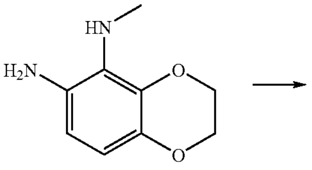

16E

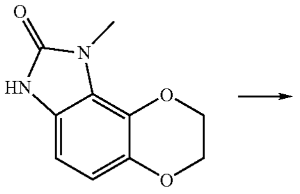

16F

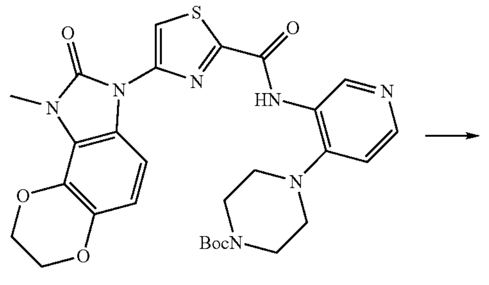

41

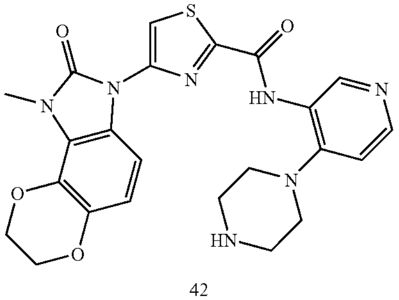

42

Step A—Synthesis of Compound 16A

Catechol (2.2 g, 20.0 mmol) was dissolved in ether (100 mL) and to the resulting solution was added fuming nitric acid (1.0 mL) dropwise. The reaction was stirred at room temperature for 20 minutes, decanted into ice-water and the resulting solution was extracted with ether (3x50 mL). The combined organic extracts were neutralized with 10% sodium carbonate solution, dried over $Na_2SO_4$, filtered and concentrated in vacuo. The residue obtained was purified using flash column chromatography on silica gel (40% ethyl acetate-hexanes) to provide compound 16k Step B—Synthesis of Compound 16B A mixture of compound 16A (1.10 g, 7.1 mol), 1,2-dibromoethane (9.33 g, 49.7 mmol) and anhydrous potassium carbonate (2.94 g, 21.3 mmol) in isoamyl alcohol (100 mL) was heated to reflux and allowed to stir at this temperature for 7 hours. Additional 1,2-dibromoethane (6.57 g, 35.0 mmol) and anhydrous potassium carbonate (4.84 g, 35.0 mmol) were added to the reaction mixture and reaction was stirred at reflux for 8 additional hours, then cooled to room temperature. The isoamyl alcohol was removed in vacuo and the liquid residue obtained was decanted into water, extracted with dichloromethane and the dichloromethane solution was concentrated in vacuo. The resulting residue was purified using flash column chromatography on silica gel (20% ethyl acetate-hexanes) to provide compound 16B as pale-yellow solid. HPLC-MS $t_R$=1.57 min ($UV_{254\ nm}$); mass calculated for formula $C_8H_7NO_4$ 181.0, observed LCMS m/z 182.1 (M+H).

Step C—Synthesis of Compound 16C

To a solution of compound 16B (964 mg, 5.3 mmol) in acetic acid (2.5 mL) was added fuming nitric acid (6.0 mL). The reaction was stirred for 1 hour, then decanted into ice-water and extracted with dichloromethane (2x10 mL). The combined extracts were washed with 10% sodium carbonate solution, dried over $Na_2SO_4$ and concentrated in vacuo. The resulting residue was purified using flash column chromatography on silica gel (20% ethyl acetate-hexanes) to provide compound 16C. HPLC-MS $t_R$=1.53 min ($UV_{254\ nm}$); mass calculated for formula $C_8H_6N_2O_6$ 226.0, observed LCMS m/z 227.1 (M+H).

Step D—Synthesis of Compound 16D

Compound 16C (588 mg, 2.6 mmol) was dissolved in a solution of methylamine in THF (2M, 10.0 mL). The reaction was heated to 60° C. in sealed flask and allowed to stand at this temperature for 12 hours, then concentrated in vacuo. The resulting residue was dissolved in EtOAc and washed with water, brine and dried over $Na_2SO_4$. After concentration in vacuo, compound 16D was obtained as a crude residue and used without further purification. HPLC-MS $t_R$=1.72 min ($UV_{254\ nm}$); mass calculated for formula $C_9H_{10}N_2O_4$ 210.1, observed LCMS m/z 211.1 (M+H).

Step E—Synthesis of Compound 16E

Compound 160 (462 mg, 2.2 mmol) was dissolved in MeOH (10 mL) and to the resulting solution was added 10% Pd/C. The reaction was hydrogenated in a Paar shaker at 40 atm for 1 hour, then filtered. The filtrate was concentrated to provide compound 16E was used without further purification. HPLC-MS $t_R$=0.62 min ($UV_{254\ nm}$); mass calculated for formula $C_{12}H_{18}N_2O_2$ 180.1, observed LCMS m/z 181.2 (M+H).

Step F—Synthesis of Compound 16F

Compound 16E (342 mg, 1.9 mmol) was dissolved in DMF (10 mL) and CDI (373 mg, 2.3 mmol) was added. The mixture was heated to 120° C. and allowed to stir at this temperature for 1 hour. The mixture was cooled to room temperature, diluted with EtOAc and washed with water, brine and dried over $Na_2SO_4$. After concentration, the resulting residue was purified using flash column chromatography on silica gel (100% ethyl acetate) to provide compound 16F as brown solid. HPLC-MS $t_R$=1.20 min ($UV_{254\ nm}$); mass calculated for formula $C_{10}H_{10}N_2O_3$ 206.1, observed LCMS m/z 207.1 (M+H).

Step G—Synthesis of Compound 41

To a mixture of compound 16F (293 mg, 1.42 mmol), compound IA (798 mg, 1.70 mmol), CuI (14 mg, 0.07 mmol), trans-1,2-dimethylaminocyclohexane (20 mg, 0.14) and $K_2CO_3$ (294 mg, 2.13 mmol) was added dioxane (50 mL).

The resulting solution was thoroughly degassed by alternately connected the flask to vacuum and Argon. This resulting mixture was then heated to 80° C. and allowed to stir at this temperature for about 15 hours. After cooling to room temperature, the solvent was removed in vacuo. The residue obtained was diluted with $H_2O$ (25 mL) and the resulting solution was filtered. The collected solid (compound 41) was used in the next step without further purification. HPLC-MS $t_R$=1.63 min ($UV_{254\ nm}$); mass calculated for formula $C_{28}H_{31}N_7O_6S$ 593.2, observed LCMS m/z 594.2 (M+H).

Step H—Synthesis of Compound 42

Compound 42 was prepared by deprotecting compound 41 according to the method described in Example 4. HPLC-MS $t_R$=1.06 min ($UV_{254\ nm}$); mass calculated for formula $C_{23}H_{23}N_7O_4S$ 493.2, observed LCMS m/z 494.2 (M+H).

Using the above method, and substituting the appropriate benzimidazolone reactants, the following compounds of the present invention were made:

| Cpd. No. | Structure | MS m/z (M + H) | HPLC MS $t_R$ |
|---|---|---|---|
| 43 | 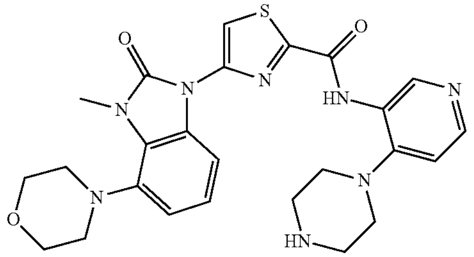 [SMILES: Cn1c(=O)n(-c2csc(C(=O)Nc3cnccc3N3CCNCC3)n2)c2cccc(N3CCOCC3)c21] | 521.2 | 1.10 |
| 44 | 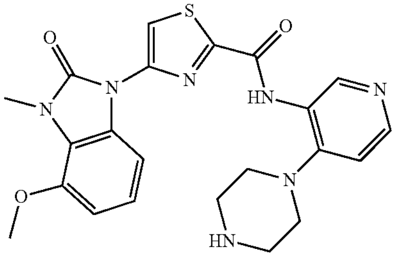 [SMILES: COc1cccc2c1n(C)c(=O)n2-c1csc(C(=O)Nc2cnccc2N2CCNCC2)n1] | 466.1 | 0.95 |
| 45 | 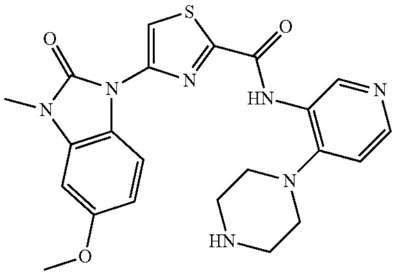 [SMILES: COc1ccc2c(c1)n(C)c(=O)n2-c1csc(C(=O)Nc2cnccc2N2CCNCC2)n1] | 466.1 | 0.90 |
| 46 | 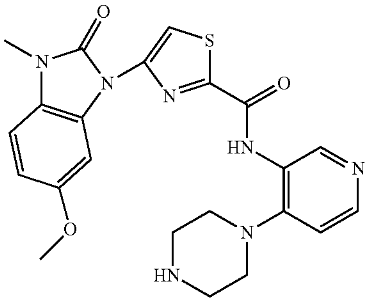 [SMILES: COc1ccc2c(c1)n(-c1csc(C(=O)Nc3cnccc3N3CCNCC3)n1)c(=O)n2C] | 466.1 | 0.89 |

-continued
| Cpd. No. | Structure | MS m/z (M + H) | HPLC MS $t_R$ |
|---|---|---|---|
| 47 | 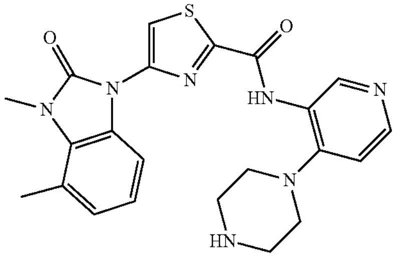 [SMILES: Cc1cccc2c1n(C)c(=O)n2-c1csc(C(=O)Nc2cnccc2N2CCNCC2)n1] | 450.1 | 0.94 |
| 48 | 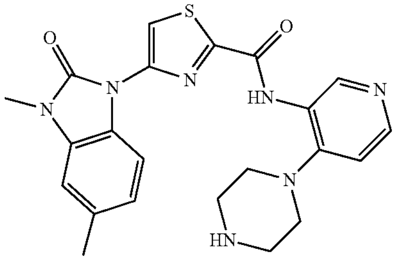 [SMILES: Cc1ccc2c(c1)n(C)c(=O)n2-c1csc(C(=O)Nc2cnccc2N2CCNCC2)n1] | 450.1 | 0.96 |
| 49 | 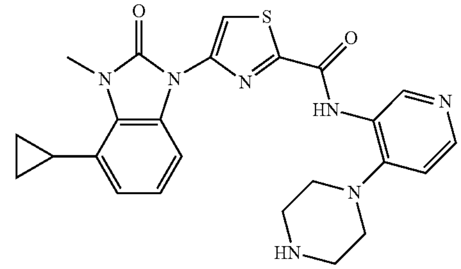 [SMILES: Cn1c(=O)n(-c2csc(C(=O)Nc3cnccc3N3CCNCC3)n2)c2cccc(C3CC3)c21] | 476.2 | 1.07 |
| 50 | 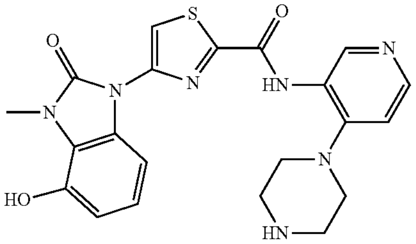 [SMILES: Cn1c(=O)n(-c2csc(C(=O)Nc3cnccc3N3CCNCC3)n2)c2cccc(O)c21] | 452.2 | 0.93 |
| 51 | 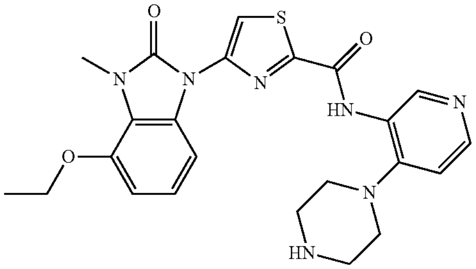 [SMILES: CCOc1cccc2c1n(C)c(=O)n2-c1csc(C(=O)Nc2cnccc2N2CCNCC2)n1] | 480.2 | 1.09 |

-continued
| Cpd. No. | Structure | MS m/z (M + H) | HPLC MS $t_R$ |
| --- | --- | --- | --- |
| 52 | 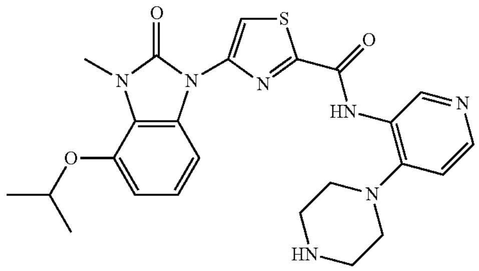 [SMILES: CC(C)Oc1cccc2c1n(C)c(=O)n2-c1csc(C(=O)Nc2cnccc2N2CCNCC2)n1] | 494.2 | 1.16 |
| 53 | 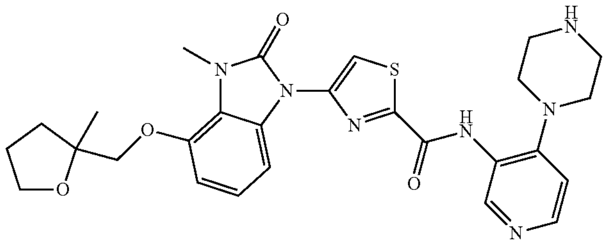 [SMILES: Cn1c(=O)n(-c2csc(C(=O)Nc3cnccc3N3CCNCC3)n2)c2cccc(OCC3(C)CCCO3)c21] | 550.2 | 1.17 |
| 54 | 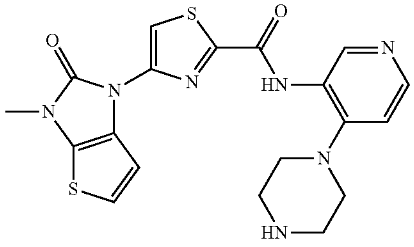 [SMILES: Cn1c(=O)n(-c2csc(C(=O)Nc3cnccc3N3CCNCC3)n2)c2ccsc21] | 442.0 | 0.96 |
| 55 | 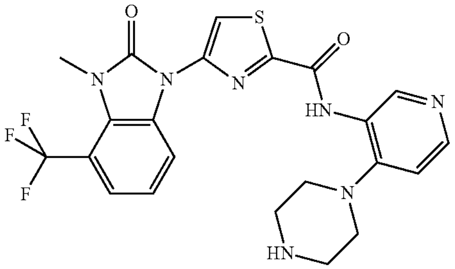 [SMILES: Cn1c(=O)n(-c2csc(C(=O)Nc3cnccc3N3CCNCC3)n2)c2cccc(C(F)(F)F)c21] | 504.1 | 1.27 |
| 56 | 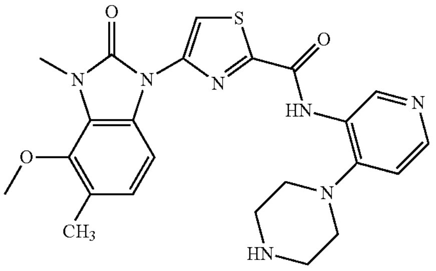 [SMILES: COc1c(C)ccc2c1n(C)c(=O)n2-c1csc(C(=O)Nc2cnccc2N2CCNCC2)n1] | 480.1 | 1.02 |

-continued

| Cpd. No. | Structure | MS m/z (M + H) | HPLC MS $t_R$ |
|---|---|---|---|
| 57 | 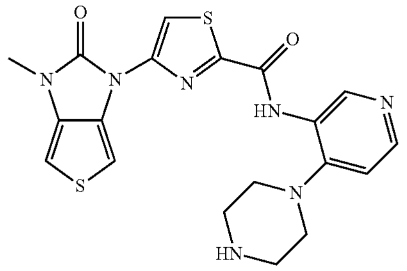 [SMILES: Cn1c(=O)n(-c2csc(C(=O)Nc3cnccc3N3CCNCC3)n2)c2cscc21] | 442.1 | 0.86 |

Example 17

Preparation of Compounds 58 and 59

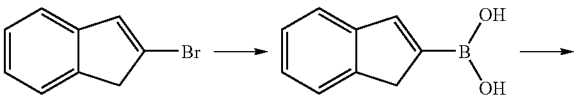

17A

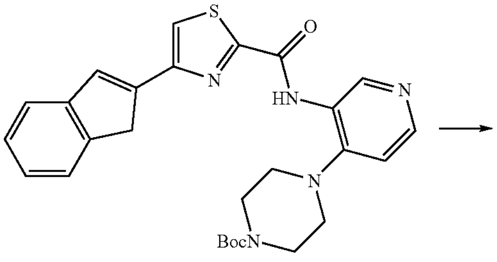

58

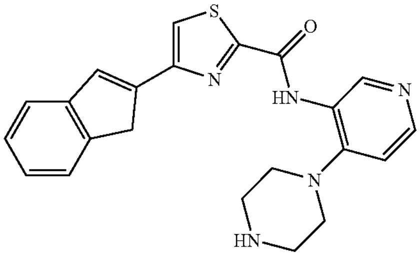

59

Step A—Synthesis of Compound 17A

Under an atmosphere of argon, magnesium turnings (0.86 g, 35 mmol) covered with dry THF (5 mL) were activated with a few drops of 1,2-dibromoethane. To the solution of activated magnesium turnings was added dropwise a solution of 2-bromo-1H-indene (3.45 g, 17.7 mmol) in dry THF (20 mL). The reaction was stirred at room temperature for 2 hours, then the reaction mixture was added via syringe to a −80° C. solution of tri-isopropoxy-borane (4.6 mL, 20 mmol) in dry THF (10 mL). The resulting reaction was allowed to warm to room temperature on its own and was stirred for 16 hours. The reaction mixture was quenched with ice and acidified with HCl, then extracted with ether (3×15 mL). The combined organic phases were washed with brine, dried over $Na_2SO_4$, filtered and concentrated in vacuo. The resulting residue was purified using flash column chromatography on silica gel (40% ethyl acetate/hexanes) to provide compound 17A.

Step B—Synthesis of Compound 58

A mixture of compound 17A (32 mg, 0.2 mmol), compound 1A (46.9 mg, 0.1 mmol), $Pd_2(DBA)_3$ (9.2 mg, 0.01 mmol), S-Phos (8.2 mg, 0.02 mmol) and $K_3PO_4$(42 mg, 0.2 mmol) in 1,4-dioxane (3 mL) was heated to 100° C. and allowed to stir at this temperature for 15 hours under argon. The reaction mixture was then cooled to room temperature, diluted with ethyl acetate and filtered through celite. The filtrate was concentrated in vacuo and the residue obtained was purified using HPLC to provide compound 58. HPLC-MS $t_R$=1.78 min ($UV_{254\ nm}$); mass calculated for formula $C_{27}H_{29}N_5O_3$ 503.2, observed LCMS m/z 504.1 (M+H).

Step C—Synthesis of Compound 59

Compound 59 was prepared by deprotecting compound 58 according to the method described in Example 4. HPLC-MS $t_R$=1.05 min ($UV_{254\ nm}$); mass calculated for formula $C_{22}H_{21}N_5OS$ 403.1, observed LCMS m/z 404.1 (M+H).

Example 18

Preparation of Compound 18F

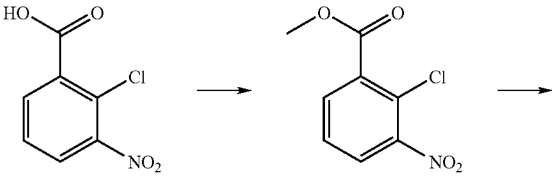

18A

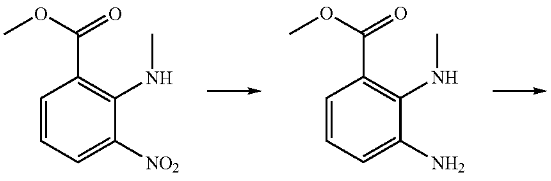

18B 18C

-continued

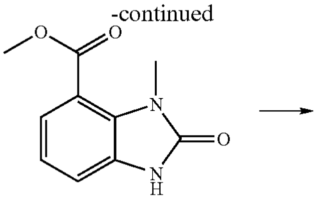

18D

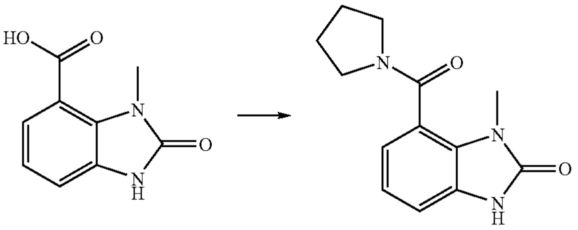

18E 18F

Step A—Synthesis of Compound 18A

2-Chloro-3-nitrobenzoic acid (1.0 g, 5.0 mmol) was dissolved in dichloromethane (10 mL) and to the resulting solution was added an excess of triethylamine, followed by a drop of DMF, then the solution was cooled to 0° C., and oxalyl chloride (1 eq.) was added and reaction was stirred at room temperature for 2 hours. The reaction mixture was concentrated in vacuo and the residue obtained was purified using flash column chromatography on silica gel (20% ethyl acetate/hexanes) to provide compound 18A (1 g). HPLC-MS $t_R$=1.60 min ($UV_{254\ nm}$); mass calculated for formula $C_8H_6ClNO_4$ 215.10, observed LCMS m/z 216.10 (M+H).

Step B—Synthesis of Compound 18B

Compound 18A (1 g) was dissolved in EtOH (15 mL) and methylamine (40% in water, 2 mL) was added. The mixture was put in a sealed tube and heated to 160° C. and stirred at this temperature for about 15 hours. After cooling to room temperature, the mixture was concentrated in vacuo and the residue obtained was purified using flash column chromatography on silica gel (40% ethyl acetate/hexanes) to provide compound 186 (0.85 g). HPLC-MS $t_R$=1.20 min ($UV_{254\ nm}$); mass calculated for formula $C_9H_{10}N_2O_4$ 210.06, observed LCMS m/z 211.10 (M+H)

Step C—Synthesis of Compound 18C

Compound 18B (0.85 g) was dissolved in ethanol and 10% Pd/C (50 mg) was added to the solution. The reaction was stirred under hydrogen atmosphere at atmospheric pressure for 4 hours, then filtered through celite and the filtrate was concentrated in vacuo. The resulting residue (compound 18C) was used in the next step without further purification. HPLC-MS $t_R$=1.00 min ($UV_{254\ nm}$); mass calculated for formula $C_9H_{12}N_2O_2$ 180.09, observed LCMS m/z 181.10 (M+H)

Step D—Synthesis of Compound 18D

Compound 18C (360 mg, crude) was dissolved in DMF (2 mL) and CU (370 mg, 2.26 mmol) was added. The reaction was heated to 110° C. and stirred at this temperature for 2 hours. After cooling to room temperature, the reaction mixture was concentrated in vacuo and the resulting residue was purified using flash column chromatography on silica gel (dichloromethane/MeOH=98:2 to dichloromethane/MeOH=96:4) to provide compound 18D (311 mg) as white solid. HPLC-MS $t_R$=1.25 min ($UV_{254\ nm}$); mass calculated for formula $C_{10}H_{10}N_2O_3$ 206.07, observed LCMS m/z 207.10 (M+H).

Step E—Synthesis of Compound 18E

Compound 18D (310 mg, 1.0 mmol) was dissolved in THF (10 mL) and aqueous LiOH solution (1N, 2 mL) was added. The reaction was stirred at room temperature for about 15 hours, then was concentrated in vacuo. The resulting residue was treated with 1N HCl until the resulting solution was at pH 5. The solution was then filtered and the collected solid was dried under air to provide compound 18E (300 mg). HPLC-MS $t_R$=0.90 min ($UV_{254\ nm}$); mass calculated for formula $C_9H_8N_2O_3$ 192.1, observed LCMS m/z 193.2 (M+H).

Step F—Synthesis of Compound 18E

Compound 18E (192 mg, 1 mmol) was dissolved in DMF, and HATU (380 mg, 1 eq.) and diisopropylethylamine (525 μL, 3 eq.) were added. The reaction was stirred at room temperature for 10 minutes, then pyrrolidine (1 eq.) was added. The reaction mixture was stirred at room temperature for 2 hours, then concentrated in vacuo and the resulting residue was purified using flash column chromatography on silica gel (100% ethyl acetate) to provide compound 18F (200 mg). HPLC-MS $t_R$=1.40 min ($UV_{254\ nm}$); mass calculated for formula $C_{13}H_{15}N_3O_2$ 245.12, observed LCMS m/z 246.10 (M+H)

Example 19

Preparation of Compound 19F

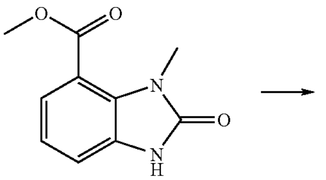

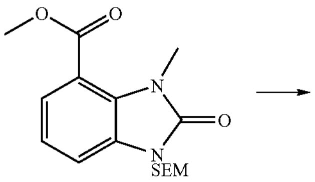

19A

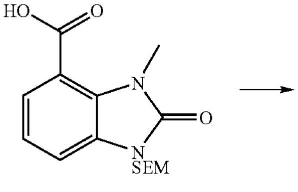

19B

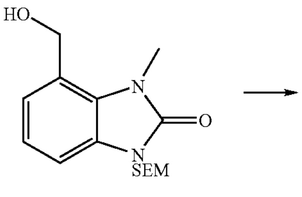

19C

-continued

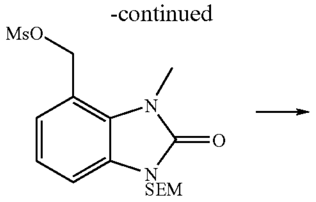

19D

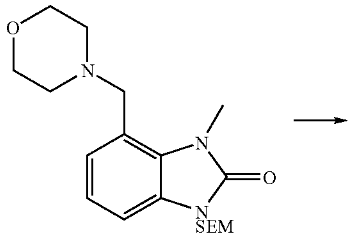

19E

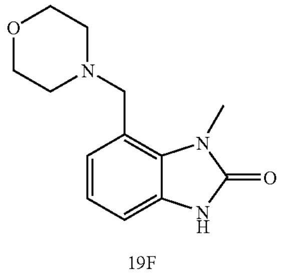

19F

Step A—Synthesis of Compound 19A

Compound 19A was synthesized from the indicated starting material using the method described in Example 12. HPLC-MS $t_R$=2.23 min ($UV_{254\ nm}$); mass calculated for formula $C_{16}H_{24}N_2O_4Si$ 336.16, observed LCMS m/z 337.2 (M+H).

Step B—Synthesis of Compound 19B

Compound 19A (350 mg, 1.0 mmol) was dissolved in THF (10 mL) and LiOH (1 N, 2 mL) was added. The mixture was stirred at room temperature over night. After concentration, 1N HCl was added to adjust the pH to 5. The solid, 19B was filtered off and dried under air (309 mg). HPLC-MS $t_R$=1.81 min ($UV_{254\ nm}$); mass calculated for formula $C_{15}H_{22}N_2O_4Si$ 322.1, observed LCMS m/z 323.2 (M+H).

Step C—Synthesis of Compound 19C

Compound 19B (200 mg, 0.62 mmol) was converted to compound 19C (190 mg) using the method described in Example 18, Step E. HPLC-MS $t_R$=1.76 min ($UV_{254\ nm}$); mass calculated for formula $C_{15}H_{24}N_2O_3Si$ 308.2, observed LCMS m/z 309.1 (M+H).

Step D—Synthesis of Compound 19D

Compound 19C (190 mg, 0.6 mmol) was dissolved in dry dichloromethane (10 mL) and triethylamine (140 μL, 0.6 mmol) was added. The solution was cooled to 0° C. and MsCl (0.6 mmol) was added and the resulting reaction was warmed to room temperature and stirred at this temperature for 2 hours. The reaction mixture was diluted with dichloromethane and washed with water, then brine, then dried over sodium sulfate, filtered and concentrated in vacuo to provide compound 19D, which was used without further purification.

Step E—Synthesis of Compound 19E

Compound 19D was dissolved in DMF (5 mL) and $K_2CO_3$ (138 mg, 1.0 mmol) was added followed by morpholine (0.5 mL). After stirring at room temperature for 1 hour, EtOAc (100 mL) was added and the reaction mixture was washed with water, brine and dried over $Na_2SO_4$. After concentration in vacuo, the residue obtained (compound 19E) was used without further purification. HPLC-MS $t_R$=1.36 min ($UV_{254\ nm}$); mass calculated for formula $C_{19}H_{31}N_3O_3Si$ 377.2, observed LCMS m/z 378.3 (M+H).

Step F—Synthesis of Compound 19F

Compound 19F was synthesized from compound 19E using the method described above in Example 13, Step C. HPLC-MS $t_R$=0.49 min ($UV_{254\ nm}$); mass calculated for formula $C_{13}H_{17}N_3O_2$ 247.1, observed LCMS m/z 248.2 (M+H).

Using the methods described in the Examples above and employing the appropriately reactants, the following intermediate compounds were made:

| Cpd. No. | Structure | MS m/z (M + H) | HPLC MS $t_R$ |
|---|---|---|---|
| 19G | 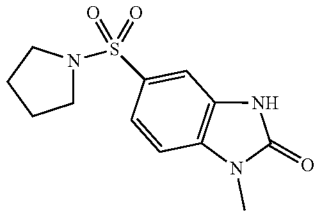 [SMILES: Cn1c(=O)[nH]c2cc(S(=O)(=O)N3CCCC3)ccc21] | 282.1 | 0.64 |
| 19H | 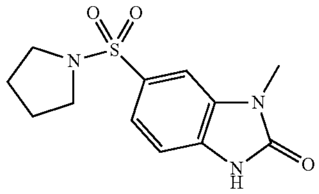 [SMILES: Cn1c(=O)[nH]c2ccc(S(=O)(=O)N3CCCC3)cc21] | 282.1 | 0.63 |
| 19I | 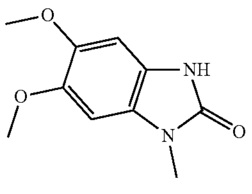 | 208.2 | 1.10 |
| 19J | 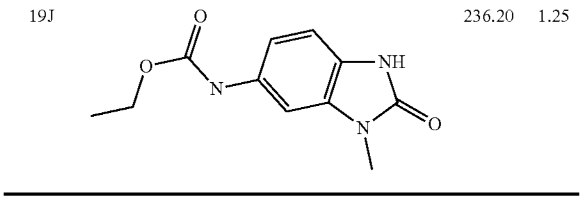 | 236.20 | 1.25 |

Example 20

Preparation of Compounds 60 and 61

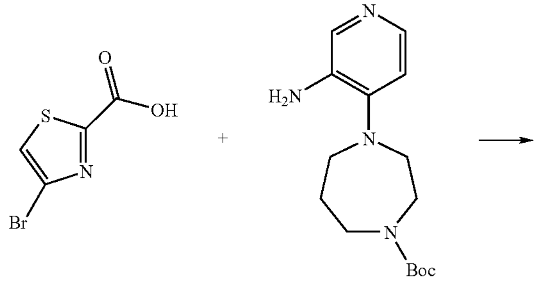

20A

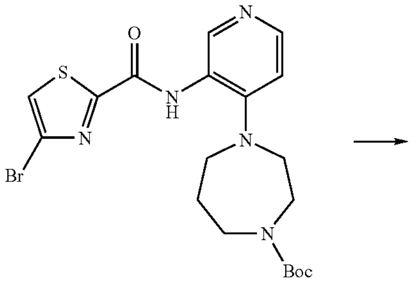

20B

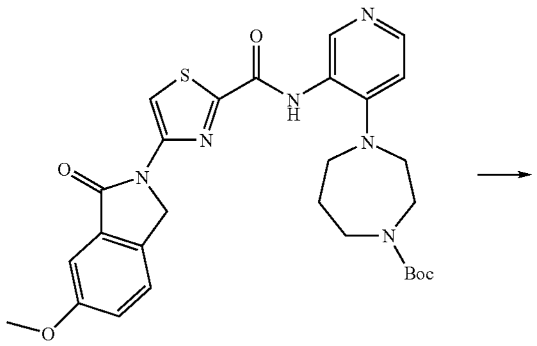

60

-continued

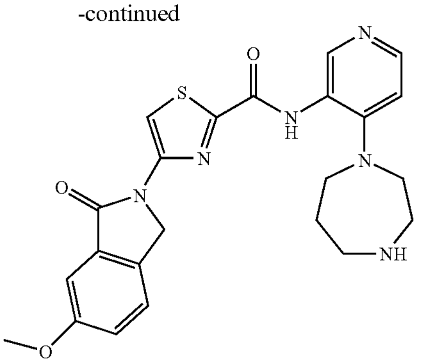

61

Step A—Synthesis of Compound 20B

To a solution of 4-bromo-triazole-2-carboxylic acid (150 mg, 0.72 mmol) in DMF (7 mL) was added compound 20A (292 mg, 1:0 mmol, made using the method described in Scheme 4 above), HATU (380 mg, 1.0 mmol) and diisopropylethylamine (525 μL, 3.0 mmol). The resulting reaction was stirred at room temperature about 15 hours, then concentrated in vacuo. The resulting residue was purified using flash column chromatography on silica gel (40% ethyl acetate/hexanes) to provide compound 20B. HPLC-MS $t_R$=1.34 min ($UV_{254\ nm}$); mass calculated for formula $C_{19}H_{24}N_5O_3SBr$ 481.08, observed LCMS m/z 482.20 (M+H).

Step B—Synthesis of Compound 60

Compound 20B was reacted with 6-methoxyisoindolin-1-one according to the method described in Example 3 to provide compound 60. HPLC-MS $t_R$=1.34 min ($UV_{254\ nm}$); mass calculated for formula $C_{28}H_{32}N_6O_5S$ 564.22, observed LCMS m/z 565.20 (M+H).

Step C—Synthesis of Compound 61

Compound 60 was deprotected using the method described in Example 4 to provide compound 61. HPLC-MS $t_R$=1.34 min ($UV_{254\ nm}$); mass calculated for formula $C_{23}H_{24}N_6O_5S$ 464.16, observed LCMS m/z 465.20 (M+H).

Using the methods described above and substituting the appropriate reactants, the following compounds of the present invention were made:

| Cpd. No. | Structure | LCMS $MH^+$ m/z | HPLC MS $t_R$ |
|---|---|---|---|
| 62 | 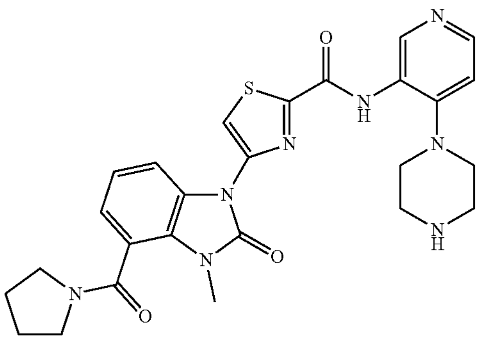 [SMILES: Cn1c(=O)n(-c2csc(C(=O)Nc3cnccc3N3CCNCC3)n2)c2cccc(C(=O)N3CCCC3)c21] | 533.20 | 1.40 |

-continued
| Cpd. No. | Structure | LCMS MH+ m/z | HPLC MS $t_R$ |
|---|---|---|---|
| 63 | 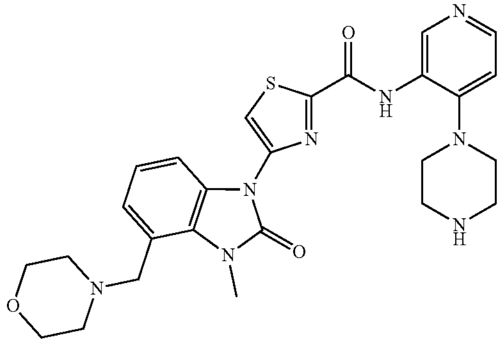 [SMILES: Cn1c(=O)n(-c2csc(C(=O)Nc3cnccc3N3CCNCC3)n2)c2cccc(CN3CCOCC3)c21] | 535.20 | 1.35 |
| 64 | 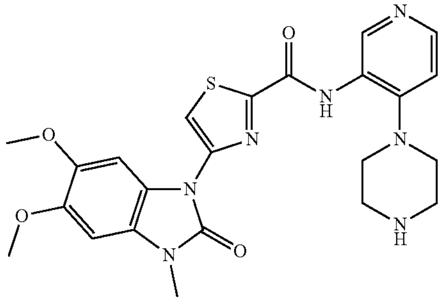 [SMILES: COc1cc2c(cc1OC)n(-c1csc(C(=O)Nc3cnccc3N3CCNCC3)n1)c(=O)n2C] | 496.20 | 1.20 |
| 65 | 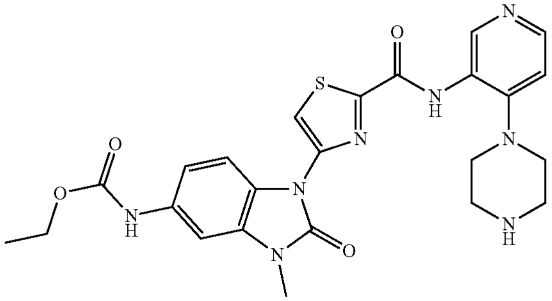 [SMILES: CCOC(=O)Nc1ccc2c(c1)n(C)c(=O)n2-c1csc(C(=O)Nc2cnccc2N2CCNCC2)n1] | 523.20 | 1.30 |
| 66 | 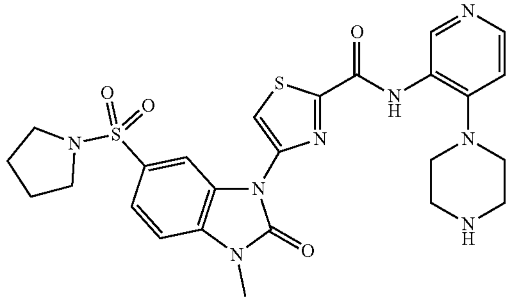 [SMILES: Cn1c(=O)n(-c2csc(C(=O)Nc3cnccc3N3CCNCC3)n2)c2cc(S(=O)(=O)N3CCCC3)ccc21] | 569.20 | 1.10 |
| 67 | 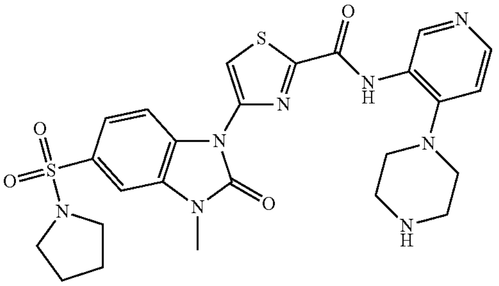 [SMILES: Cn1c(=O)n(-c2csc(C(=O)Nc3cnccc3N3CCNCC3)n2)c2ccc(S(=O)(=O)N3CCCC3)cc21] | 569.20 | 1.10 |

-continued
| Cpd. No. | Structure | LCMS MH⁺ m/z | HPLC MS $t_R$ |
|---|---|---|---|
| 68 | 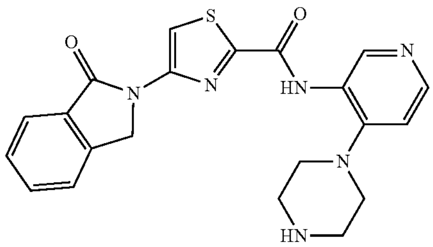 [SMILES: O=C(Nc1cnccc1N1CCNCC1)c1nc(N2Cc3ccccc3C2=O)cs1] | 421.20 | 1.30 |
| 69 | 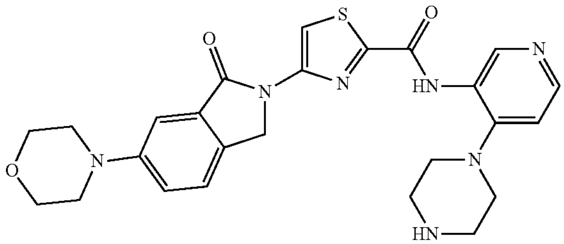 [SMILES: O=C(Nc1cnccc1N1CCNCC1)c1nc(N2Cc3ccc(N4CCOCC4)cc3C2=O)cs1] | 506.20 | 1.10 |
| 70 | 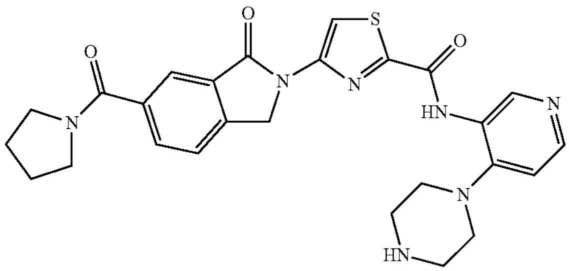 [SMILES: O=C(Nc1cnccc1N1CCNCC1)c1nc(N2Cc3ccc(C(=O)N4CCCC4)cc3C2=O)cs1] | 518.20 | 1.20 |
| 71 | 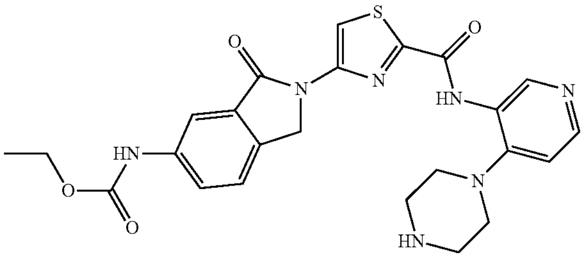 [SMILES: CCOC(=O)Nc1ccc2c(c1)C(=O)N(c1csc(C(=O)Nc3cnccc3N3CCNCC3)n1)C2] | 508.20 | 1.25 |
| 72 | 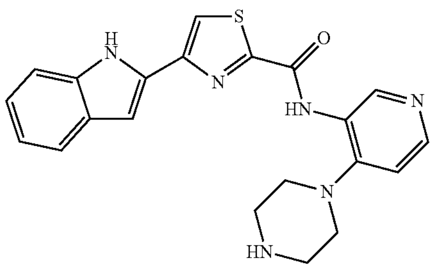 [SMILES: O=C(Nc1cnccc1N1CCNCC1)c1nc(-c2cc3ccccc3[nH]2)cs1] | 405.20 | 1.15 |

-continued

| Cpd. No. | Structure | LCMS MH+ m/z | HPLC MS $t_R$ |
|---|---|---|---|
| 73 | 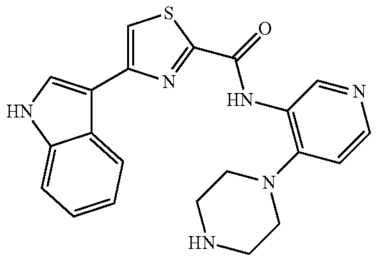 [SMILES: O=C(Nc1cnccc1N1CCNCC1)c1nc(-c2c[nH]c3ccccc23)cs1] | 405.20 | 1.15 |
| 74 | 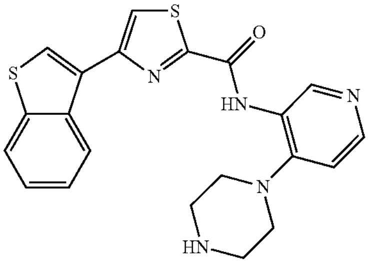 [SMILES: O=C(Nc1cnccc1N1CCNCC1)c1nc(-c2csc3ccccc23)cs1] | 422.20 | 1.35 |
| 75 | 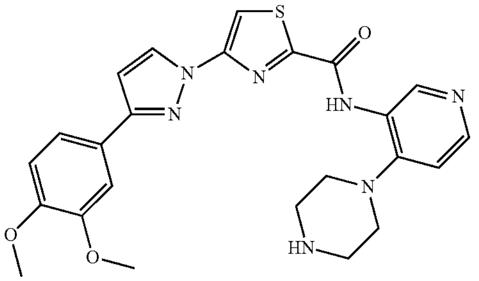 [SMILES: COc1ccc(-c2ccn(-c3csc(C(=O)Nc4cnccc4N4CCNCC4)n3)n2)cc1OC] | 492.20 | 1.40 |
| 76 | 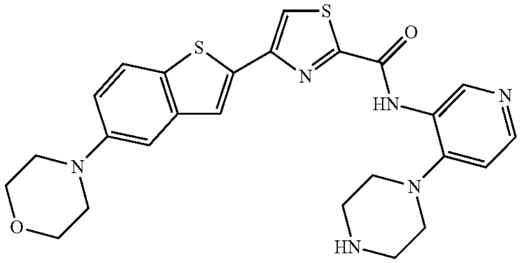 [SMILES: O=C(Nc1cnccc1N1CCNCC1)c1nc(-c2cc3cc(N4CCOCC4)ccc3s2)cs1] | 507.20 | 1.25 |

Example 21

CHK1 SPA Assay

This in vitro assay utilizes recombinant His-CHK1 expressed in the baculovirus expression system as an enzyme source and a biotinylated peptide based on CDC25C as substrate (biotin-RSGLYRSPSMPENLNRPR).

Materials and Reagents:

1) CDC25C Ser 216 C-term Biotinylated peptide substrate (25 mg), stored at −20° C., Custom Synthesis by Research Genetics: biotin-RSGLYRSPSMPENLNRPR 2595.4 MW 2) His-CHK1 In House lot P976, 235 μg/mL, stored at −80° C.

3) D-PBS (without CaCl and MgCl): GIBCO, Cat.#14190-144

4) SPA beads: Amersham, Cat.#SPQ0032: 500 mg/vial

Add 10 mL of D-PBS to 500 mg of SPA beads to make a working concentration of 50 mg/mL. Store at 4° C. Use within 2 week after hydration.

5) 96-Well White Microplate with Bonded GF/B filter: Packard, Cat.#6005177

6) Top seal-A 96 well Adhesive Film: Perkin Elmer, Cat.#6005185

7) 96-well Non-Binding White Polystyrene Plate: Corning, Cat. #6005177

8) $MgCl_2$: Sigma, Cat.#M-8266

9) 1: Promega, Cat.#V3155

10) ATP, stored at 4° C.: Sigma, Cat.#A-5394

11) $\gamma^{33}P$-ATP, 1000-3000 Ci/mMol: Amersham, Cat.#AH9968

12) NaCl: Fisher Scientific, Cat.#BP358-212

13) $H_3PO_4$ 85% Fisher, Cat.#A242-500

14) Tris-HCL pH 8.0: Bio-Whittaker, Cat. #16-015V
15) Staurosporine, 100 μg: CALBIOCHEM, Cat. #569397
16) Hypure Cell Culture Grade Water, 500 mL: HyClone, Cat.#SH30529.02

Reaction Mixtures:

1) Kinase Buffer: 50 mM Tris pH 8.0; 10 mM $MgCl_2$; 1 mM DTT

2) His-CHK1, In House Lot P976, MW ~30 KDa, stored at −80° C.

6 nM is required to yield positive controls of ~5,000 CPM. For 1 plate (100 reaction): dilute 8 μL of 235 μg/mL (7.83 μM) stock in 2 mL Kinase Buffer. This makes a 31 nM mixture. Add 20 μL/well. This makes a final reaction concentration of 6 nM.

3) CDC25C Biotinylated peptide.

Dilute CDC25C to 1 mg/mL (385 μM) stock and store at −20° C. For 1 plate (100 reactions): dilute 10 μL of 1 mg/mL peptide stock in 2 mL Kinase Buffer. This gives a 1.925 μM mix. Add 20 μL/reaction. This makes a final reaction concentration of 385 nM.

4) ATP Mix.

For 1 plate (100 reactions): dilute 10 μL of 1 mM ATP (cold) stock and 2 μL fresh P33-ATP (20 μCi) in 5 mL Kinase Buffer. This gives a 2 μM ATP (cold) solution; add 50 μL/well to start the reaction. Final volume is 100 μL reaction so the final reaction concentrations will be 1 μM ATP (cold) and 0.2 μCi/reaction.

5) Stop Solution:

For 1 plate add: To 10 mL Wash Buffer 2 (2M NaCl 1% $H_3PO_4$): 1 mL. SPA bead slurry (50 mg); Add 100 μL/well 6) Wash buffer 1: 2 M NaCl 7) Wash buffer 2: 2 M NaCl, 1% $H_3PO_4$ Assay Procedure:

| Assay Component | Final Concentration | Volume |
|---|---|---|
| CHK1 | 6 nM | 20 μl/rxn |
| Compound (10% DMSO) | — | 10 μl/rxn |
| CDC25C | 0.385 μM | 20 μl/rxn |
| $\gamma^{33}$P-ATP | 0.2 μCi/rxn | 50 μl/rxn |
| Cold ATP | 1 μM | |
| Stop solution SPA beads | 0.5 mg/rxn | 100 μl/rxn* |
| | | 200 μl/rxn** |

*Total reaction volume for assay.

**Final reaction volume at termination of reaction (after addition of stop solution).

1) Dilute test compounds to desired concentrations in water/10% DMSO—this will give a final DMSO concentration of 1% in the reaction. Dispense 10 μL/reaction to appropriate wells. Add 10 μL 10% DMSO to positive (CHK1+CDC25C+ATP) and negative (CHK1+ATP only) control wells.

2) Thaw enzyme on ice—dilute enzyme to proper concentration in kinase buffer (see Reaction Mixtures) and dispense 20 μL to each well.

3) Thaw the Biotinylated substrate on ice and dilute in kinase buffer (see Reaction Mixtures). Add 20 μL/well except to negative control wells. Instead, add 20 μL Kinase Buffer to these wells.

4) Dilute ATP (cold) and P33-ATP in kinase buffer (see Reaction Mixtures). Add 50 μL/well to start the reaction.

5) Allow the reaction to run for 2 hours at room temperature.

6) Stop reaction by adding 100 μL of the SPA beads/stop solution (see Reaction Mixtures) and leave to incubate for 15 minutes before harvest 7) Place a blank Packard GF/B filter plate into the vacuum filter device (Packard plate harvester) and aspirate 200 mL water through to wet the system.

8) Take out the blank and put in the Packard GF/8 filter plate,

9) Aspirate the reaction through the filter plate.

10) Wash: 200 mL each wash; 1× with 2M NaCl; 1× with 2M NaCl/1% $H_3PO_4$

11) Allow filter plate to dry 15 minutes.

12) Put TopSeal-A adhesive on top of filter plate.

13) Run filter plate in Top Count

Settings:

Data mode: CPM

Radio nuclide: Manual SPA:P33

Scintillator: Liq/plast

Energy Range Low $IC_{50}$ DETERMINATIONS: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

Selected Thiazole Derivatives of the present invention were tested using this assay and provided $IC_{50}$ values ranging from about 1 nM to about 10 μM.

Example 22

CDK2 Assay

BACULOVIRUS CONSTRUCTIONS: Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPDYAS). The expressed protein was approximately 34 kDa in size.

ENZYME PRODUCTION: Recombinant baculoviruses expressing cyan E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed about 15 hours in 2 liters of kinase buffer containing 50 mM Tris pH 8.0, 1 mM DTT, 10 mM $MgCl_2$, 100 μM sodium orthovanadate and 20% glycerol. Enzyme was stored in aliquots at −70° C.

Selected Thiazole Derivatives of the present invention were tested using this assay and provided $IC_{50}$ values ranging from about 300 nM to about 50 μM.

Example 23

In Vitro Cyclin E/CDK2 Kinase Assays

Cyclin E/CDK2 kinase assays can be performed as described below in low protein binding 96-well plates (Corning Inc, Corning, N.Y.).

Enzyme is diluted to a final concentration of 50 μg/mL in kinase buffer containing 50 mM Tris pH 8.0, 10 mM $MgCl_2$, 1 mM DTT, and 0.1 mM sodium orthovanadate. The substrate used in these reactions is a biotinylated peptide derived from Histone H1 (from Amersham, UK). The substrate is thawed on ice and diluted to 2 μM in kinase buffer. Test compounds are diluted in 10% DMSO to desirable concentrations. For each kinase reaction, 20 μL of the 50 μg/mL enzyme solution (1 μg of enzyme) and 20 μl of the 2 μM substrate solution are mixed, then combined with 10 μL of diluted compound in each well for testing. The kinase reaction is initiated by addition of 50 μL of 2 μM ATP and 0.1 μCi of 33P-ATP (from Amersham, UK). The reaction is allowed to run for 1 hour at room temperature, then is stopped by adding 200 μL at of stop buffer containing 0.1% Triton X-100, 1 mM ATP, 5 mM EDTA, and 5 mg/mL streptavidine coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences.). Non-specific signals are eliminated by washing the beads twice with 2M NaCl then twice with 2 M NaCl with 1% phosphoric acid. The radioactive signal can then be measured using, for example, a Top-Count 96 well liquid scintillation counter (from Packard/Perkin Elmer Life Sciences).

$IC_{50}$ DETERMINATIONS: Dose-response curves are plotted from inhibition data generated, each in duplicate, from 8 point serial dilutions of inhibitory compounds. Concentration of compound is plotted against % kinase activity, calculated by CPM of treated samples divided by CPM of untreated samples. To generate $IC_{50}$ values, the dose-response curves are then fitted to a standard sigmoidal curve and $IC_{50}$ values can be derived using nonlinear regression analysis.

Example 24

MEK1 Kinase Assay

Full-length active phosphorylated MEK1 was expressed as a 6× histidine tagged protein ($His_6$-MEK1) by baculovirus infection of Hi-Five cells co-infected with a baculovirus expressing untagged constitutively active Raf-1. Several milligrams of active $His_6$-MEK1 was then purified using Ni-NTA affinity chromatography followed by gel filtration chromatography. Full-length murine catalytically inactive ERK2KR, which had the lysine in subdomain II mutated to arginine was used as a substrate. ERK2KR was expressed from vector pET32aRC in IPTG-induced BL21 D3 *E. coli* as a biotinylated, 6× histidine and thioredoxin tagged fusion protein and purified using Ni-NTA affinity chromatography followed by Mono Q ion exchange chromatography. Kinase reactions were performed in duplicate in a 96-well plate, 33 μl per well at 25° C. for 15 mins, and consisted of 20 nM $His_6$-MEK1, 2 μM ERK2KR, 2 μM ATP, 10 μCi/μL. [γ-$^{33}$P]-ATP, 10 mM $MgCl_2$. 0.01% β-octylglucoside, 1 mM OTT, 20 mM HEPES pH 7.5, 3% DMSO and test compounds ranging from 20 μM down to 0.08 nM. Kinase reactions were stopped by addition of 30 μL of 1.5% o-phosphoric acid, transferred to Millipore Multiscreen-PH plates and incubated for 5 minutes to allow ERK2KR binding. Non-specific activity was estimated from pre-inactivated reactions wherein 30 μL of 1.5% O-phosphoric acid was added per well before addition of enzyme. Stopped plates were washed three times by vacuum filtration with 0.75% O-phosphoric acid followed by two washes with 100% ethanol and air dried, 50 μL of scintillation cocktail was added to each well and $^{33}$P incorporated into ERK2KR was detected using a Wallac Microbeta 1450 JET scintillation counter. Percentage inhibition, $IC_{50}$ and Hill slope values were calculated using ActivityBase software.

Selected Thiazole Derivatives of the present invention were tested using this assay and provided $IC_{50}$ values ranging from about 10 nM to about 100 μM.

Example 25

General Procedure for MEK1 TdF Assays

1 μM protein was mixed with micromolar concentrations (usually 1-50 μM) of compounds in 20 μl of assay buffer (25 mM HEPES, pH 7.4, 300 mM NaCl, 1 mM DTT, 2% DMSO, Sypro Orange 5×) in a white 96-well PCR plate. The plate is sealed by clear strips and placed in a thermocycler (Chromo4, BioRad). The fluorescence intensities are monitored at every 0.5° C. increment during melting from 25° C. to 95° C. The data are exported into an excel sheet and subject to a custom curve fitting algorithm to derive TdF Kd values. All TdF Kd values have an error margin of ~50% due to uncertainty with the enthalpy change of binding.

Selected Thiazole Derivatives of the present invention were tested using this assay and provided $K_d$ values ranging from about 1 μM to about 100 μM.

Example 26

General Procedure for MEK1 Delfia Enzyme Activity Assay

The inhibitory effect of compounds was determined with a DELFIA (Perkin-Elmer) based enzyme assay in which both compound individual percent inhibitions and dose response curves (IC50 determinations) were run. Activated recombinant human MEK1 (5 nanomolar final concentration) in buffer containing Hepes, magnesium chloride, dithiothreitol and ATP (2 micromolar final concentration) was preincubated for 10 minutes, before starting the reaction by addition of the recombinant MEK1 substrate ERK (1 micromolar final concentration), which contains a biotin label. The reaction was run at 20 degrees centigrade for 60 minutes, at which time the reaction was stopped by transfer of reaction aliquots to ROCHE streptavidin microplates (Perkin-Elmer #11734776001) containing DELFIA assay buffer (Perkin-Elmer #4002-0010). After one hour of binding at room temperature with agitation the plates were washed with DELFIA wash buffer (Perkin-Elmer #4010-0010) following which DELFIA assay buffer containing a phosphotyrosine specific antibody (Perkin Elmer #AD0040) was added to the plate and incubated as above for one hour. After a second wash, the plates were developed by addition of Perkin-Elmer enhancement solution (#4001-0010), followed by a 10 minute incubation with agitation. Europium fluorescence was read on a Victor 1420 fluorescent plate reader. Percent inhibition and IC50 determinations were made by comparison of compound containing assays to reaction controls.

Selected Thiazole Derivatives of the present invention were tested using this assay and provided $IC_{50}$ values ranging from about 10 nM to about 100 μM.

Example 27

In Vitro Aurora TdF Assays

Aurora A Assay

Aurora A kinase assays were performed in low protein binding 384-well plates (Corning Inc). All reagents were thawed on ice. Test compounds were diluted in 100% DMSO to desirable concentrations. Each reaction consisted of 8 nM enzyme (Aurora A, Upstate cat#14-511), 100 nM Tamra-PKAtide (Molecular Devices, 5TAMRA-GRTGRRNSI-COOH), 25 μM ATP (Roche), 1 mM DTT (Pierce), and kinase buffer (10 mM Tris, 10 mM MgCl2, 0.01% Tween 20). For each reaction, 14 μl containing TAMRA-PKAtide, ATP, DTT and kinase buffer were combined with 1 μl diluted compound. The kinase reaction was started by the addition of 5 μl diluted enzyme. The reaction was allowed to run for 2 hours at room temperature. The reaction was stopped by adding 60 μl MAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

Aurora B Assay

Aurora A kinase assays were performed in low protein binding 384-well plates (Corning Inc). All reagents were thawed on ice. Compounds were diluted in 100% DMSO to desirable concentrations. Each reaction consisted of 26 nM enzyme (Aurora B, Invitrogen cat#pv3970), 100 nM Tamra-PKAtide (Molecular Devices, 5TAMRA-GRTGRRNSI-COOH), 50 μM ATP (Roche), 1 mM DTT (Pierce), and kinase buffer (10 mM Tris, 10 mM MgCl2, 0.01% Tween 20). For each reaction, 14 μl containing TAMRA-PKAtide, ATP, DTT and kinase buffer were combined with 1 μl diluted compound. The kinase reaction was started by the addition of 5 μl diluted enzyme. The reaction was allowed to run for 2 hours at room temperature. The reaction was stopped by adding 60 μl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

$IC_{50}$ Determinations

Dose-response curves were plotted from inhibition data generated each in duplicate, from 8-point serial dilutions of test compounds. Concentration of compound was plotted against kinase activity, calculated by degree of fluorescent polarization. To generate $IC_{50}$ values, the dose-response curves were then fitted to a standard sigmoidal curve and $IC_{50}$ values were derived by nonlinear regression analysis.

Selected Thiazole Derivatives of the present invention were tested using this assay and provided $K_d$ values ranging from about 1 nM to about 100 μM.

Uses of the Thiazole Derivatives

The Thiazole Derivatives can be useful for treating or preventing a Condition in a patient.

Other diseases and disorders treatable by administration of an effective amount of at least one Thiazole Derivative include, but are not limited to, those disclosed in U.S. Pat. No. 6,413,974, which is incorporated herein by reference in its entirety.

Treatment or Prevention of a Cardiovascular Disease

The Thiazole Derivatives are useful for treating or preventing a cardiovascular disease in a patient.

Accordingly, in one embodiment, the present invention provides a method for treating a cardiovascular disease in a patient, comprising administering to the patient an effective amount of one or more Thiazole Derivatives.

Illustrative examples of cardiovascular diseases treatable or preventable using the present methods, include, but are not limited to atherosclerosis, congestive heart failure, cardiac arrhythmia, myocardial infarction, atrial fibrillation, atrial flutter, circulatory shock, left ventricular hypertrophy, ventricular tachycardia, supraventricular tachycardia, coronary artery disease, angina, infective endocarditis, non-infective endocarditis, cardiomyopathy, peripheral artery disease, Reynaud's phenomenon, deep venous thrombosis, aortic stenosis, mitral stenosis, pulmonic stenosis and tricuspid stenosis.

In one embodiment, the cardiovascular disease is atherosclerosis.

In another embodiment, the cardiovascular disease is congestive heart failure.

In another embodiment, the cardiovascular disease is coronary artery disease.

Treatment or Prevention of a CNS Disorder

The Thiazole Derivatives are useful for treating or preventing a central nervous system (CNS) disorder in a patient.

Accordingly, in one embodiment, the present invention provides a method for treating a CNS disorder in a patient, comprising administering to the patient an effective amount of one or more Thiazole Derivatives.

Illustrative examples of CNS disorders treatable or preventable using the present methods, include, but are not limited to hypoactivity of the central nervous system, hyperactivity of the central nervous system, a neurodegenerative disease, Alzheimer's disease, amyotrophic lateral sclerosis (ALS), Creutzfeldt-Jakob disease, Huntington disease, multiple sclerosis, Lewy body disorder, a tic disorder, Tourette's Syndrome, Parkinson disease, Pick's disease, a priori disease or schizophrenia, epilepsy, migraine, anxiety, bipolar disorder, depression, attention deficit hyperactivity disorder (ADHD) and dementia.

In one embodiment, the CNS disorder is Alzheimer's disease.

In another embodiment, the CNS disorder is Parkinson disease.

In another embodiment, the CNS disorder is ALS.

Treatment or Prevention of a Viral Infection

The Thiazole Derivatives are useful for treating or preventing a viral infection in a patient.

Accordingly, in one embodiment, the present invention provides a method for treating a viral infection in a patient, comprising administering to the patient an effective amount of one or more Thiazole Derivatives.

Illustrative examples of viral infections treatable or preventable using the present methods include, but are not limited to, HIV, human papilloma virus (HPV), herpesvirus, poxvirus, Epstein-Barr virus, Sindbis virus and adenovirus.

In one embodiment the viral infection is HIV.

In another embodiment the viral infection is HPV.

Treatment or Prevention of a Fungal Infection

The Thiazole Derivatives are useful for treating or preventing a fungal infection in a patient.

Accordingly, in one embodiment, the present invention provides a method for treating a fungal infection in a patient, comprising administering to the patient an effective amount of one or more Thiazole Derivatives.

Illustrative examples of fungal infections treatable or preventable using the present methods include, but are not limited to, aspergillosis, blastomycosis, candidiasis, coccidioidomycosis, cryptococcosis, histomplamosis, an opportunistic fungi (including yeasts and molds), mucormycosis, mycetoma, paracoccidioidomycosis and sporotrichosis.

In one embodiment the fungal infection is candidiasis,

Treating or Preventing a Disease Related to the Activity of a Protein Kinase

The Thiazole Derivatives can be inhibitors, regulators or modulators of protein kinases and are useful for treating or preventing a disease related to the activity of a protein kinase in a patient.

Accordingly, in one embodiment, the present invention provides a method for treating a disease related to the activity of a protein kinase in a patient, comprising administering to the patient an effective amount of one or more Thiazole Derivatives.

Illustrative examples of diseases related to the activity of a protein kinase that are treatable or preventable using the present methods include, but are not limited to, cyclin-dependent kinases (CDKs) such as CDK1, CDK2, CDK3, CDK4, CDK5, CDK6 and CDK7, CDK8; aurora kinases such as Aurora-A, Aurora-B and Aurora-C; mitogen activated protein kinase (MAPK/ERK); glycogen synthase kinase 3 (GSK3beta); c-Met kinases, such as c-Met; Pim-1 kinases; checkpoint kinases, such as Chk1 and Chk2; tyrosine kinases, such as the HER subfamily (including, for example, EGFR (HER1), HER2, HERS and HER4), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1 (FLK-1), fetal liver kinase-4 (FLK-4) and the fms-like tyrosine kinase-1 (flt-1)); non-receptor protein tyrosine kinases, for example LCK, Src, Frk, Btk, Csk, Abl, Zap70, Fes/Fps, Fak, Jak, Ack, and LIMK; and growth factor receptor tyrosine kinases such as VEGF-R2, FGF-R, TEK, Akt kinases and the like.

In one embodiment, the present invention provides a method of inhibiting one or more Checkpoint kinases in a patient in need thereof, comprising administering to the patient a therapeutically effective amount of at least one Thiazole Derivative or a pharmaceutically acceptable salt, solvate, ester, prodrug or stereoisomer thereof.

In another embodiment, the present invention provides a method of treating, or slowing the progression of, a disease associated with one or more Checkpoint kinases in a patient in need thereof, comprising administering a therapeutically effective amount of at least one Thiazole Derivative or a pharmaceutically acceptable salt, solvate, ester, prodrug or stereoisomer thereof.

In another embodiment, the present invention provides a method of treating one or more diseases associated with Checkpoint kinase, comprising administering to a patient in need of such treatment at least one Thiazole Derivative, or a pharmaceutically acceptable salt, solvate, ester, prodrug or stereoisomer thereof; and at least one additional anticancer agent, wherein the amounts of the at least one Thiazole Derivative and the at least one anticancer agent result in a therapeutic effect.

In still another embodiment, the present invention provides a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one Thiazole Derivative, or a pharmaceutically acceptable salt, solvate, ester, prodrug or stereoisomer thereof.

In one embodiment, the checkpoint kinase to be inhibited, modulated or regulated is Chk1. In another embodiment, the checkpoint kinase to be inhibited, modulated or regulated is Chk2.

In one embodiment, the present invention provides a method of inhibiting one or more tyrosine kinases in a patient in need thereof, comprising administering to the patient a therapeutically effective amount of at least one Thiazole Derivative or a pharmaceutically acceptable salt, solvate, ester, prodrug or stereoisomer thereof.

In another embodiment, the present invention provides a method of treating, or slowing the progression of, a disease associated with one or more tyrosine kinases in a patient in need thereof, comprising administering a therapeutically effective amount of at least one Thiazole Derivative or a pharmaceutically acceptable salt, solvate, ester, prodrug or stereoisomer thereof.

In another embodiment, the present invention provides a method of treating one or more diseases associated with tyrosine kinase, comprising administering to a patient in need of such treatment at least one Thiazole Derivative, or a pharmaceutically acceptable salt, solvate, ester, prodrug or stereoisomer thereof; and at least one additional anticancer agent, wherein the amounts of the at least one Thiazole Derivative and the at least one anticancer agent result in a therapeutic effect.

In still another embodiment, the present invention provides a method of treating, or slowing the progression of, a disease associated with one or more tyrosine kinases in a patient in need thereof, comprising administering a therapeutically effective amount of a pharmaceutical composition comprising in combination at least one pharmaceutically acceptable carrier and at least one Thiazole Derivative or a pharmaceutically acceptable salt, solvate, ester, prodrug or stereoisomer thereof, In specific embodiments, the tyrosine kinase being inhibited, modulated or regulated is VEGFR (VEGF-R2) EGFR, HER2, SRC, JAK or TEK, or a combination thereof.

In one embodiment, the present invention provides a method of inhibiting one or more Pim-1 kinases in a patient in need thereof, comprising administering to the patient a therapeutically effective amount of at least one Thiazole Derivative or a pharmaceutically acceptable salt, solvate, ester, prodrug or stereoisomer thereof.

In another embodiment, the present invention provides a method of treating, or slowing the progression of, a disease associated with one or more Pim-1 kinases in a patient in need thereof, comprising administering a therapeutically effective amount of at least one Thiazole Derivative or a pharmaceutically acceptable salt, solvate, ester, prodrug or stereoisomer thereof.

In another embodiment, the present invention provides a method of treating one or more diseases associated with Pim-1 kinase, comprising administering to a patient in need of such treatment at least one Thiazole Derivative, or a pharmaceutically acceptable salt, solvate, ester, prodrug or stereoisomer thereof; and at least one additional anticancer agent, wherein the amounts of the at least one Thiazole Derivative and the at least one anticancer agent result in a therapeutic effect.

In still another embodiment, the present invention provides a method of treating, or slowing the progression of, a disease associated with one or more Pim-1 kinases in a patient in need thereof, comprising administering a therapeutically effective amount of a pharmaceutical composition comprising in combination at least one pharmaceutically acceptable carrier and at least one Thiazole Derivative or a pharmaceutically acceptable salt, solvate, ester, prodrug or stereoisomer thereof.

In one embodiment, the present invention provides a method of treating one or more diseases associated with an Aurora kinase, comprising administering to a patient in need of such treatment at least one Thiazole Derivative, or a pharmaceutically acceptable salt, solvate, ester, prodrug or stereoisomer thereof; and at least one additional anticancer agent, wherein the amounts of the at least one Thiazole Derivative and the at least one anticancer agent result in a therapeutic effect.

In another embodiment, the present invention provides a method of treating, or slowing the progression of, a disease associated with one or more Aurora kinases in a patient in need thereof, comprising administering a therapeutically effective amount of a pharmaceutical composition comprising in combination at least one pharmaceutically acceptable carrier and at least one Thiazole Derivative or a pharmaceutically acceptable salt, solvate, ester, prodrug or stereoisomer thereof.

In one embodiment, the present invention provides a method of treating one or more diseases associated with a cyclin dependent kinase, comprising administering to a patient in need of such treatment an amount of a first compound, which is an Thiazole Derivative, or a pharmaceutically acceptable salt, solvate, ester, prodrug or stereoisomer thereof; and an amount of at least one second compound, the second compound being an anticancer agent different from the Thiazole Derivative, wherein the amounts of the first compound and the second compound result in a therapeutic effect.

The Thiazole Derivatives can also be useful for inhibiting oncogenes that encode for protein kinases. Non-limiting examples of such oncogenes include C-Met.

Treatment or Prevention of a Proliferative Disorder

The Thiazole Derivatives are useful for treating or preventing a proliferative disorder in a patient.

Accordingly, in one embodiment, the present invention provides a method for treating a proliferative disorder in a patient, comprising administering to the patient an effective amount of one or more Thiazole Derivatives.

Illustrative examples of proliferative disorders treatable or preventable using the present methods include, but are not limited to, cancer, atherosclerosis, benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, idiopathic pulmonary fibrosis, scleroderma and cirrhosis of the liver.

Induction or Inhibition of Apoptosis

The Thiazole Derivatives are useful for inducing or inhibiting apoptosis in a patient.

Accordingly, in one embodiment, the present invention provides a method for inducing or inhibiting apoptosis in a patient, comprising administering to the patient an effective amount of one or more Thiazole Derivatives.

The apoptotic response is aberrant in a variety of human diseases and the Thiazole Derivatives, as modulators of apoptosis, can be useful for the treatment of cancer, a viral infection, prevention of AIDS development in HIV-infected individuals, an autoimmune disease (including but not limited to systemic lupus, erythematosus, autoimmune mediated glomerulonephritis, rheumatoid arthritis, psoriasis, inflammatory bowel disease, and autoimmune diabetes mellitus), a neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), a myelodysplastic syndrome, aplastic anemia, an ischemic injury associated with myocardial infarction, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Treatment or Prevention of Cancer

The Thiazole Derivatives are useful for treating or preventing cancer in a patient.

Accordingly, in one embodiment, the present invention provides a method for treating cancer in a patient, comprising administering to the patient an effective amount of one or more Thiazole Derivatives.

Illustrative examples of cancers treatable or preventable using the present methods include, but are not limited to cancers of the bladder, breast, colon, rectum, kidney, liver, lung (including small cell lung cancer, non-small cell lung cancer, mesothelioma, and giant cell cancer), head and neck, esophagus, gall bladder, ovary, pancreas, stomach, cervix, thyroid, prostate or skin (including squamous cell carcinoma and melanoma); hematopoietic tumors of lymphoid lineage (including but not limited to, a leukemia such as acute lymphocytic leukemia, chronic lymphocytic leukemia or acute lymphoblastic leukemia; a lymphoma, such as B-cell lymphoma, T-cell lymphoma, Hodgkins lymphoma, non-Hodgkins lymphoma, hairy cell lymphoma, mantle cell lymphoma, myeloma or Burkett's lymphoma); a cancer of unknown origin; hematopoietic tumors of myeloid lineage, including but not limited to, acute and chronic myelogenous leukemias, myelodysplastic syndrome and promyelocytic leukemia; tumors of mesenchymal origin, including but not limited to, fibrosarcoma and rhabdomyosarcoma; tumors of the central and peripheral nervous system, including but not limited to brain tumors such as an astrocytoma, a neuroblastoma, a glioma (such as glioblastoma multiforme) or a schwannoma; and other tumors, including seminoma, teratocarcinoma, osteosarcoma, xenoderoma pigmentosum, keratoctanthoma, thyroid follicular cancer and Kaposi's sarcoma. The Thiazole Derivatives are useful for treating primary and/or metastatic cancers.

The Thiazole Derivatives may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The Thiazole Derivatives may also be useful in inhibiting tumor angiogenesis and metastasis.

In one embodiment, the cancer treated or prevented is selected from: breast cancer, colorectal cancer, lung cancer, prostate cancer, ovarian cancer, pancreatic cancer, skin cancer, a leukemia and a lymphoma.

In another embodiment, the cancer treated or prevented is selected from: breast cancer, colorectal cancer, lung cancer and prostate cancer.

In one embodiment, the cancer treated or prevented is breast cancer.

In another embodiment, the cancer treated or prevented is lung cancer.

In another embodiment, the cancer treated or prevented is colorectal cancer.

In still another embodiment, the cancer treated or prevented is prostate cancer.

In still another embodiment, the cancer treated or prevented is a leukemia.

In still another embodiment, the cancer treated or prevented is a lymphoma.

In one embodiment, the cancer treated or prevented is a solid tumor.

In another embodiment, the cancer treated or prevented is a cancer of blood or lymph.

In one embodiment, the cancer treated or prevented is a primary cancer.

In another embodiment, the cancer treated or prevented is a metastatic cancer.

In a further embodiment, the patient is being treated for both primary and metastatic cancer.

Combination Therapy

In one embodiment, the present invention provides methods for treating a Condition in a patient, the method comprising administering to the patient one or more Thiazole Derivatives, or a pharmaceutically acceptable salt, solvate, ester or prodrug thereof and at least one additional therapeutic agent that is not an Thiazole Derivative, wherein the amounts administered are together effective to treat or prevent a Condition.

Additional therapeutic agents useful in the present methods include, but are not limited to, an anticancer agent, an agent useful for treating a cardiovascular disease, an agent useful for treating a CNS disorder, an antiviral agent, an antifungal agent, an anti-proliferative agent, an anti-alopecia agent, an anti-inflammatory agent, an agent useful for the treatment of a protein kinase-related disorder, an anti-ischemic agent or any combination of two or more of these agents.

In another embodiment, the other therapeutic agent is an agent useful for reducing any potential side effect of an Thiazole Derivative. Such potential side effects include, but are not limited to, nausea, vomiting, headache, fever, lethargy, muscle aches, diarrhea, general pain, and pain at an injection site.

When administering a combination therapy to a patient in need of such administration, the therapeutic agents in the combination, or a composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Thiazole Derivatives are administered during a time when the additional therapeutic agent(s) exert their prophylactic or therapeutic effect, or vice versa.

In another embodiment, the one or more Thiazole Derivatives and the additional therapeutic agent(s) are administered in doses commonly employed when such agents are used as monotherapy for treating a Condition.

In another embodiment, the one or more Thiazole Derivatives and the additional therapeutic agent(s) are administered in doses lower than the doses commonly employed when such agents are used as monotherapy for treating a Condition.

In still another embodiment, the one or more Thiazole Derivatives and the additional therapeutic agent(s) act synergistically and are administered in doses lower than the doses commonly employed when such agents are used as monotherapy for treating a Condition.

In one embodiment, the one or more Thiazole Derivatives and the additional therapeutic agent(s) are present in the same composition. In one embodiment, this composition is suitable for oral administration. In another embodiment, this composition is suitable for intravenous administration.

The one or more Thiazole Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Thiazole Derivatives and the additional therapeutic agent(s) may inhibit the resistance of a Condition to one or more of these agents.

In one embodiment, the additional therapeutic agent is used at its known therapeutically effective dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in the combination therapies of the present invention for the treatment or prevention of a Condition can be determined by the attending clinician, taking into consideration the approved doses and dosage regimen in the package insert: the age, sex and general health of the patient; and the type and severity of the viral infection or related disease or disorder. When administered in combination, the Thiazole Derivative(s) and the other agent(s) for treating diseases or conditions listed above can be administered simultaneously or sequentially. This particularly useful when the components of the combination are given on different dosing schedules, e.g., one component is administered once daily and another every six hours, or when the compositions are different, e.g. one is a tablet and one is a capsule. A kit comprising the separate dosage forms is therefore advantageous.

Generally, a total daily dosage of the one or more Thiazole Derivatives and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses.

In a further embodiment, the dosage is from about 1 to about 20 mg/day, administered in a single dose or in 2-4 divided doses.

Combination Therapy for the Treatment of Cancer

The compounds of this invention may also be useful in combination (administered together or sequentially in any order) with one or more separate anticancer treatments such as surgery, radiation therapy, biological therapy (e.g., anticancer vaccine therapy) and/or the administration of at least one additional anticancer agent different from the Thiazole Derivatives, in order to treat or prevent cancer in a patient. The compounds of the present invention can be present in the same dosage unit as the additional anticancer agent(s) or in separate dosage units.

Non-limiting examples of additional anticancer agents (also known as anti-neoplastic agents) suitable for use in combination with the compounds of the present invention include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide or teniposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other useful additional anticancer agents include but are not limited to Uracil mustard, Chlormethine, Ifosfamide, Melphalan, Chlorambucil, Pipobroman, Triethylenemelamine, ara-C, adriamycin, cytoxan. Clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other useful additional anticancer agents include but are not limited to Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Oxaliplatin, Aroplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Fulvestrant, Ifosfomide, Rituximab, C225 and Campath.

In one embodiment, the other anticancer agent is selected from: a cytostatic agent, cisplatin, doxorubicin, taxotere, taxol, etoposide, irinotecan, camptostar, topotecan, paclitaxel docetaxel, epothilones, tamoxifen, 5-fluorouracil, methoxtrexate, temozolomide, cyclophosphamide, SCH 66336, R115777, L778,123, BMS 214662. Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine. Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Ifosfomide, Rituximab, C225, Doxil, Ontak, Deposyt, Mylotarg, Campath, Celebrex, Sutent, Aranesp, Neupogen, Neulasta, Kepivance, SU11248, and PTK787, In one embodiment, the other anticancer agent is a platinum-based agent, such as cisplatin, carboplatin or oxaliplatin.

In another embodiment, the other anticancer agent is an alkylating agent.

In another embodiment, the other anticancer agent is a vinca alkaloid, such as vincristine or vinblastine.

In still another embodiment, the other anticancer agent is a topoisomerase I inhibitor.

In another embodiment, the other anticancer agent is a topoisomerase II inhibitor.

In a further embodiment, the other anticancer agent is an antimetabolite.

In another embodiment, the other anticancer agent is a spindle poison.

In another embodiment, the other anticancer agent is an antitumor antibiotic.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci*., (1995) 108, 2897. Thiazole Derivatives may also be administered sequentially with known anticancer or cytotoxic agents when a combination formulation is inappropriate. The invention is not limited in the sequence of administration; Thiazole Derivatives may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes methods for treating cancer in a patient, comprising administering to the patient an amount of at least one Thiazole Derivative, or a pharmaceutically acceptable salt, solvate, ester, prodrug or stereoisomer thereof, and one or more other anticancer treatment modalities, wherein the amounts of the Thiazole Derivative(s)/other treatment modality result in the desired therapeutic effect. In one embodiment, the at least one Thiazole Derivative and the one or more other treatment modalities act synergistically. In another embodiment, the at least one Thiazole Derivative and the one or more other treatment modalities act additively.

In one embodiment, the other treatment modality is surgery.

In another embodiment, the other treatment modality is radiation therapy.

In another embodiment, the other treatment modality is biological therapy, such as hormonal therapy or anticancer vaccine therapy.

The pharmacological properties of the compounds of this invention may be confirmed by a number of pharmacological assays. The exemplified pharmacological assays which are described herein below have been carried out with compounds according to the invention and their salts, solvates, esters or prodrugs.

Compositions and Administration

This invention is also directed to pharmaceutical compositions which comprise at least one Thiazole Derivative, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the Thiazole Derivatives. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day, in still another embodiment, a daily dosage regimen for oral administration is from about 50 mg/day to 100 mg/day, in a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

Kits

In one aspect, the present invention provides a kit comprising an effective amount of one or more Thiazole Derivatives, or a pharmaceutically acceptable salt, solvate, ester or prodrug thereof, and a pharmaceutically acceptable carrier.

In another aspect the present invention provides a kit comprising an amount of one or more Thiazole Derivatives, or a pharmaceutically acceptable salt, solvate, ester or prodrug thereof, and an amount of at least one additional therapeutic agent listed above, wherein the combined amounts are effective for treating or preventing a Condition in a patient.

When the components of a combination therapy regimen are to be administered in more than one composition, they can be provided in a kit comprising a single package containing one or more containers, wherein one container contains one or more Thiazole Derivatives in a pharmaceutically acceptable carrier, and a second, separate container comprises an additional therapeutic agent in a pharmaceutically acceptable carrier, with the active components of each composition being present in amounts such that the combination is therapeutically effective.

In another aspect the present invention provides a kit comprising an amount of at least one Thiazole Derivative, or a pharmaceutically acceptable salt, solvate, ester or prodrug of said compound and an amount of at least one anticancer therapy and/or additional anticancer agent listed above, wherein the amounts of the two or more ingredients result in the desired therapeutic effect.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound having the formula:

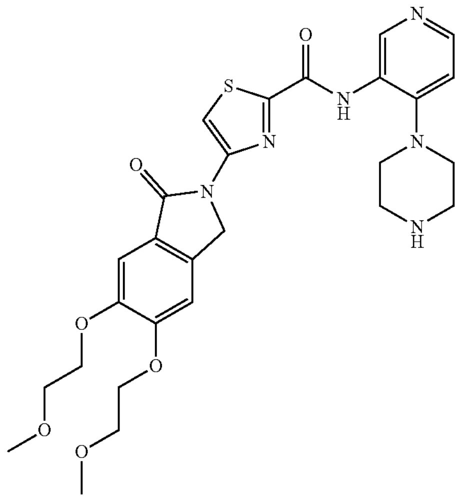 [SMILES: COCCOc1cc2c(cc1OCCOC)C(=O)N(c1csc(C(=O)Nc3cnccc3N3CCNCC3)n1)C2]

or a pharmaceutically acceptable salt thereof.

2. A pharmaceutical composition comprising an effective amount of at least one compound of claim 1 or a pharmaceutically acceptable salt thereof, and a pharmaceutically acceptable carrier or diluent.

* * * * *

UNITED STATES PATENT AND TRADEMARK OFFICE

CERTIFICATE OF CORRECTION

PATENT NO. : 8,476,278 B2
APPLICATION NO. : 12/738487
DATED : July 2, 2013
INVENTOR(S) : Reddy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 412 days.

Signed and Sealed this
Eighth Day of September, 2015

Michelle K. Lee
*Director of the United States Patent and Trademark Office*